United States Patent
Schultz et al.

(10) Patent No.: US 10,512,634 B2
(45) Date of Patent: Dec. 24, 2019

(54) BENZIMIDAZOLE DERIVATES USEFUL AS INHIBITORS OF MAMMALIAN HISTONE DEACETYLASE ACTIVITY

(71) Applicant: KANCERA AB, Solna (SE)

(72) Inventors: Johan Schultz, Stockholm (SE); Jan Vågberg, Sollentuna (SE); Elisabeth Olsson, Sollentuna (SE); Katarina Färnegårdh, Ekerö (SE); Mattias Jönsson, Knivsta (SE); Kristin Hammer, Sollentuna (SE); Lars Krüger, Huddinge (SE)

(73) Assignee: KANCERA AB (SE)

( * ) Notice: Subject to any disclaimer, the term of this patent is extended or adjusted under 35 U.S.C. 154(b) by 0 days.

(21) Appl. No.: 15/573,439

(22) PCT Filed: May 11, 2015

(86) PCT No.: PCT/EP2015/060393
§ 371 (c)(1),
(2) Date: Nov. 10, 2017

(87) PCT Pub. No.: WO2016/180472
PCT Pub. Date: Nov. 17, 2016

(65) Prior Publication Data
US 2018/0110755 A1    Apr. 26, 2018

(51) Int. Cl.
| | | |
|---|---|---|
| C07D 235/18 | (2006.01) |
| A61K 31/4184 | (2006.01) |
| C07D 403/04 | (2006.01) |
| C07D 405/04 | (2006.01) |
| A61P 37/00 | (2006.01) |
| A61P 25/00 | (2006.01) |
| A61P 35/00 | (2006.01) |

(52) U.S. Cl.
CPC .......... *A61K 31/4184* (2013.01); *A61P 25/00* (2018.01); *A61P 35/00* (2018.01); *A61P 37/00* (2018.01); *C07D 235/18* (2013.01); *C07D 403/04* (2013.01); *C07D 405/04* (2013.01); *C12Y 305/01098* (2013.01)

(58) Field of Classification Search
CPC ........................... C07D 235/18; C07D 235/08
USPC ........................ 548/309.7; 514/394
See application file for complete search history.

(56) References Cited

FOREIGN PATENT DOCUMENTS

| WO | 2005028447 | 3/2005 |
| WO | 2005066151 | 7/2005 |

OTHER PUBLICATIONS

Aldana-Masangkay GI, Sakamoto KM. The role of HDAC6 in cancer. J Biomed Biotechnol 2011, doi:10.1155/2011/875824.

Balasubramanian S, Ramos J, Luo W, Sirisawad M, Verner E, Buggy JJ. A novel histone deacetylase 8 (HDAC8)-specific inhibitor PCI-34051 induces apoptosis in T-cell lymphomas. Leukemia. 2008; 22:1026-1034.

Balasubramanian, S.; Verner, E. V.; Buggy, J. J. Isoform-specific histone deacetylase inhibitors: the next step? Cancer Lett. 2009, 280, 211.

Bazzaro M, Lin Z, Santillan A et al., "Ubiquitin proteasome system stress underlies synergistic killing of ovarian cancer cells by bortezomib and a novel HDAC6 inhibitor," *Clinical Cancer Research*, 2008, vol. 14, No. 22, pp. 7340-7347.

Best, J. D.; Carey, N. Epigenetic therapies for non-oncology indications. Drug Discovery Today 2010, 15, 1008-1014.

Bradner JE, West N, Grachan ML, Greenberg EF, Haggarty SJ, Warnow T et al. Chemical phylogenetics of histone deacetylases. Nat Chem Biol 2010, 6, 238-243.

Brana I, Taberno J. Cardiotoxicity, Annals of Oncology 2010, 21, Supplement 7: vii173-vii179.

Chen, Y.; He, R.; D'Annibale, M. A.; Langley, B.; Kozikowski, A.P. Studies of benzamide- and thiol-based histone deacetylase inhibitorsin models of oxidative-stress-induced neuronal death: identification of some HDAC3-selective inhibitors. ChemMedChem 2009, 4, 842-852.

Choudhary C, Kumar C, Gnad F, Nielsen ML, Rehman M, Walther TC et al. Lysine acetylation targets protein complexes and co-regulates major cellular functions. Science 2009, 325, 834-840.

Cook C, Gendron Tf, Scheffel K, Carlomagno Y, Dunmore J, DeTure M, Petrucelli L. Loss of HDAC6, a novel CHIP substrate, alleviates abnormal tau accumulation. Hum Mol Genet 2012, 21, 2936-2945.

Cook C, Petrucelli L. 2013. Tau triage decisions mediated by the chaperone network. J Alzheimers Dis 33 Suppl 1:S145-S151.

de Zoeten, E. F.; Wang, L.; Butler, K.; Beier, U. H.; Akimova, T.; Sai, H.; Bradner, J. E.; Mazitschek, R.; Kozikowski, A. P.; Matthias, P.; Hancock, W. W. Histone deacetylase 6 and heat shock protein 90 control the functions of Foxp3(+) T-regulatory cells. Mol. Cell. Biol. 2011, 31, 2066-2078.

D'Ydewalle C, Krishnan J, Chiheb DM, Van Damme P, Irobi J, Kozikowski AP, Vanden Berghe P, Timmerman V, Robberecht W, Van Den Bosch L: HDAC6 inhibitors reverse axonal loss in a mouse model of mutant HSPB1-induced Charcot-Marie-Tooth disease. Nat Med 2011, 17:968-974.

(Continued)

*Primary Examiner* — Patricia L Morris
(74) *Attorney, Agent, or Firm* — Adsero IP

(57) ABSTRACT

A compound of formula (I) or a pharmaceutically acceptable salt thereof, and a pharmaceutical composition comprising the compound. The compound is useful in therapy, for the treatment of disorders mediated by HDAC6, such as autoimmune disorders, neurodegenerative disorders and hyperproliferative disorders, such as cancer.

(I)

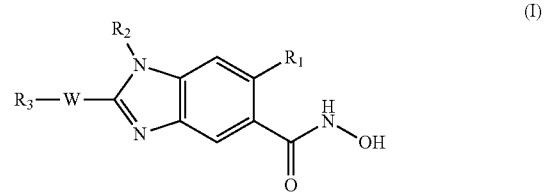

17 Claims, No Drawings

(56) References Cited

OTHER PUBLICATIONS

Espallergues J, Teegarden SL, Veerakumar A, Boulden J, Challis C, Jochems J, Chan M, Petersen T, Deneris E, Matthias P, Hahn CG, Lucki I, Beck SG, Berton O. HDAC6 regulates glucocorticoid receptor signaling in serotonin pathways with critical impact on stress resilience. J Neurosci 2012, 32, 4400-4416.

Fukada M, Hanai A, Nakayama A, Suzuki T, Miyata N, Rodriguiz RM, Wetsel WC, Yao TP, Kawaguchi Y. Loss of deacetylation activity of HDAC6 affects emotional behavior in mice. PLoS ONE 2012, 7, e30924.

George, P., Bali, P., Annavarapu, S., Scuto, A., Fiskus, W., Guo, F., Sigua, C., Sondarva, G., Moscinski, L., Atadja, P. et al. Combination of the histone deacetylase inhibitor LBH589 and the hsp90 inhibitor 17-AAG is highly active against human CML-BC cells and AML cells with activating mutation of FLT-3. Blood, 2005, 105, 1768-1776.

Govindarajan N, Rao P, Burkhardt S, Sananbenesi F, Schlüter OM, Bradke F, Lu J, Fischer A: Reducing HDAC6 ameliorates cognitive deficits in a mouse model for Alzheimer's disease. EMBO Mol Med 2013, 5:52-63.

Greer J. M.; McCombe, P. A. The role of epigenetic mechanisms and processes in autoimmune disorders. Biologics 2012, 6, 307-327.

Gregoretti, I.V., Lee, Y.M. & Goodson, H.V. Molecular evolution of the histone deacetylase family: functional implications of phylogenetic analysis. J. Mol. Biol. 2004, 338, 17-31.

Hauser AT, Jung M, Jung M. Assays for histone deacetylases. Curr Top Med Chem 2009, 9, 227-234.

Hideshima, T.; Bradner, J. E.;, Wong J. et al., Small-molecule inhibition of proteasome and aggresome function induces synergistic antitumor activity in multiple myeloma, Proc. Natl. Acad. Sci. U.S.A., 2005, 102, 8567-8572.

Jochems J, Boulden J, Lee BG, Blendy JA, Jarpe M, Mazitschek R, Van Duzer JH, Jones S and Berton O. Antidepressant-Like Properties of Novel HDAC6-Selective Inhibitors with Improved Brain Bioavailability. Neuropsychopharmacology 2014, 39, 389-400.

Kalin JH, Bergman JA. Development and therapeutic implications of selective histone deacetylase 6 inhibitors. J Med Chem 2013, 56, 6297-6313.

Karberg, S. Switching on epigenetic therapy. Cell 2009, 139, 1029-1031.

Kawaguchi Y. Loss of deacetylation activity of Hdac6 affects emotional behavior in mice. PloSone 2012, 7, e30924.

Kim, C.; Choi, H.; Jung, E. S.; Lee, W.; Oh, S.; Jeon, N. L.; Mook-Jung, I. HDAC6 inhibitor blocks amyloid beta-induced impairment of mitochondrial transport in hippocampal neurons. PLoS One 2012, 7, e42983.

Kim, D.; Frank, C. L.; Dobbin, M. M.; Tsunemoto, R. K.; Tu, W.; Peng, P. L.; Guan, J. S.; Lee, B. H.; Moy, L. Y.; Giusti, P.; Broodie, N.; Mazitschek, R.; Delalle, I.; Haggarty, S. J.; Neve, R. L.; Lu, Y.; Tsai, L. H. Deregulation of HDAC1 by p25/Cdk5 in neurotoxicity. Neuron 2008, 60, 803-817.

Kouzarides, T. Chromatin modifications and their function. Cell 2007, 128, 693-705.

Lee J.K.; Zheng B. Role of myelin-associated inhibitors in axonal repair after spinal cord injury. Exp Neurol 2012, 235:33-42.

Lee, Y. S.; Lim, K. H.; Guo, X.; Kawaguchi, Y.; Gao, Y.; Barrientos, T.; Ordentlich, P., Wang, X. F.; Counter, C. M.; Yao, T. P. The cytoplasmic deacetylase HDAC6 is required for efficient oncogenic tumorigenesis. Cancer Res. 2008, 68, 7561-7569.

Morris MJ, Karra AS, Monteggia LM. Histone deacetylates govern cellular mechanisms underlying behavioral and synaptic plasticity in the developing and adult brain. Behav Pharmacol. 2010, 21, 409-419.

Parmigiani, R. B.; Xu, W. S.; Venta-Perez, G.; Erdjument-Bromage, H.; Yaneva, M.; Tempst, P.; Marks, P. A. HDAC6 is a specific deacetylase of peroxiredoxins and is involved in redox regulation. Proc. Natl. Acad. Sci. U.S.A. 2008, 105, 9633-9638.

Prince HM, Bishton MJ, Harrison SJ. Clinical studies of histone deacetylase inhibitors. Clin Cancer Res 2009; 15, 3958-3969.

Raje N, Vogl DT, Hari PN, Jagannath S, Jones SS, Supko JG, Leone G, Wheeler C, Orlowski RZ, Richardson PG, and Lonial S. ACY-1215, a Selective Histone Deacetylase (HDAC) 6 Inhibitor: Interim Results of Combination Therapy With Bortezomib in Patients With Multiple Myeloma (MM). ASH 2013 Annual Meeting Abstract 759.

Rao, R., Fiskus, W., Yang, Y., Lee, P., Joshi, R., Fernandez, P., Mandawat, A., Atadja, P., Bradner, J.E. and Bhalla, K. HDAC6 inhibition enhances 17-AAG-mediated abrogation of hsp90 chaperone function in human leukemia cells. Blood, 2008, 112, 1886-1893.

Santo L, Hideshima T, Kung AL, Tseng J-C, Tamang D, Yang M, Jarpe M, van Duzer JH, Mazitschek R, Ogier WC, Cirstea D, Rodig S, Eda H, Scullen T, Canavese M, Bradner J, Anderson KC, Jones SS, Raje N. Preclinical activity, pharmacodynamic, and pharmacokinetic properties of a selective HDAC6 inhibitor, ACY-1215, in combination with bortezomib in multiple myeloma. Blood 2012, 119:11, 2579-2589.

Simões-Pires C, Zwick V, Nurisso A, Schenker E, Carrupt P-A and Cuendet M. HDAC6 as a target for neurodegenerative diseases: what makes it different from the other HDACs? Molecular Neurodegeneration 2013, 8:7, 1-16.

Smith, B.C., Hallows, W.C. & Denu, J.M. Mechanisms and molecular probes of sirtuins. Chem. Biol. 2008, 15, 1002-1013.

Southwood CM, Peppi M, Dryden S, Tainsky MA, Gow A. Microtubule deacetylases, SirT2 and HDAC6, in the nervous system. Neurochem Res 2007, 32,187-195.

Ververis, K., Hiong, A., Karagiannis, T.C., and Licciardi, P.V. "Histone deacetylase inhibitors (HDACIs): multitargeted anticancer agents", Biologics: Targets and Therapy 2013, 7 47-60.

Witt, O.; Deubzer, H. E.; Milde, T.; Oehme, I. HDAC family: What are the cancer relevant targets? Cancer Lett. 2009, 277, 8-21.

Xu X, Kozikowski Ap, Pozzo-Miller L. A selective histone deacetylase-6 inhibitor improves BDNF trafficking in hippocampal neurons from Mecp2 knockout mice: implications for Rett syndrome. Frontiers in Cellular Neuroscience 2014, 8:68, 1-9.

Zhang, Y.; Kwon, S.; Yamaguchi, T.; Cubizolles, F.; Rousseaux, S.; Kneissel, M.; Cao, C.; Li, N.; Cheng, H. L.; Chua, K.; Lombard, D.; Mizeracki, A.; Matthias, G.; Alt, F. W.; Khochbin, S.; Matthias, P. Mice lacking histone deacetylase 6 have hyperacetylated tubulin but are viable and develop normally. Mol. Cell. Biol. 2008, 28, 1688-1701.

Zhao, S. et al. Regulation of cellular metabolism by protein lysine acetylation. Science 2010, 327, 1000-1004.

Database registry accession No. 1348107-56-1, retrieved from C:\EPODATA\SEA\eplogf\SA1360230.log on Jul. 27, 2015, 1 page.

International Search Report for PCT/EP2015/060393 dated Jul. 27, 2015, 4 pages.

BENZIMIDAZOLE DERIVATES USEFUL AS INHIBITORS OF MAMMALIAN HISTONE DEACETYLASE ACTIVITY

CROSS-REFERENCE TO RELATED APPLICATION

This application claims priority to and is a 35 U.S.C. § 371 national phase application of PCT/EP2015/060393 (WO2016/180472), filed on May 11, 2015 entitled "BENZIMIDAZOLE DERIVATES USEFUL AS INHIBITORS OF MAMMALIAN HISTONE DEACETYLASE ACTIVITY", the disclosure of which is incorporated herein by reference in its entirety.

FIELD OF THE INVENTION

The present invention relates to novel benzimidazole derivatives. More particularly, the invention relates to novel benzimidazole derivatives useful as inhibitors of histone deacetylase, and to their use in therapy.

BACKGROUND OF THE INVENTION

Histone deacetylases (HDACs) are a class of enzymes involved in removing the acetyl groups from an ε-N-acetyl lysine amino acid from other proteins, mainly histones. The histones are an essential part of how the genome is stored in the cell nucleus and DNA expression is regulated by histone acetylation and de-acetylation. Lysine acetylation is a key post-translational modification of many proteins, and which underlie many aspects of gene transcription, cellular signaling, cellular transport and metabolic changes (Kouzarides et al. 2007, Choudhary et al. 2009, Zhao et al. 2010). HDACs have pivotal roles in the regulation of gene expression, forming complexes with DNA binding proteins and thereby affecting histone acetylation and chromatin accessibility at promoter regions. These enzymes also have non-histone substrates, such as transcription factors and structural proteins whose biological activity is partly regulated by acetylation.

The common classification of human deacetylases is based on molecular phylogenetic analysis of primary structure, subsequently grouped based on homology to yeast enzymes (Gregoretti et al. 2004). This approach yields four distinct classes that vary in size and function. Class I (HDAC1, HDAC2, HDAC3 and HDAC8), class IIa (HDAC4, HDAC5, HDAC7 and HDAC9), class IIb (HDAC6 and HDAC10) and class IV (HDAC11). The HDACs require a divalent ion for catalysis. The class III proteins form a structurally and mechanistically distinct class of hydrolases dependent on nicotinamide adenine dinucleotide (NAD$^+$) (sirtuins, Sirt1-Sirt7) (Smith et al. 2008). The class I HDACs are found primarily in the nucleus, while the class IIa and class IIb HDACs are able to translocate in and out of the nucleus, depending on different signals.

There are numerous diseases that are related to dysregulated HDAC enzymatic function, including cancer, autoimmune and neurodegenerative disorders (Karberg 2009). For example, overexpression of specific HDACs has been identified in a range of human cancers, including HDAC1 in gastric and prostate cancer, HDAC1 and HDAC6 in breast cancer, and HDAC2 and HDAC3 in colorectal cancer (Ververis et al. 2013). Extensive cell-based assays and clinical studies with HDAC inhibitors have been shown to reduce proliferation, induce cell death and apoptosis, cause cell-cycle arrest, and prevent differentiation and migration selectively in malignant and transformed cells with little effect in normal cells (Ververis et al. 2013). Thus, HDAC inhibitors have the potential to be used as monotherapies in oncology. In addition to their intrinsic cytotoxic properties when tested as a single treatment, HDAC inhibitors have been shown to induce additive cytotoxic effects when used in combination with conventional anticancer therapies, such as chemotherapy (anthracyclines and retinoic acid) and radiotherapy. Furthermore, studies with HDAC inhibitors in combination with ultraviolet radiation and potent iodinated DNA minor groove-binding ligands have been shown to augment photosensitization and cytotoxicity in tumor (Ververis et al. 2013).

Currently, there are two HDAC inhibitors that have received approval from the US FDA for the treatment of cutaneous T-cell lymphoma: vorinostat (suberoylanilide hydroxamic acid, Zolinza) and depsipeptide (romidepsin, Istodax). Depsipeptide has also gained FDA approval for the treatment of peripheral T-cell lymphoma. Many more clinical trials assessing the effects of various HDAC inhibitors on hematological and solid malignancies are being conducted (Ververis et al. 2013). The two approved inhibitors are active against several members of the HDAC family of enzymes leading to acute toxicities such as gastrointestinal symptoms and myelosuppression as well as severe fatigue (Prince et al. 2009). Also, the risk of significant negative impact on cardiac function is considered to be large (Brana & Tabernero 2010). Several reports show that there are intrinsic toxic side effects associated with inhibition of the HDAC class I isoforms and that this prevents the application of broad spectrum and class I selective inhibitors to areas outside of oncology because of a small therapeutic window. Early clinical trials with the selective HDAC6 inhibitor ACY-1215 appear to largely circumvent undesirable side-effects classically reported with broad-acting or class I-selective inhibitors (Raje et al, 2013). Although it remains to be demonstrated in the clinic, compounds that target specific HDACs with greater selectivity may be beneficial in certain cancers (Balasubramanian et al. 2009). For example, the selective HDAC8 inhibitor PCI-34051 was shown to selectively inhibit HDAC8 and induce apoptosis specifically in T-cell lymphomas and not other tumor or normal cells, showing that HDC8 plays an important role in the pathophysiology of this disease and suggesting that therapy with an HDAC8 specific inhibitor may lead to less side effects (Balasubramanian et al. 2008).

The class IIb enzymes, HDAC6 and HDAC10, differ from the other HDACs in that they primarily localize to the cytoplasm and differ structurally by containing two catalytic sites. HDAC6 is a microtubule-associated enzyme and deacetylases primarily non-histone proteins such as α-tubulin, cortactin, and Hsp90 (Aldana-Masangkay & Sakamoto 2011). α-tubulin is involved in cytoskeletal structural integrity and cellular motility, cortactin plays a role in cell motility, while Hsp90 (heat shock protein) is a molecular chaperone helping client proteins to fold properly and maintain function. The therapeutic areas most susceptible to alterations in HDAC6 activity appear to be cancer, autoimmune disorders, and neurodegenerative diseases. In contrast to other HDACs and especially class I isoforms, the loss of function of HDAC6 does not produce toxicity or major developmental defects in rodents (Govindarajan et al. 2013; Morris et al. 2010; Zhang et al. 2008). Inhibition of HDAC6 does not appear to be associated with the same level of toxicity observed with inhibition of the class I isoforms. The lower level of toxicity associated with HDAC6 inhibition compared to inhibition of the HDAC class I isoforms suggest that selective inhibition may provide a way to circumvent toxicity issues and thereby allow a superior side-effect profile and/or a higher dose with an accompanying superior effect on target. This may permit treatment of a wider range of cancer diseases and also treatment of non-oncology diseases requiring a wider therapeutic window (Best & Carey 2010, Zhang et al. 2008).

Cancer

Oncogenes, such as Ras, deregulate fundamental cellular functions, which can lead to the development of tumors and metastases. The Ras/MAPK signaling pathway is known to be required for tumorigenesis and HDAC6 is required for Ras-induced oncogenic transformation by providing anchorage-independent proliferation (Aldana-Masangkay & Sakamoto 2011). This allows the cancer cell to divide freely without being part of a tissue and is a hallmark of malignant transformation. Further, it has been shown that HDAC6 is required for oncogenes to be able to change the spatial organization of the vimentin fibers of the intracellular cytoskeleton which will induce cell stiffness and promote the invasive capacity of cells (Rathje et al. 2014). Thus, HDAC6 activity contributes to cell changes that lead to both tumor formation and invasion of tumor cells into healthy tissue (metastases).

The antitumor effect observed via HDAC6 inhibition is probably the result of multiple mechanisms involving cell motility/migration, invasion, angiogenesis, induction of apoptosis, and inhibition of DNA repair (Kalin & Bergman 2013). HDAC6 knockout mice demonstrated reduced phosphorylation of AKT and ERK1/2 (signaling pathways involved in tumor growth) and lower levels of activated Ras than those derived from wild-type mice (Lee et al. 2008). HDAC6 knock-down cells from SCID mice subcutaneously injected with HDAC6 specific shRNA showed retarded growth. By reconstitution with wild type HDAC6, but not with catalytically inactive mutant HDAC6, these knock-down cells regained its phenotype indicating that HDAC6 is specifically required for tumorigenic growth (Lee et al. 2008). Another method to combat cancer cells is to target the two major pathways for protein turnover in eukaryotic cells—the Ubiquitin-Proteasome-System (UPS) and the HDAC6-dependent lysosomal pathway. HDAC6 directly interacts with misfolded or poly-ubiquinated proteins to target them for lysosome-mediated protein degradation via aggresome formation and autophagy (Aldana-Masangkay & Sakamoto 2011). If UPS activity is insufficient, this HDAC6 dependent pathway is able to compensate for intracellular protein degradation. Cancer cells accumulate more misfolded proteins compared to nonmalignant cells and depend on efficient disposal of these misfolded proteins for cell survival. Thus, simultaneous inhibition of proteasome and HDAC6 activities has been proposed as a strategy to synergistically induce cancer cell death. Successful examples of this approach have used the proteasome inhibitor bortezomib together with different specific HDAC6 inhibitors such as tubacin on multiple myeloma cells (Hideshima et al. 2005), NK84 on ovarian cancer cells (Bazzaro et al. 2008), and ACY-1215 on cells and animal models of multiple myeloma (Santo et al., 2012). In all cases the two inhibitors showed synergistic effects and high selectivity for cancer cells compared to normal cells.

Autoimmune Disorders

There is strong evidence supporting HDAC6 as a target for the treatment of numerous autoimmune disorders (Greer et al. 2012). In murine models, pan-HDAC inhibitors, such as vorinostat and TSA, were able to alleviate the symptoms and reverse the progression of established colitis (de Zoeten et al. 2011). HDAC6 selective inhibitors such as tubacin and tubastatin A but not class I selective HDAC inhibitors such as entinostat were able to confer protection in these in vivo models. In murine models of allograft rejection tubacin and tubastatin A in combination with low-dose rapamycin, a clinically used immunosuppressant, were able to significantly increase the lifespan of mice from approximately 15 days to more than 60 days in comparison to mice treated with rapamycin alone (de Zoeten et al. 2011). This combination therapy was only administered for 14 days but was able to confer long term protection against allograft rejection.

Mental Disorders

In the mammalian brain, HDAC6 is mainly found in neurons (Southwood et al., 2007) and with the highest levels at the dorsal and median raphe nuclei, parts of the brain that are involved in emotional behaviors. HDAC6-deficient mice exhibit antidepressant-like behavior in behavioral tests, and this was mimicked by administration of NCT-14b, a HDAC6-specific inhibitor, to wild type mice (Fukada et al., 2012). Further, selective knockout of the highly abundant HDAC6 in serotonin neurons reduced acute anxiety caused by administration of the steroid hormone corticosterone, and blocked the expression of social deficits in mice exposed to inescapable traumatic stress (Espallergues et al., 2012). Administration of the selective HDAC6 inhibitors ACY-738 and ACY-775 has been shown to induce dramatic increases in $\alpha$-tubulin acetylation in brain and stimulate mouse exploratory behaviors in novel, but not familiar environments (Jochems et al. 2014). The two compounds share the antidepressant-like properties of pan-HDAC inhibitors, such as SAHA and MS-275, in the tail suspension test and social defeat paradigm without any detectable effect on histone acetylation. These effects of ACY-738 and ACY-775 are directly attributable to the inhibition of HDAC6 expressed centrally, as they are fully abrogated in mice with a neural-specific loss of function of HDAC6. Taken together, these findings suggest that HDAC6-mediated reversible acetylation contribute to maintain proper neuronal activity in serotonergic neurons, and also provide a new therapeutic target for depression. In addition, acute stress, via glucocorticoid receptors (GRs), enhances glutamatergic signalling in the prefrontal cortex, a region responsible for high-order cognitive functions. It has been shown (Lee et al. 2012) that inhibition or knockdown of HDAC6 blocks the enhancement of glutamatergic signalling by acute stress and that inhibition or knockdown of the GR chaperone protein Hsp90 (a HDAC6 substrate) produces a similar blockade of the acute stress-induced enhancement of glutamatergic signalling. This suggests that HDAC6 is a key controller of neuronal adaptations to acute stress and that inhibition of HDAC6 may provide neuroprotective effects against stress-induced mental illness.

Neurodegenerative Disorders

There are numerous reports suggesting that HDAC6 inhibition exert neuroprotection which may benefit patients afflicted with neurodegenerative disorders such as Alzheimer's, Parkinson's and Huntington's diseases as well as patients afflicted by traumatic brain injury (TBI) and inherited neurological disorders such as Charcot-Marie-Tooth disease (CMT) and Rett syndrome (Kalin & Bergman 2013, Simoes-Pires et al. 2013). On the other hand, an induction of HDAC6 would theoretically contribute to the degradation of protein aggregates which characterize various neurodegenerative disorders (Simoes-Pires et al. 2013). HDAC6 has been identified as a potential therapeutic target to modulate Alzheimer's disease (AD) pathogenesis. Specific HDAC6 inhibitors exert neuroprotection by increasing the acetylation levels of α-tubulin with subsequent improvement of the axonal transport, which is usually impaired in neurodegenerative disorders such as AD (Simoes-Pires et al. 2013). The loss of proper axonal transport leads to synaptic degradation through impaired mitochondrial and neurotransmitter trafficking (Kalin & Bergman 2013). It has been demonstrated that treatment of neurons with amyloid beta (Aβ) oligomers significantly attenuated mitochondrial elongation and transport, which was subsequently alleviated by treatment with the HDAC6 inhibitor tubastatin A (Kim et al. 2012). In another report, it was shown that reducing endogenous HDAC6 levels in an AD mouse model restored learning and memory (Govindarajan et al. 2013). These results suggest that HDAC6 inhibition may slow or reverse the neuronal damage associated with Aβ and thus represents a viable drug target for the treatment of AD. Further, HDAC6 together with Hsp90 and the ubiquitin ligase CHIP form a network of chaperone complexes that modulates levels of tau—the microtubule-associated protein that is hyperphosphorylated and forms the pathological hallmark of neurofibrillary tangles in AD (Cook & Petrucelli 2013). It has been demonstrated that HDAC6 levels positively correlate with tau burden, while a decrease in HDAC6 activity or expression promotes tau clearance (Cook et al., 2012). Inhibition or depletion of HDAC6 causes Hsp90 hyperacetylation and the concomitant decreased affinity of Hsp90 for client proteins such as tau, leads to client protein degradation (Kalin & Bergman 2013). In addition, loss of HDAC6 activity augments the efficacy of an Hsp90 inhibitor, opening the possibility to synergistically promoting the degradation of Hsp90 client proteins by co-treatments with both HDAC6 and Hsp90 inhibitors, as has been shown for leukemia cells (Cook et al. 2012; Rao et al. 2008; George et al. 2005).

The neuroprotective effect of HDAC6 inhibition may be beneficial for patients suffering from traumatic brain injuries. For example, it has been reported that HDAC6 inhibition results in the hyperacetylation of peroxiredoxin-1 and -2 leading to increased resistance against oxidative stress such as that observed during ischemic stroke (Parmigiani et al. 2008). HDAC6 inhibition may also be beneficial for patients afflicted by inherited neurological disorders such as Charcot-Marie-Tooth disease (CMT) and Rett syndrome. For example, symptomatic improvement was observed in a transgenic mouse model of CMT after the treatment with specific HDAC6 inhibitors, together with the increase in tubulin acetylation (D'Ydewalle et al. 2011). HDAC6 inhibition by tubastatin A has been shown to restore brain-derived neurotropic factor (BDNF) neurological function in Mecp2 knockout hippocampal neurons showing that HDAC6 is a potential target for Rett syndrome (Xu et al. 2014).

The above described data serve to illustrate the validity of modulating HDAC6 activity for treatment of disorders and diseases that include not only hyperproliferative indications, such as cancer, but also other therapeutic areas such as neurodegenerative disorders, autoimmune disorders, and mental disorders.

SUMMARY OF THE INVENTION

A first aspect is a compound of formula (I)

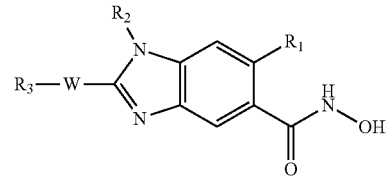

(I)

or a pharmaceutically acceptable salt thereof; wherein
$R_1$ is H or F;
$R_2$ is H or C1-C3 alkyl;
$R_3$ is a moiety of formula (II)

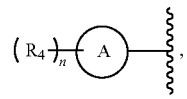

(II)

or $R_3$ is C4-C10 alkyl, or C4-C10 cycloalkyl;
n is an integer of from 0 to 3;
each $R_4$ is independently selected from halogen, C1-C10 alkyl, $R_5O$, $R_6C(O)$, $R_7R_8NX_1$, $R_9C(O)N(R_{10})$, $R_{11}S(O)_2$, $NO_2$, COOH, CN, 5- or 6-membered heteroaryl, and phenyl, said phenyl optionally being substituted with one or more $R_{12}$, and when n is at least 2, two $R_4$ attached to adjacent atoms of ring A may form together a biradical selected from $-Y_1CH_2Y_2-$ and $-Y_1(CH_2)_2Y_2-$, wherein $Y_1$ and $Y_2$ are independently selected from O and $CH_2$;
$R_5$ is selected from H, C1-C6 alkyl, $R_{13}O(CH_2)_2$, $R_{14}R_{15}NX_2CH_2$, and phenyl, said phenyl optionally being substituted with one or more $R_{16}$;
$R_6$ is selected from H, C1-C6 alkyl, and phenyl, said phenyl optionally being substituted with one or more $R_{17}$;
$R_7$ and $R_8$ are independently selected from H and C1-C6 alkyl optionally substituted by $R_{18}O$; or $R_7$ and $R_8$ form, together with the nitrogen to which they are both attached, a 5- or 6-membered heterocyclyl optionally containing one or more further heteroatoms, said heterocyclyl optionally being substituted by one or more C1-C3 alkyl;
$R_9$, $R_{10}$ and $R_{11}$ are independently selected from H and C1-C6 alkyl;
each $R_{12}$ is independently selected from halogen, C1-C6 alkyl, $R_{19}OX_3$, $R_{20}S(O)_2$, $R_{21}R_{22}NX_4$, $R_{23}C(O)$, $R_{24}C(NOH)$, and $R_{25}S(O)_2N(R_{26})$;
$R_{13}$ is selected from H, phenyl, and C1-C6 alkyl, said alkyl optionally being substituted by $R_{27}O$;
$R_{14}$ and $R_{15}$ are independently selected from H and C1-C6 alkyl optionally substituted by $R_{28}O$; or $R_{14}$ and $R_{15}$ form, together with the nitrogen to which they are both attached, a 5- or 6-membered heterocyclyl optionally containing one or more further heteroatoms, said heterocyclyl optionally being substituted by one or more C1-C3 alkyl;
each $R_{16}$ is independently is selected from halogen, C1-C6 alkyl, and $R_{29}O$;
$R_{17}$ is selected from halogen, C1-C6 alkyl, and $R_{30}O$;
$R_{18}$, $R_{19}$ and $R_{20}$ are independently selected from H and C1-C6 alkyl;
$R_{21}$ and $R_{22}$ are independently selected from H and C1-C6 alkyl optionally substituted by $R_{31}O$; or $R_{21}$ and $R_{22}$ form, together with the nitrogen to which they are both attached, a 5- or 6-membered heterocyclyl optionally containing one or more further heteroatoms, said heterocyclyl optionally being substituted by one or more C1-C3 alkyl;

$R_{23}$, $R_{24}$, $R_{25}$, $R_{26}$, $R_{27}$, $R_{28}$, $R_{29}$, $R_{30}$ and $R_{31}$ are independently selected from H and C1-C6 alkyl;

$X_1$, $X_2$, and $X_4$ are independently selected from a direct bond, $CH_2$ and C(O);

$X_3$ is a direct bond or $CH_2$;

ring A is phenyl, naphthyl, or 5- to 10-membered mono- or bicyclic heteroaryl;

W is a direct bond, C1-C3 alkylene, or C2-C3 alkenylene, said alkylene or alkenylene optionally being substituted by one or more C1-C3 alkyl; and any alkyl is optionally substituted with one or more F;

provided that the compound is not N-hydroxy-2-phenyl-1H-benzo[d]imidazole-5-carboxamide.

The compounds of formula (I) are useful in therapy. Therefore, one aspect is a compound of formula (I) for use in therapy.

The compounds of formula (I) are histone deacetylase (HDAC) inhibitors. Therefore, one aspect is a compound of formula (I) for use as an HDAC inhibitor.

The compounds of formula (I) have a selectivity for in particular HDAC6. Therefore, one aspect is a compound of formula (I) for use as a selective HDAC6 inhibitor.

Disorders associated with or mediated by HDAC may be treated by use of the compounds of the invention. One aspect therefore is a method of treatment of a mammal suffering from a disorder associated with or mediated by HDAC, in particular HDAC6.

Another aspect is a pharmaceutical composition comprising the compound of formula (I) and optionally a pharmaceutically acceptable excipient.

Another aspect is a pharmaceutical composition comprising the compound of formula (I) and optionally a pharmaceutically acceptable excipient for use in the treatment of a disorder associated with or mediated by HDAC, in particular HDAC6.

Another aspect is a compound of formula (I) for use in the treatment of a disorder associated with or mediated by HDAC, in particular HDAC6.

Another aspect is a compound of formula (I) for use in the treatment of a disorder selected from autoimmune disorders, mental disorders, neurodegenerative disorders and hyperproliferative disorders, in particular cancers.

DETAILED DESCRIPTION

Definitions

Unless otherwise specified, any term used herein is to be given its conventional meaning. For example, the term alkyl either alone or as part of a radical, includes straight or branched chain alkyl of the general formula $C_nH_{2n+1}$.

The term "C1-C6 alkyl" refers to an alkyl as defined herein above, of the general formula $CH_3$, $C_2H_5$, $C_3H_7$, $C_4H_9$, $C_5H_{11}$ or $C_6H_{13}$.

The term "halogen" refers to F, Cl, Br or I, in particular to F, Cl or Br, more particularly to F and Cl.

The term "hydroxy" refers to a radical of the formula —OH.

The term "alkoxy" refers to a radical of the formula —OR, wherein R is alkyl.

The term "phenoxy" refers to a radical of the formula —OR, wherein R is phenyl.

The term "heteroatom" preferably refers to N, O or S.

The term RC(O) refers to a moiety of formula

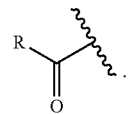

The term RR'N refers to a moiety of formula

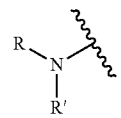

The term RR'NX refers to a moiety of formula

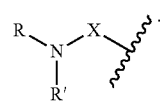

The term RC(O)N(R') refers to a moiety of formula

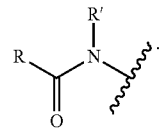

The term $RS(O)_2$ refers to a moiety of formula

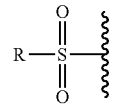

The term $NO_2$ refers to a moiety of formula

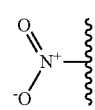

i.e. nitro.

The term COOH refers to a moiety of formula

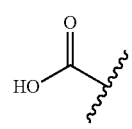

i.e. carboxy.

The term CN refers to a moiety of formula

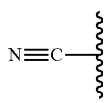

i.e. cyano.

The term "heterocyclcyl" refers to a cyclic non-aromatic moiety containing at least one heteroatom in the ring, such as e.g. pyrrolidinyl, piperidinyl, piperazinyl or morpholinyl.

The term RC(NOH) refers to a moiety of formula

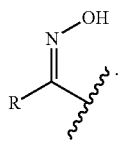

The term "heteroaryl" refers to an aromatic ring containing at least one heteroatom in the ring, e.g. pyridinyl.

The term "bicyclic heteroaryl" refers to a heterocyclic ring comprising 2 aromatic cycles fused to each other, at least one of which contains one or more heteroatoms.

The term "methylenedioxy biradical" refers to a biradical formula —OCH$_2$O—.

The term "ethylenedioxy biradical" refers to a biradical of formula —OCH$_2$CH$_2$O—.

"Optional" or "optionally" means that the subsequently described event or circumstance may but need not occur, and that the description includes instances where the event or circumstance occurs and instances in which it does not.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

The term "excipient" refers to a pharmaceutically acceptable chemical, such as known to those of ordinary skill in the art of pharmacy to aid in the administration of the medicinal agent. It is a compound that is useful in preparing a pharmaceutical composition, generally safe, non-toxic and neither biologically nor otherwise undesirable, and includes excipients that are acceptable for veterinary use as well as human pharmaceutical use. Exemplary excipients include binders, surfactants, diluents, disintegrants, antiadherents, and lubricants.

"Therapeutically effective amount" means an amount of a compound that, when administered to a subject for treating a disease state, is sufficient to effect such treatment for the disease state. The "therapeutically effective amount" will vary depending on the compound, the disease state being treated, the severity of the disease treated, the age and relative health of the subject, the route and form of administration, the judgment of the attending medical or veterinary practitioner, etc.

As used herein the terms "treatment" or "treating" is an approach for obtaining beneficial or desired results including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total) whether detectable or undetectable. The term can also mean prolonging survival as compared to expected survival without the treatment.

The term "mammal" refers to a human or any mammalian animal, e.g. a primate, a farm animal, a pet animal, or a laboratory animal. Examples of such animals are monkeys, cows, sheep, horses, pigs, dogs, cats, rabbits, mice, rats etc. Preferably, the mammal is a human.

The term "hyperproliferative disorder" refers to a disorder involving undesired and uncontrolled cell proliferation. The hyperproliferative disorder may be benign or malignant (cancer). The term "cancer" thus refers to any malignant growth or tumor caused by abnormal and uncontrolled cell division; it may spread to other parts of the body through the lymphatic system or the blood stream and includes both solid tumors and blood-borne tumors. Exemplary cancers include adrenocortical carcinoma, AIDS-related cancers, AIDS-related lymphoma, anal cancer, anorectal cancer, appendix cancer, childhood cerebellar astrocytoma, childhood cerebral astrocytoma, basal cell carcinoma, biliary cancer, extrahepatic bile duct cancer, intrahepatic bile duct cancer, urinary bladder cancer, bone and joint cancer, osteosarcoma and malignant fibrous histiocytoma, brain tumor, brain stem glioma, cerebellar astrocytoma, cerebral astrocytoma/malignant glioma, ependymoma, medulloblastoma, visual pathway and hypothalamic glioma, breast cancer, bronchial adenomas/carcinoids, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Sezary syndrome, endometrial cancer, esophageal cancer, extracranial germ cell tumor, extragonadal germ cell tumor, eye cancer, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin's lymphoma, hypopharyngeal cancer, ocular cancer, Kaposi's sarcoma, renal cancer, laryngeal cancer, acute lymphoblastic leukemia, acute myeloid leukemia, hairy cell leukemia, lip and oral cavity cancer, lung cancer, non-small cell lung cancer, small cell lung cancer, non-Hodgkin's lymphoma, primary central nervous system lymphoma, Waldenstrom's macroglobulinemia, intraocular (eye) melanoma, Merkel cell carcinoma, malignant mesothelioma, metastatic squamous neck cancer, cancer of the tongue, multiple endocrine neoplasia syndrome, myelodysplastic syndromes, myelodysplastic/myeloproliferative diseases, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pheochromocytoma, pineoblastoma and supratentorial primitive neuroectodermal tumors, pituitary tumor, plasma cell neoplasm/multiple myeloma, pleuropulmonary blastoma, prostate cancer, rhabdomyosarcoma, salivary gland cancer, Ewing's sarcoma family of tumors, soft tissue sarcoma, uterine cancer, uterine sarcoma, skin cancer (non-melanoma), skin cancer (melanoma), small intestine cancer, squamous cell carcinoma, testicular cancer, throat cancer, thymoma, thymoma and thymic carcinoma, thyroid cancer, transitional cell cancer of the renal pelvis and ureter and other urinary organs, gestational trophoblastic tumor, urethral cancer, vaginal cancer, vulvar cancer, and Wilm's tumor.

The term "benign hyperproliferative disorder" refers to disorders such as benign tumors, e.g. hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas. Other types of non-malignant hyperproliferative disorders are abnormal cell proliferation due to insults to body tissue during surgery, proliferative responses associated with organ transplantation, abnormal angiogenesis, e.g. abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopaphy, and other ocular angiogenic diseases such as retinopathy of prematurity (retrolental fibroplastic), macular degeneration, corneal graft rejection, neuroscular glaucoma and Oster Webber syndrome, etc.

The term autoimmune disorder (or autoimmune disease) refers to any disorder arising from an inappropriate immune response of the body against substances and tissues normally present in the body (autoimmunity). Such response may be restricted to certain organs or involve a particular tissue in different places. Exemplary autoimmune disorders are acute disseminated encephalomyelitis (ADEM), Addison's disease, agammaglobulinemia, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticarial, autoimmune uveitis, Balo disease/Balo concentric sclerosis, Behçet's disease, Berger's disease, Bickerstaffs encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease (one of two types of idiopathic inflammatory bowel disease "IBD"), Cushing's Syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressive, fibrosing alveolitis (or Idiopathic pulmonary fibrosis), gastritis, gastrointestinal pemphigoid, glomerulonephritis, Goodpasture's syndrome, Graves' disease, Guillain-Barré syndrome (GBS), Hashimoto's encephalopathy, Hashimoto's thyroiditis, Henoch-Schonlein purpura, herpes gestationis (aka gestational pemphigoid), Hidradenitis suppurativa, Hughes-Stovin syndrome, hypogammaglobulinemia, idiopathic inflammatory demyelinating diseases, idiopathic pulmonary fibrosis, idiopathic thrombocytopenic purpura, IgA nephropathy, inclusion body myositis, chronic inflammatory demyelinating polyneuropathy, interstitial cystitis, juvenile idiopathic arthritis (aka juvenile rheumatoid arthritis), Kawasaki's disease, Lambert-Eaton myasthenic syndrome, leukocytoclastic vasculitis, lichen planus, lichen sclerosus, linear IgA disease (LAD), lupoid hepatitis (aka autoimmune hepatitis), lupus erythematosus, Majeed syndrome, Ménière's disease, microscopic polyangiitis, mixed connective tissue disease, morphea, Mucha-Habermann disease (aka pityriasis lichenoides et varioliformis acuta), multiple sclerosis, myasthenia gravis, myositis, narcolepsy, neuromyelitis optica (also Devic's disease), neuromyotonia, occular cicatricial pemphigoid, opsoclonus myoclonus syndrome, Ord's thyroiditis, palindromic rheumatism, PANDAS (pediatric autoimmune neuropsychiatric disorders associated with *streptococcus*), paraneoplastic cerebellar degeneration, paroxysmal nocturnal hemoglobinuria (PNH), Parry Romberg syndrome, Parsonage-Turner syndrome, pars planitis, pemphigus vulgaris, pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, schizophrenia, Schmidt syndrome another form of APS, Schnitzler syndrome, Scleritis, Scleroderma, Serum Sickness, Sjögren's syndrome, spondyloarthropathy, stiff person syndrome, subacute bacterial endocarditis (SBE), Susac's syndrome, Sweet's syndrome, sympathetic ophthalmia, systemic lupus erythematosis, Takayasu's arteritis, temporal arteritis (also known as "giant cell arteritis"), thrombocytopenia, Tolosa-Hunt syndrome, transverse myelitis, ulcerative colitis (one of two types of idiopathic inflammatory bowel disease "IBD"), undifferentiated connective tissue disease different from mixed connective tissue disease, undifferentiated spondyloarthropathy, urticarial vasculitis, vasculitis, vitiligo, and Wegener's granulomatosis.

The term neurogenerative disorder (or neurogenerative disease) refers to disorders associated with a progressive loss of structure or function of neurons affecting the structure or function of the brain, spinal cord or peripheral nervous system. Exemplary neurodegenerative disorders include mitochondrial encephalomyopathies and gut dysmotility syndromes, ataxia syndromes including Friedreich's ataxia and spinocerebellar ataxia (SCA), spinal cord injury, familial and sporadic amyotrophic lateral sclerosis (FALS and ALS, respectively), familial and sporadic Parkinson's disease, familial and sporadic Alzheimer's disease, Huntington's disease, olivopontocerebellar atrophy, multiple system atrophy, progressive supranuclear palsy, diffuse lewy body disease and synucleinopathies, Down Syndrome, corticodentatonigral degeneration, progressive familial myoclonic epilepsy, strionigral degeneration, torsion dystonia, familial tremor, Gilles de la Tourette syndrome, and Hallervorden-Spatz disease.

The term "mental disorder" refers to a disorder as e.g. referred to in the Diagnostic and Statistical Manual of Mental Disorders (DSM) published by American Psychiatric Publishing Inc. (Arlington, Va.). Examples of mental disorders are psychotic disorders and schizophrenia spectrum disorders such as schizotypal (personality) disorder, delusional disorder, brief psychotic disorder, schizophreniform disorder, schizophrenia, schizoaffective disorder, substance/ medication-induced psychotic disorder, and psychotic disorder due to another medical condition; bipolar disorders such as bipolar I disorder, bipolar II disorder, cyclothymic disorder, substance/medication-induced bipolar and related disorder, depressive disorders, such as disruptive mood dysregulation disorder, major depressive disorder, single and recurrent episodes, persistent depressive disorder (dysthymia), premenstrual dysphoric disorder, substance/medication-induced depressive disorder, and depressive disorder due to another medical condition; anxiety disorders, such as separation anxiety disorder, selective mutism, specific phobia, social anxiety disorder (social phobia), panic disorder, agoraphobia, generalized anxiety disorder etc.

The Compound

In a first aspect the present invention relates to a compound of formula (I)

$$(I)$$

or a pharmaceutically acceptable salt thereof, as defined herein.

In a compound of formula (I), $R_1$ is H or F. In some embodiments, $R_1$ is H. In some other embodiments, $R_1$ is F.

The moiety $R_2$ is H or C1-C3 alkyl. In some embodiments, $R_2$ is H or methyl. In some embodiments, $R_2$ is H. In some other embodiments, $R_2$ is C1-C3 alkyl, e.g. $R_2$ is methyl.

In some embodiments, $R_1$ is H, and $R_2$ is H or C1-C3 alkyl, e.g. $R_2$ is H or methyl, or $R_2$ is methyl. In some embodiments, $R_1$ is H, and $R_2$ is C1-C3 alkyl.

In some embodiments, $R_1$ is F, and $R_2$ is H or C1-C3 alkyl, e.g. $R_2$ is H or methyl, in particular $R_2$ is H.

In some other embodiments, $R_1$ is H or F, and $R_2$ is H.

In a compound of formula (I), $R_3$ is a moiety of formula (II)

$$(II)$$

or $R_3$ is C4-C10 alkyl, or C4-C10 cycloalkyl.

In some embodiments, $R_3$ is C4-C10 alkyl, or C4-C10 cycloalkyl.

When $R_3$ is C4-C10 alkyl, it e.g. may be selected from C4-C8 alkyl, e.g. from C4-C6 alkyl, or from C4 alkyl and C5 alkyl, e.g. n-butyl, neopentyl (2,2-dimethylpropyl), or pentan-3-yl.

When $R_3$ is C4-C10 cycloalkyl, it e.g. may be selected from C5-C10 cycloalkyl, or from C5-C8 cycloalkyl, e.g. from C5-C7 cycloalkyl, e.g. $R_3$ may be cyclohexyl. In some embodiments, when $R_3$ is C4-C10 alkyl, or C4-C10 cycloalkyl, it more particularly is C4-C10 alkyl. In some other embodiments, when $R_3$ is C4-C10 alkyl, or C4-C10 cycloalkyl, it more particularly is C4-C10 cycloalkyl. In some embodiments, when $R_3$ is C4-C10 alkyl, or C4-C10 cycloalkyl, the moiety W is a direct bond.

In some embodiments, $R_3$ is a moiety of formula (II)

$$(II)$$

In a moiety of formula (II), ring A is phenyl, naphthyl, or 5- to 10-membered mono- or bicyclic heteroaryl. In some embodiments, ring A is monocyclic, i.e. ring A is phenyl or monocyclic heteroaryl. In some other embodiments, ring A is bicyclic.

In some embodiments, ring A is phenyl or naphthyl. In some embodiments, ring A is phenyl.

In some embodiments, ring A is naphthyl.

In some embodiments, ring A is phenyl or 5- to 10-membered mono- or bicyclic heteroaryl.

In some other embodiments, ring A is 5- to 10-membered mono- or bicyclic heteroaryl.

In some embodiments, ring A is phenyl, naphthyl, or 8- to 10-membered bicyclic heteroaryl, e.g. ring A is phenyl, naphthyl, or 9- to 10-membered bicyclic heteroaryl, or ring A is phenyl, naphthyl, or 9-membered bicyclic heteroaryl.

When ring A is 5- to 10-membered mono- or bicyclic heteroaryl, said heteroaryl e.g. may be 5- to 7-membered monocyclic heteroaryl, or 8- to 10 membered bicyclic heteroaryl, said heteroaryl containing at least one heteroatom selected from N, O, and S, e.g. from N and O.

For example, the heteroaryl may contain 1-5 heteroatoms, or 1-4 heteroatoms, or 1-3 heteroatoms, or 1 or 2 heteroatoms, e.g. 1 heteroatom.

When ring A is monocyclic heteroaryl, it more particularly may be 5- to 6-membered monocyclic heteroaryl containing 1-4 heteroatoms. In some embodiments, ring A is 5-membered monocyclic heteroaryl. In some other embodiments, ring A is 6-membered monocyclic heteroaryl. For example, the monocyclic heteroaryl may be selected from moieties such as 1H-pyrrolyl, furyl, thienyl, 1H-imidazolyl, thiazolyl, 1H-tetrazolyl, and pyridyl.

In some embodiments, when ring A is monocyclic heteroaryl, the monocyclic heteroaryl is selected from and In some embodiments, when ring A is monocyclic heteroaryl, the monocyclic heteroaryl is selected from

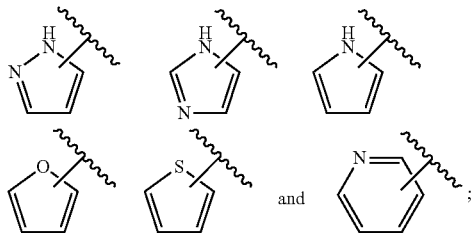

e.g from

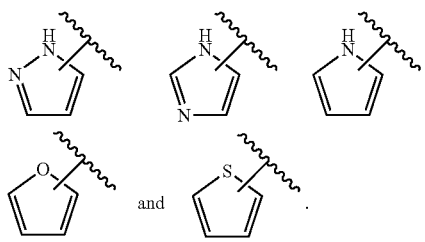

In some embodiments, when ring A is monocyclic heteroaryl, the monocyclic ring is selected from

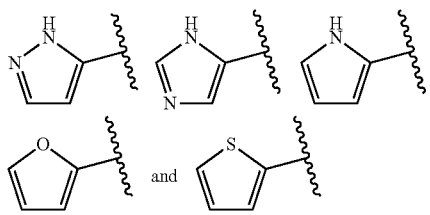

When ring A is bicyclic heteroaryl, it more particularly may 9- or 10-membered bicyclic heteroaryl, containing 1 to 5 heteroatoms. In some embodiments, ring A is 9-membered bicyclic heteroaryl. In some other embodiments, ring A is 10-membered bicyclic heteroaryl.

For example, the bicyclic heteroaryl may be selected from 1H-indolyl, benzofuryl, and quinolyl.

In some embodiments, the bicyclic heteroaryl is comprised of a benzene ring fused to a 5- or 6-membered heteroaryl. In some embodiments, the bicyclic heteroaryl is comprised of a benzene ring fused to a 5- or 6-membered heteroaryl containing a nitrogen and/or oxygen atom in the ring, e.g. a heteroaryl containing one heteroatom, said heteroatom being selected from N and O. In some embodiments, the bicyclic heteroaryl is comprised of a benzene ring fused to a 5- or 6-membered heteroaryl containing one heteroatom, which heteroatom is N. In some embodiments, the bicyclic heteroaryl is comprised of a benzene ring fused to a 5- or 6-membered heteroaryl containing one heteroatom, which heteroatom is O.

In some embodiments, ring A is a bicyclic heteroaryl comprised of a benzene ring fused to a 5-membered heteroaryl, e.g. containing 1 or 2 heteroatoms in the ring, such as one N or one O, e.g. one N.

In some embodiments, ring A is a bicyclic heteroaryl comprised of a benzene ring fused to a 6-membered heteroaryl, e.g. containing 1 or 2 heteroatoms in the ring, such as one N or one O, e.g. one N.

In some embodiments, the bicyclic heteroaryl is selected from

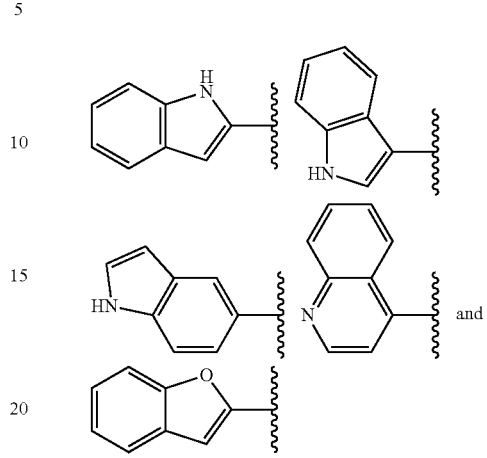

In some embodiments, the bicyclic heteroaryl is selected from

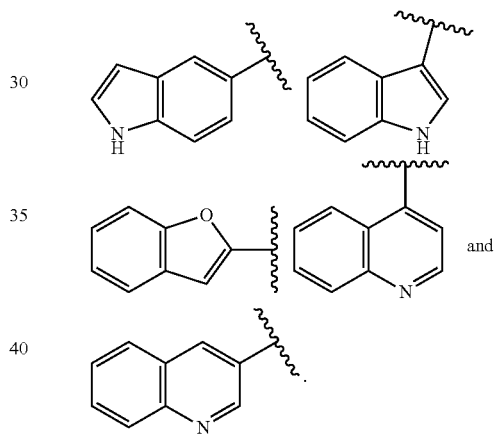

Ring A is unsubstituted, i.e. n is 0, or substituted with 1, 2 or 3 moieties $R_4$. In some embodiments, e.g. when ring A is heteroaryl, in particular when ring A is monocyclic heteroaryl, ring A is unsubstituted. In other embodiments, ring A is substituted with at least one $R_4$, i.e. n is 1, 2, or 3. In some embodiments, n is 1 or 2, e.g. n is 1. In some other embodiments, n is 2. In still other embodiments, n is 2 or 3, e.g. n is 3.

As noted herein above, in some embodiments, ring A is phenyl or naphthyl. In some embodiments, when ring A is phenyl or naphthyl, in particular when ring A is phenyl, n is 1, 2 or 3, e.g. n is 1 and 2, or n is 1.

Each moiety $R_4$, is independently selected from halogen, C1-C10 alkyl, $R_5O$, $R_6C(O)$, $R_7R_8NX_1$, $R_9C(O)N(R_{10})$, $R_{11}S(O)_2$, $NO_2$, COOH, CN, 5- or 6-membered heteroaryl, and phenyl, said phenyl optionally being substituted with one or more $R_{12}$; and when n is at least 2, two $R_4$ attached to adjacent atoms of ring A may form together a biradical selected from $-Y_1CH_2Y_2-$ and $-Y_1(CH_2)_2Y_2-$, wherein $Y_1$ and $Y_2$ are independently selected from O and $CH_2$.

In some embodiments, each $R_4$ is independently selected from halogen, C1-C10 alkyl, $R_5O$, $R_7R_8NX_1$, $R_9C(O)N$ ($R_{10}$), $R_{11}S(O)_2$, $NO_2$, CN, 5- or 6-membered heteroaryl, and phenyl, said phenyl optionally being substituted with one or more $R_{12}$; and when n is at least 2, two $R_4$ attached to adjacent atoms of ring A may form together a biradical selected from —$Y_1CH_2Y_2$— and —$Y_1(CH_2)_2Y_2$—, wherein $Y_1$ and $Y_2$ are independently selected from O and $CH_2$.

In some embodiments, each $R_4$ is independently selected from halogen, C1-C6 alkyl, $R_5O$, $R_6C(O)$, $R_7R_8NX_1$, $R_9C(O)N(R_{10})$, $NO_2$, COOH, CN, and phenyl, optionally substituted by one or more $R_{12}$; and when n is at least 2, two $R_4$, attached to adjacent atoms of the ring A may form together a biradical selected from —$Y_1CH_2Y_2$— and —$Y_1(CH_2)_2Y_2$—; wherein $Y_1$ and $Y_2$ are independently selected from O and $CH_2$.

In some embodiments, each $R_4$ is independently selected from halogen, C1-C6 alkyl, $R_5O$, $R_6C(O)$, $R_7R_8NX_1$, $R_9C(O)N(R_{10})$, $NO_2$, CN, and phenyl, optionally substituted by one or more $R_{12}$; and when n is at least 2, two $R_4$, attached to adjacent atoms of the ring A, may form together a biradical selected from —$Y_1CH_2Y_2$— and —$Y_1(CH_2)_2Y_2$—, wherein $Y_1$ and $Y_2$ are independently selected from O and $CH_2$.

In some other embodiments, each $R_4$ is independently selected from halogen, C1-C6 alkyl, $R_5O$, $R_6C(O)$, $R_7R_8NX_1$, $R_9C(O)N(R_{10})$, COOH, CN, and phenyl, optionally substituted by one or more $R_{12}$; and when n is at least 2, two $R_4$, attached to adjacent atoms of the ring A, may form together a biradical selected from —$Y_1CH_2Y_2$— and —$Y_1(CH_2)_2Y_2$—, wherein $Y_1$ and $Y_2$ are independently selected from O and $CH_2$.

In some embodiments, each $R_4$ is independently selected from halogen, C1-C6 alkyl, $R_5O$, $R_6C(O)$, $R_7R_8NX_1$, $R_9C(O)N(R_{10})$, CN, and phenyl, optionally substituted by one or more $R_{12}$; and when n is at least 2, two $R_4$, attached to adjacent atoms of the ring A, may form together a biradical selected from —$Y_1CH_2Y_2$— and —$Y_1(CH_2)_2Y_2$—, wherein $Y_1$ and $Y_2$ are independently selected from O and $CH_2$.

In some embodiments, each $R_4$ is independently selected from halogen, C1-C6 alkyl, $R_5O$, and phenyl, optionally substituted by one or more $R_{12}$; and when n is at least 2, two $R_4$, attached to adjacent atoms of the ring A, may form together a biradical selected from —$Y_1CH_2Y_2$— and —$Y_1(CH_2)_2Y_2$—, wherein $Y_1$ and $Y_2$ are independently selected from O and $CH_2$.

In some embodiments, each $R_4$ is independently selected from halogen, C1-C6 alkyl, $R_5O$, $R_6C(O)$, $R_7R_8NX_1$, $R_9C(O)N(R_{10})$, $NO_2$, COOH, CN, and phenyl, optionally substituted by one or more $R_{12}$.

In some embodiments, each $R_4$ is independently selected from halogen, C1-C6 alkyl, $R_5O$, $R_6C(O)$, $R_7R_8NX_1$, $R_9C(O)N(R_{10})$, $NO_2$, CN, and phenyl, optionally substituted by one or more $R_{12}$.

In some other embodiments, each $R_4$ is independently selected from halogen, C1-C6 alkyl, $R_5O$, $R_6C(O)$, $R_7R_8NX_1$, $R_9C(O)N(R_{10})$, COOH, CN, and phenyl, optionally substituted by one or more $R_{12}$.

In some embodiments, each $R_4$ is independently selected from halogen, C1-C6 alkyl, $R_5O$, $R_6C(O)$, $R_7R_8NX_1$, $R_9C(O)N(R_{10})$, CN, and phenyl, optionally substituted by one or more $R_{12}$.

In some embodiments, each $R_4$ is independently selected from halogen, C1-C6 alkyl, $R_5O$, and phenyl, optionally substituted by one or more $R_{12}$.

In some embodiments, each $R_4$ is independently selected from halogen, C1-C6 alkyl and $R_5O$.

In some embodiments, each $R_4$ is independently selected from halogen and C1-C6 alkyl.

In some embodiments, each $R_4$ is independently selected from halogen, $R_5O$, and phenyl, optionally substituted by one or more $R_{12}$.

In some embodiments, each $R_4$ is independently selected from halogen, $R_5O$, and phenyl, optionally substituted by one or more $R_{12}$.

In some embodiments, each $R_4$ is independently selected from halogen, C1-C6 alkyl, and phenyl, optionally substituted by one or more $R_{12}$.

In some embodiments, each $R_4$ is independently selected from $R_5O$, and phenyl, optionally substituted by one or more $R_{12}$.

In some embodiments, when n is 1, 2 or 3, e.g. n is 1 or 2, or n is 1, one $R_4$ is phenoxy, optionally substituted with one or more $R_{16}$, phenyl, optionally substituted by one or more $R_{12}$, or 5- or 6-membered heteroaryl, and any further $R_4$ is as defined herein, but preferably is not phenyl, phenoxy or heteroaryl.

In some embodiments, when n is 1, 2 or 3, e.g. n is 1 or 2, or n is 1, one $R_4$ is phenyl, optionally substituted by one or more $R_{12}$, or 5- or 6-membered heteroaryl, and any further $R_4$ is as defined herein, but preferably is not phenyl, phenoxy or heteroaryl.

In some embodiments, when n is 1, 2 or 3, e.g. n is 1 or 2, or n is 1, one $R_4$ is phenoxy, optionally substituted with one or more $R_{16}$, or phenyl, optionally substituted by one or more $R_{12}$, and any further $R_4$ is as defined herein, but preferably is not phenyl, phenoxy or heteroaryl.

In some embodiments, when n is 1, 2 or 3, e.g. n is 1 or 2, or n is 1, one $R_4$ is phenoxy, optionally substituted with one or more $R_{16}$, or phenyl, optionally substituted by one or more $R_{12}$, and any further $R_4$ is as defined herein, but preferably is not phenyl, phenoxy or heteroaryl.

In some embodiments, when n is 1, 2 or 3, e.g. n is 1 or 2, or n is 1, one $R_4$ is phenoxy, optionally substituted with one or more $R_{16}$, and any further $R_4$ is as defined herein, but preferably is not phenyl, phenoxy or heteroaryl.

In some embodiments, when n is 1, 2 or 3, e.g. n is 1 or 2, or n is 1, one $R_4$ is phenyl, optionally substituted with one or more $R_{12}$, and any further $R_4$ is as defined herein, but preferably is not phenyl, phenoxy or heteroaryl.

In some embodiments, at least one $R_4$ is phenyl, optionally substituted by one or more $R_{12}$, and optionally ring A is also substituted by 1 or 2 further $R_4$, as defined herein above, in particular 1 or 2 $R_4$ independently selected from halogen, C1-C6 alkyl, $R_5O$—, $R_6C(O)$, $R_7R_8NX_1$, $R_9C(O)N(R_{10})$, $NO_2$, COOH, and CN; from halogen, C1-C6 alkyl, $R_5O$—, $R_6C(O)$, $R_7R_8NX_1$, $R_9C(O)N(R_{10})$, $NO_2$, and CN; from halogen, C1-C6 alkyl, $R_5O$—, $R_6C(O)$—, $R_7R_8NX_1$, $R_9C(O)N(R_{10})$, COOH, and CN; from halogen, C1-C6 alkyl, $R_5O$—, $R_6C(O)$—, $R_7R_8NX_1$, $R_9C(O)N(R_{10})$, and CN; or from halogen, C1-C6 alkyl, and $R_5O$, or both are H; wherein $R_5$ and $R_6$ are as defined herein, and are both preferably selected from H and C1-C6 alkyl.

In some embodiments, when n is 2 or 3, two $R_4$ attached to adjacent atoms of the ring A form together a biradical selected from —$Y_1CH_2Y_2$— and —$Y_1(CH_2)_2Y_2$—, wherein $Y_1$ and $Y_2$ are independently selected from O and $CH_2$. In some of these embodiments, n is 2, i.e. no further $R_4$ is present. In some other embodiments, n is 3.

In some embodiments, when two $R_4$, attached to adjacent atoms of the ring A, form together a biradical selected from —$Y_1CH_2Y_2$— and —$Y_1(CH_2)_2Y_2$—, said biradical is methylenedioxy, ethyleneoxy or etheylenedioxy, e.g. methylenedioxy or etheylenedioxy.

In some embodiments, when two $R_4$ form together a methylenedioxy or etheylenedioxy biradical, such biradical is a methylenedioxy biradical. In some other embodiments, the biradical is an etheylenedioxy biradical.

When one or more of $R_4$ is C1-C6 alkyl, said alkyl e.g. may be C1-C4 alkyl, or C1-C3 alkyl, such as C1-C2 alkyl, in particular methyl.

When $R_4$ is phenyl, optionally substituted by one or more $R_{12}$, said phenyl e.g. is optionally substituted by 1, 2 or 3 $R_{12}$, e.g. 1 or 2 $R_{12}$, e.g. 1 $R_{12}$.

In some particular embodiments of a compound of formula (I), each $R_4$ is independently selected from F, Cl, Br, $CH_3$, $CF_3$, phenyl, phenoxy, $CH_3O$, $CHF_2O$ and OH.

In some other particular embodiments, one $R_4$ is independently selected from phenyl and phenoxy, and optionally ring A is substituted with one or two further $R_4$ independently selected from F, Cl, Br, $CH_3$, $CF_3$, phenyl, phenoxy, $CH_3O$, $CHF_2O$ and OH; or from F, Cl, Br, $CH_3$, $CF_3$, $CH_3O$, $CHF_2O$ and OH, e.g. F.

It should be noted that when ring A is heteroaryl, any $R_4$ may be attached to any ring member of said heteroaryl (carbon or heteroatom, such as N) having an available valence.

When $R_4$ is $R_5O$, $R_5$ is selected from H, C1-C6 alkyl, $R_{13}O(CH_2)_2$, $R_{14}R_{15}NX_2CH_2$, and phenyl, said phenyl optionally being substituted with one or more $R_{16}$.

In some embodiments, $R_5$ is selected from H, C1-C6 alkyl and phenyl, e.g. from H, C1-C4 alkyl and phenyl, or from H, C1-C3 alkyl and phenyl, such as from H, C1-C2 alkyl and phenyl, or from H, methyl and phenyl, e.g. $R_5$ is phenyl, wherein said phenyl is optionally substituted by one or more $R_{16}$.

When $R_5$ is phenyl, optionally substituted by one or more $R_{16}$, said phenyl e.g. is optionally substituted by 1, 2 or 3 $R_{16}$, e.g. 1 or 2 $R_{16}$, e.g. 1 $R_{16}$.

In some embodiments, when $R_5$ is phenyl, said phenyl is unsubstituted or substituted by one $R_{16}$.

In some embodiments, when $R_5$ is phenyl, said phenyl is unsubstituted.

In some embodiments, $R_5$ is selected from H and C1-C6 alkyl.

When $R_5$ is selected from H and C1-C6 alkyl, it more particularly may be selected from H and C1-C4 alkyl, or from H and C1-C3 alkyl, or from H and C1-C2 alkyl, or from H and methyl, e.g. $R_5$ is H.

Thus, in some embodiments, $R_5$ is H. In some other embodiments, $R_5$ is as defined herein above, but is different from H.

In some embodiments, $R_5$ is $R_{13}O(CH_2)_2$ or $R_{14}R_{15}NX_2CH_2$. In some embodiments, $R_5$ is $R_{13}O(CH_2)_2$. In some embodiments, $R_5$ is $R_{14}R_{15}NX_2CH_2$.

In some embodiments, $R_5$ is selected from $R_{13}O(CH_2)_2$, $R_{14}R_{15}NX_2CH_2$, and phenyl, e.g. from $R_{13}O(CH_2)_2$ and phenyl.

When $R_4$ is $R_6C(O)$, $R_6$ is selected from H, C1-C6 alkyl and phenyl, e.g. from H, C1-C4 alkyl and phenyl, optionally substituted by one or more $R_{17}$, or from H, C1-C3 alkyl and phenyl, or from H, C1-C2 alkyl and phenyl, or from H, methyl and phenyl, e.g. $R_6$ is phenyl, wherein the phenyl is optionally substituted with one or more $R_{17}$.

When $R_6$ is phenyl, optionally substituted with one or more $R_{17}$, said phenyl e.g. is optionally substituted with 1, 2 or 3 $R_{17}$, e.g. 1 or 2 $R_{17}$, e.g. 1 $R_{17}$. In some embodiments, when $R_6$ is phenyl, said phenyl is unsubstituted.

When $R_4$ is $R_7R_8NX_1$, $R_7$ and $R_8$ are independently selected from H and C1-C6 alkyl optionally substituted by $R_{18}O$; or $R_7$ and $R_8$ form, together with the nitrogen to which they are both attached, a 5- or 6-membered heterocyclyl optionally containing one or more further heteroatoms, said heterocyclyl optionally being substituted by one or more C1-C3 alkyl; and $X_1$ is a direct bond, $CH_2$ or C(O).

In some embodiments, $R_7$ and $R_8$ are independently selected from H and C1-C6 alkyl, e.g. H and C1-C4 alkyl, or H and C1-C3 alkyl, wherein the alkyl is optionally substituted by $R_{18}O$; or $R_7$ and $R_8$ form, together with the nitrogen to which they are both attached, a 5- or 6-membered heterocyclyl optionally containing one or more further heteroatoms, said heterocyclyl optionally being substituted by one or more C1-C3 alkyl.

In some embodiments, $R_7$ and $R_8$ are independently selected from H and C1-C6 alkyl. In some embodiments, $R_7$ and $R_8$ are independently selected from H and C1-C4 alkyl, or from H and C1-C3 alkyl, in particular from H, methyl and ethyl. In some embodiments, $R_7$ and $R_8$ are as defined herein above, but one of $R_7$ and $R_8$ is different from H. In some embodiments, $R_7$ and $R_8$ are as defined herein above, but both are different from H.

In some embodiments, $R_7$ and $R_8$ are identical with each other; e.g. $R_7R_8N$ is amino ($NH_2$), dimethylamino (($CH_3$)$_2N$) or diethylamino (($CH_3CH_2$)$_2N$).

In some embodiments, $R_7$ and $R_8$ form, together with the nitrogen to which they are both attached, a 5- or 6-membered heterocyclyl optionally containing one or more further heteroatoms, e.g. one further heteroatom, said heterocyclyl optionally being substituted by one or more C1-C3 alkyl. In such heterocyclyl, any further heteroatom e.g. may be selected from N and O.

In some embodiments, $R_7$ and $R_8$ form, together with the nitrogen to which they are both attached, a 6-membered heterocyclyl optionally containing one or more further heteroatoms, e.g. one further heteroatom, said heterocyclyl optionally being substituted by one or more C1-C3 alkyl. In such heterocyclyl, any further heteroatom e.g. may be selected from N and O. For example, in some embodiments, $R_7R_8N$ is selected from piperidinyl, piperazinyl and morpholinyl, optionally substituted by one or more C1-C3 alkyl.

In the moiety $R_7R_8NX_1$, $X_1$ is a direct bond, $CH_2$ or C(O). In some embodiments, $X_1$ is a direct bond or $CH_2$. In some embodiments, $X_1$ is a direct bond. In some embodiments, $X_1$ is $CH_2$. In some embodiments, $X_1$ is $CH_2$ or C(O). In some embodiments, $X_1$ is C(O).

When $R_4$ is $R_9C(O)N(R_{10})$, $R_9$ and $R_{10}$ are independently selected from H and C1-C6 alkyl. In some embodiments, $R_9$ and $R_{10}$ are independently selected from H and C1-C4 alkyl, or from H and C1-C3 alkyl, or from H and C1-C2 alkyl, in particular from H and methyl.

In some embodiments, $R_{10}$ is as defined herein above, and $R_9$ is selected from H and C1-C4 alkyl, or from H and C1-C3 alkyl, or from H and C1-C2 alkyl, in particular from H and methyl.

In some embodiments, $R_9$ is as defined herein above, and $R_{10}$ is selected from H and C1-C4 alkyl, or from H and C1-C3 alkyl, or from H and C1-C2 alkyl, in particular from H and methyl, e.g. $R_{10}$ is H.

In some embodiments, $R_9$ and $R_{10}$ are as defined herein above, but at least one is different from H, e.g. $R_9$ is different from H. Thus, in some embodiments, $R_{10}$ is H, and $R_9$ is selected from C1-C4 alkyl, or from C1-C3 alkyl, or from C1-C2 alkyl, in particular $R_9$ is methyl.

In some other embodiments, $R_9$ and $R_{10}$ are as defined herein above, $R_{10}$ is different from H. In some embodiments, $R_9$ is H, and $R_{10}$ is selected from C1-C4 alkyl, or from C1-C3 alkyl, or from C1-C2 alkyl, in particular $R_{10}$ is methyl.

When $R_4$ is $R_{11}S(O)_2$, $R_{11}$ is selected from H and C1-C6 alkyl. In some embodiments, $R_{11}$ is selected from H and C1-C4 alkyl, or from H and C1-C3 alkyl, or from H and C1-C2 alkyl, in particular from H and methyl, e.g. $R_{11}$ is methyl. In some embodiments, $R_{11}$ is C1-C6 alkyl, or C1-C4 alkyl, or C1-C3 alkyl, or C1-C2 alkyl.

When $R_4$ is phenyl substituted by at least one $R_{12}$, the moiety $R_{12}$ is selected from halogen, C1-C6 alkyl, $R_{19}OX_3$, $R_{20}S(O)_2$, $R_{21}R_{22}NX_4$, $R_{23}C(O)$, $R_{24}C(NOH)$, and $R_{25}S(O)_2 N(R_{26})$.

In some embodiments, each $R_{12}$ is independently selected from halogen, C1-C6 alkyl, $R_{19}OX_3$, $R_{20}S(O)_2$, $R_{21}R_{22}NX_4$, and $R_{25}S(O)_2N(R_{26})$; or from halogen, C1-C6 alkyl, $R_{19}OX_3$, $R_{20}S(O)_2$, and $R_{21}R_{22}NX_4$, e.g. from halogen, C1-C6 alkyl, $R_{19}OX_3$, and $R_{21}R_{22}NX_4$, such as from halogen, $R_{19}OX_3$, and $R_{21}R_{22}NX_4$. In some embodiments, $R_{12}$ is $R_{21}R_{22}NX_4$.

In some embodiments, each $R_{12}$ is independently selected from halogen and C1-C6 alkyl, e.g. each $R_{12}$ is halogen. In some other embodiments, each $R_{12}$ is independently selected from halogen and $R_{19}OX_3$, e.g. each $R_{12}$ is $R_{19}OX_3$. In still other embodiments, each $R_{12}$ is independently selected from C1-C6 alkyl and $R_{19}OX_3$, e.g. each $R_{12}$ is C1-C6 alkyl. In some embodiments, when $R_4$ is phenyl, said phenyl is unsubstituted.

When $R_{12}$ is C1-C6 alkyl, it more particularly may be C1-C4 alkyl, or C1-C3 alkyl, or C1-C2 alkyl, or methyl. As noted herein, any alkyl in a compound of formula (I) may optionally be substituted by one or more F. In particular, when $R_{12}$ is C1-C6 alkyl, said alkyl preferably is substituted by one or more F. In some embodiments, when $R_{12}$ is C1-C6 alkyl, optionally substituted by one or more F, said alkyl is $CF_3$.

In the moiety $R_{13}O(CH_2)_2$, $R_{13}$ is selected from H, phenyl, and C1-C6 alkyl, e.g. C1-C4 alkyl, or C1-C3 alkyl, said alkyl optionally being substituted by a moiety $R_{27}O$. In some embodiments, $R_{13}$ is selected from phenyl and C1-C6 alkyl, said alkyl optionally being substituted by a moiety $R_{27}O$. In some embodiments, $R_{13}$ is phenyl. In some other embodiments, $R_{12}$ is C1-C6 alkyl, said alkyl optionally being substituted by a moiety $R_{27}O$.

When $R_{13}$ C1-C6 alkyl, optionally substituted by $R_{27}O$, $R_{13}$ more particularly may be a moiety of formula $R_{27}O(CH_2)_2$.

In the moiety $R_{14}R_{15}NX_2CH_2$, $R_{14}$ and $R_{15}$ are independently selected from H and C1-C6 alkyl optionally substituted by $R_{28}O$; or $R_{14}$ and $R_{15}$ form, together with the nitrogen to which they are both attached, a 5- or 6-membered heterocyclyl optionally containing one or more further heteroatoms, said heterocyclyl optionally being substituted by one or more C1-C3 alkyl; and $X_2$ is selected from a direct bond, $CH_2$ and $C(O)$.

In some embodiments, $R_{14}$ and $R_{15}$ are independently selected from C1-C6 alkyl optionally substituted by $R_{28}O$; or $R_{14}$ and $R_{15}$ form, together with the nitrogen to which they are both attached, a 5- or 6-membered heterocyclyl optionally containing one or more further heteroatoms, said heterocyclyl optionally being substituted by one or more C1-C3 alkyl.

In some embodiments, $R_{14}$ and $R_{15}$ are independently selected from H and C1-C6 alkyl optionally substituted by $R_{28}O$.

When either $R_{14}$ or $R_{15}$, or both $R_{14}$ and $R_{15}$, are C1-C6 alkyl optionally substituted by $R_{28}O$, said alkyl e.g. may be C1-C4 alkyl, or C1-C3 alkyl, or C1-C2 alkyl.

In some other embodiments, $R_{14}$ and $R_{15}$ form, together with the nitrogen to which they are both attached, a 5- or 6-membered heterocyclyl optionally containing one or more further heteroatoms, said heterocyclyl optionally being substituted by one or more C1-C3 alkyl. In such heterocyclyl, any further heteroatom e.g. may be selected from N and O. For example, in some embodiments, the heterocyclyl is selected from pyrrolidinyl, piperidinyl, piperazinyl and morpholinyl.

The moiety $R_{16}$ is selected from halogen, C1-C6 alkyl, e.g. C1-C4 alkyl, and $R_{29}O$. In some embodiments, $R_{16}$ is selected from C1-C6 alkyl, e.g. C1-C4 alkyl and $R_{29}O$. In some embodiments, $R_{16}$ is C1-C6 alkyl, e.g. C1-C4 alkyl. In some other embodiments, $R_{16}$ is $R_{29}O$.

The moiety $R_{17}$ is selected from halogen, C1-C6 alkyl, e.g. C1-C4 alkyl, and $R_{30}O$. In some embodiments, $R_{17}$ is selected from C1-C6 alkyl, e.g. C1-C4 alkyl and $R_{29}O$. In some embodiments, $R_{17}$ is C1-C6 alkyl, e.g. C1-C4 alkyl. In some other embodiments, $R_{17}$ is $R_{30}O$.

The moieties $R_{18}$, $R_{19}$, $R_{20}$, $R_{23}$, $R_{24}$, $R_{25}$, $R_{26}$, $R_{27}$, $R_{28}$, $R_{29}$, $R_{30}$ and $R_{31}$ are all independently selected from H and C1-C6 alkyl, e.g. from H and C1-C4 alkyl, or from H and C1-C3 alkyl, for example H and methyl.

The moiety $R_{18}$ is selected from H and C1-C6 alkyl, e.g. from H and C1-C4 alkyl, or from H and C1-C3 alkyl, for example H and methyl. In some embodiments, $R_{18}$ is C1-C6 alkyl, e.g. C1-C4 alkyl, or C1-C3 alkyl, for example methyl.

In the moiety $R_{19}OX_3$, $R_{19}$ is H or C1-C6 alkyl, e.g. H or C1-C4 alkyl, such as H or C1-C3 alkyl, e.g. H or C1-C2 alkyl, in particular H or methyl, e.g. $R_{19}$ is H; and $X_3$ is a direct bond or $CH_2$.

The moiety $R_{20}$ is selected from H and C1-C6 alkyl, e.g. from H and C1-C4 alkyl, or from H and C1-C3 alkyl, for example from H and methyl. In some embodiments, $R_{18}$ is C1-C6 alkyl, e.g. C1-C4 alkyl, or C1-C3 alkyl, for example methyl.

In the moiety $R_{21}R_{22}NX_4$, $R_{21}$ and $R_{22}$ are independently selected from H and C1-C6 alkyl optionally substituted by $R_{31}O$; or $R_{21}$ and $R_{22}$ form, together with the nitrogen to which they are both attached, a 5- or 6-membered heterocyclyl optionally containing one or more further heteroatoms, said heterocyclyl optionally being substituted by one or more C1-C3 alkyl; and $X_4$ is a direct bond, $CH_2$ or $C(O)$.

In some embodiments, $R_{21}$ and $R_{22}$ are independently selected from C1-C6 alkyl optionally substituted by $R_{31}O$; or $R_{21}$ and $R_{22}$ form, together with the nitrogen to which they are both attached, a 5- or 6-membered heterocyclyl optionally containing one or more further heteroatoms, said heterocyclyl optionally being substituted by one or more C1-C3 alkyl.

In some embodiments, $R_{21}$ and $R_{22}$ are independently selected from H and C1-C6 alkyl, optionally substituted by $R_{31}O$.

When either $R_{21}$ or $R_{22}$, or both $R_{21}$ and $R_{22}$, are C1-C6 alkyl optionally substituted by $R_{31}O$, said alkyl e.g. may be C1-C4 alkyl, or C1-C3 alkyl, or C1-C2 alkyl.

In some other embodiments, $R_{21}$ and $R_{22}$ form, together with the nitrogen to which they are both attached, a 5- or 6-membered heterocyclyl optionally containing one or more further heteroatoms, said heterocyclyl optionally being substituted by one or more C1-C3 alkyl.

In such heterocyclyl, any further heteroatom e.g. may be selected from N and O. For example, in some embodiments, the heterocyclyl is selected from pyrrolidinyl, piperidinyl, piperazinyl and morpholinyl.

In the moiety $R_{21}R_{22}NX_4$, $X_4$ is a direct bond, $CH_2$ or $C(O)$. In some embodiments, $X_4$ is a direct bond or $CH_2$. In some embodiments, X is $CH_2$. In some other embodiments, $X_4$ is $CH_2$ or $C(O)$, e.g. $X_4$ is $C(O)$.

In the moiety $R_{23}C(O)$, $R_{23}$ is H or C1-C6 alkyl, e.g. H or C1-C4 alkyl, such as H or C1-C3 alkyl, e.g. H or C1-C2 alkyl, in particular H or methyl, e.g. $R_{23}$ is H.

In the moiety $R_{24}C(NOH)$, $R_{24}$ is H or C1-C6 alkyl, e.g. H or C1-C4 alkyl, such as H or C1-C3 alkyl, e.g. H or C1-C2 alkyl, in particular H or methyl, e.g. $R_{24}$ is H.

In the moiety $R_{25}S(O)_2N(R_{26})$, $R_{25}$ and $R_{26}$ are independently selected from H and C1-C6 alkyl, e.g. from H and C1-C4 alkyl, or from H and C1-C3 alkyl, for example from H and methyl. In some embodiments, $R_{25}$ is C1-C6 alkyl, e.g. C1-C4 alkyl, or C1-C3 alkyl, for example methyl; and $R_{26}$ is H or C1-C6 alkyl, e.g. H or C1-C4 alkyl, such as H or C1-C3 alkyl, e.g. H or C1-C2 alkyl, in particular H or methyl, e.g. $R_{26}$ is H.

In the moiety $R_{27}O$, $R_{27}$ is H or C1-C6 alkyl, e.g. H or C1-C4 alkyl, or H or C1-C3 alkyl, for example H or methyl. In some embodiments, $R_{27}$ is C1-C6 alkyl, e.g. C1-C4 alkyl, or C1-C3 alkyl, for example methyl.

In the moiety $R_{28}O$, $R_{28}$ is selected from H and C1-C6 alkyl, e.g. from H and C1-C4 alkyl, or from H and C1-C3 alkyl, for example H and methyl. In some embodiments, $R_{28}$ is C1-C6 alkyl, e.g. C1-C4 alkyl, or C1-C3 alkyl, for example methyl.

In the moiety $R_{29}O$, $R_{29}$ is selected from H and C1-C6 alkyl, e.g. from H and C1-C4 alkyl, or from H and C1-C3 alkyl, or from H and C1-C2 alkyl, or from H and methyl, e.g. $R_{29}$ is H. In some embodiments, $R_{29}$ is selected from C1-C6 alkyl, e.g. from C1-C4 alkyl, or from C1-C3 alkyl, or from C1-C2 alkyl, e.g. $R_{29}$ is methyl.

In the moiety $R_{30}O$, $R_{30}$ is selected from H and C1-C6 alkyl, e.g. from H and C1-C4 alkyl, or from H and C1-C3 alkyl, or from H and C1-C2 alkyl, or from H and methyl, e.g. $R_{30}$ is H. In some embodiments, $R_{30}$ is selected from C1-C6 alkyl, e.g. from C1-C4 alkyl, or from C1-C3 alkyl, or from C1-C2 alkyl, e.g. $R_{30}$ is methyl.

In the moiety $R_{31}O$, $R_{31}$ is selected from H and C1-C6 alkyl, e.g. from H and C1-C4 alkyl, or from H and C1-C3 alkyl, or from H and C1-C2 alkyl, or from H and methyl, e.g. $R_{31}$ is H. In some embodiments, $R_{31}$ is selected from C1-C6 alkyl, e.g. from C1-C4 alkyl, or from C1-C3 alkyl, or from C1-C2 alkyl, e.g. $R_{31}$ is methyl.

In some particular embodiments, when $R_3$ is a moiety of formula (II), ring A is phenyl. In these embodiments, the compound of formula (I) may be represented by formula (Ia):

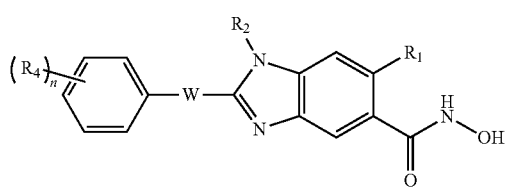

(Ia)

wherein n, W, $R_1$, $R_2$ and each $R_4$ are as defined herein.

In some embodiments of a compound of formula (Ia), n is 1 and $R_4$ is in ortho position, as represented by formula (Ia-1):

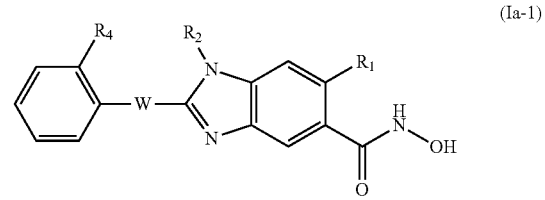

(Ia-1)

wherein W, $R_1$, $R_2$, and $R_4$ are as defined herein.

For example, in some embodiments of a compound of formula (Ia-1), $R_4$ is selected from halogen, C1-C6 alkyl, $R_5O$, $R_6C(O)$, $R_7R_8NX_1$, $R_9C(O)N(R_{10})$, $NO_2$, COOH, and CN; halogen, C1-C6 alkyl, $R_5O$, $R_6C(O)$, $R_7R_8NX_1$, $R_9C(O)N(R_{10})$, $NO_2$, and CN; from halogen, C1-C6 alkyl, $R_5O$—, $R_6C(O)$, $R_7R_8NX_1$, $R_9C(O)N(R_{10})$, COOH, and CN; from halogen, C1-C6 alkyl, $R_5O$—, $R_6C(O)$, $R_7R_8NX_1$, $R_9C(O)N(R_{10})$, and CN; or from halogen, C1-C6 alkyl, and $R_5O$, and $R_5$ and $R_6$ are preferably selected from H and C1-C6 alkyl.

In some embodiments of a compound of formula (Ia), n is 1 and $R_4$ is in meta position as represented by formula (Ia-2):

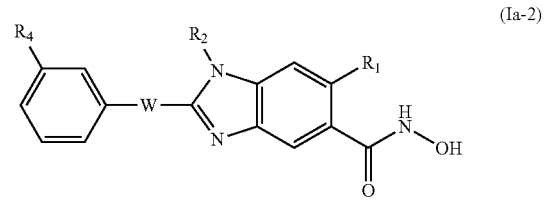

(Ia-2)

wherein W, $R_1$, $R_2$, and $R_4$ are as defined herein.

In some embodiments of a compound of formula (Ia), n is 1 and $R_4$ is in para position, as represented by formula (Ia-3):

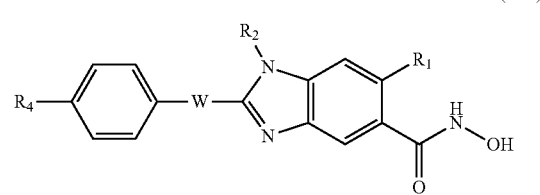

(Ia-3)

wherein W, $R_1$, $R_2$, and $R_4$ are as defined herein.

In some embodiments of a compound of formula (Ia-2) or of formula (Ia-3), $R_4$ is selected from phenyl, optionally substituted by one or more $R_{12}$, and phenoxy, optionally substituted by one or more $R_{16}$.

In some particular embodiments of a compound of formula (Ia-2) or of formula (Ia-3), $R_4$ is phenyl, optionally substituted by one or more $R_{12}$.

In some other particular embodiments of a compound of formula (Ia-2) or of formula (Ia-3), $R_4$ is phenoxy, optionally substituted by one or more $R_{16}$ (i.e. $R_4$ is $R_5O$, wherein $R_5$ is phenyl, optionally substituted by one or more $R_{16}$).

In some other embodiments of a compound of formula (Ia), n is 2.

In some embodiments of a compound of formula (Ia), n is 2 and the two $R_4$ are in ortho and meta position, respectively, as represented by formula (Ia-4):

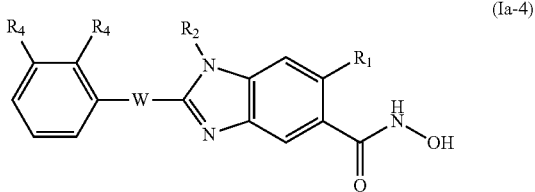

(Ia-4)

wherein W, $R_1$, $R_2$, and each $R_4$ are as defined herein.

In some embodiments of a compound of formula (Ia), n is 2 and the two $R_4$ are in ortho and para position, respectively, as represented by formula (Ia-5):

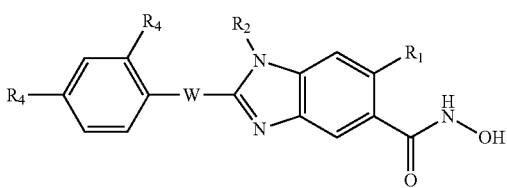

(Ia-5)

wherein W, $R_1$, $R_2$, and each $R_4$ are as defined herein.

In some embodiments of a compound of formula (Ia), n is 2 and the two $R_4$ are in ortho and meta' position, respectively, as represented by formula (Ia-6):

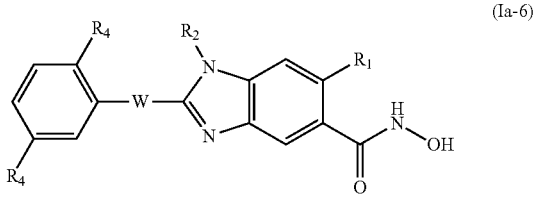

(Ia-6)

wherein W, $R_1$, $R_2$, and each $R_4$ are as defined herein.

In some embodiments of a compound of formula (Ia), n is 2 and the two $R_4$ are in ortho and ortho' position, respectively, as represented by formula (Ia-7):

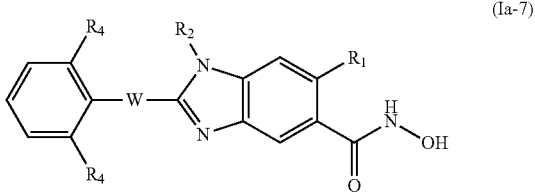

(Ia-7)

wherein W, $R_1$, $R_2$, and each $R_4$ are as defined herein.

In some embodiments of a compound of formula (Ia-7), both $R_4$ are selected from halogen, C1-C6 alkyl, $R_5O$, $R_6C(O)$, $R_7R_8NX_1$, $R_9C(O)N(R_{10})$, $NO_2$, COOH, and CN; halogen, C1-C6 alkyl, $R_5O$, $R_6C(O)$, $R_7R_8NX_1$, $R_9C(O)N(R_{10})$, $NO_2$, and CN; from halogen, C1-C6 alkyl, $R_5O$, $R_6C(O)$, $R_7R_8NX_1$, $R_9C(O)N(R_{10})$, COOH, and CN; from halogen, C1-C6 alkyl, $R_5O$, $R_6C(O)$, $R_7R_8NX_1$, $R_9C(O)N(R_{10})$, and CN; or from halogen, C1-C6 alkyl, and $R_5O$, and $R_5$ and $R_6$ are preferably selected from H and C1-C6 alkyl, e.g. H and C1-C3 alkyl, or H and methyl.

In some embodiments of a compound of formula (Ia), n is 2 and the two $R_4$ are in meta and para position, respectively, as represented by formula (Ia-8):

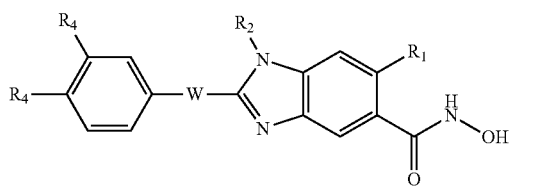

(Ia-8)

wherein W, $R_1$, $R_2$, and each $R_4$ are as defined herein.

In some embodiments of a compound of formula (Ia), n is 2 and the two $R_4$ are in meta and meta' position, respectively, as represented by formula (Ia-9):

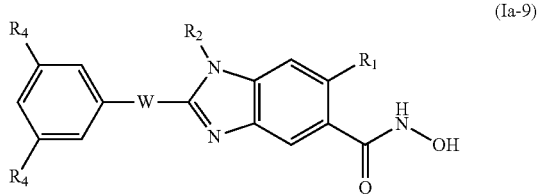

(Ia-9)

wherein W, $R_1$, $R_2$, and each $R_4$ are as defined herein.

In some other embodiments, in a compound of formula (Ia), n is 3.

In some embodiments of a compound of formula (Ia), n is 3 and the three $R_4$ are in ortho, meta and para position, respectively, as represented by formula (Ia-10):

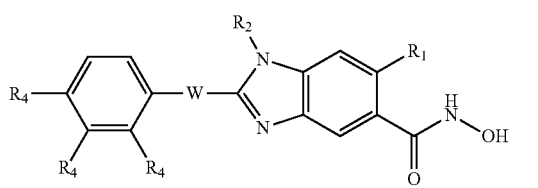

(Ia-10)

wherein W, $R_1$, $R_2$, and each $R_4$ are as defined herein.

In some embodiments of a compound of formula (Ia), n is 3 and the three $R_4$ are in ortho, meta and meta' position, respectively, as represented by formula (Ia-11):

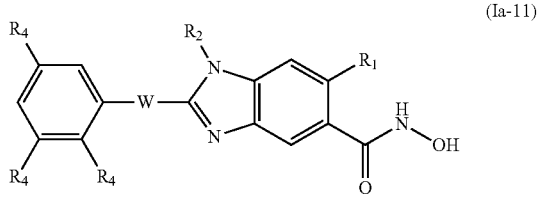

(Ia-11)

wherein W, $R_1$, $R_2$, and each $R_4$ are as defined herein.

In some embodiments of a compound of formula (Ia), n is 3 and the three $R_4$ are in ortho, meta and ortho' position, respectively, as represented by formula (Ia-12):

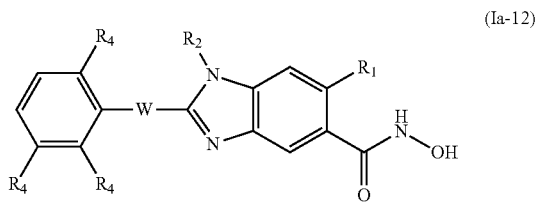
(Ia-12)

wherein W, $R_1$, $R_2$, and each $R_4$ are as defined herein.

In some embodiments of a compound of formula (Ia), n is 3 and the three $R_4$ are in meta, para, and meta' position, respectively, as represented by formula (Ia-13):

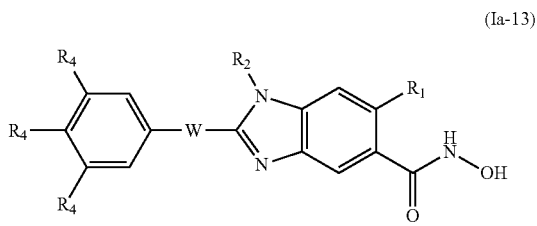
(Ia-13)

wherein W, $R_1$, $R_2$, and each $R_4$ are as defined herein.

In some embodiments of a compound of formula (Ia), n is 3 and the three $R_4$ are in ortho, para, and ortho' position, respectively, as represented by formula (Ia-14):

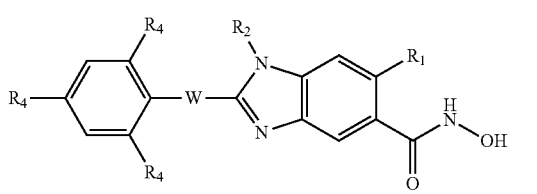
(Ia-14)

wherein W, $R_1$, $R_2$, and each $R_4$ are as defined herein.

In some embodiments of a compound of formula (Ia), n is 3 and the three $R_4$ are in ortho, para, and meta' position, respectively, as represented by formula (Ia-15):

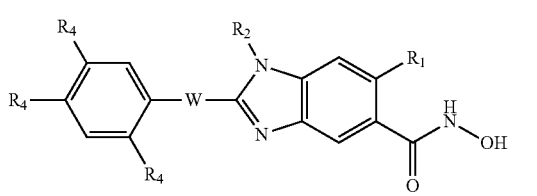
(Ia-15)

wherein W, $R_1$, $R_2$, and each $R_4$ are as defined herein.

Those of the compounds of formula (Ia) wherein at least one $R_4$ is in ortho position may be represented by a common general formula (Iaa):

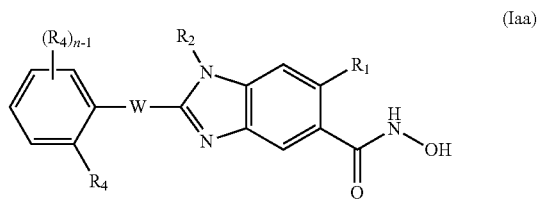
(Iaa)

wherein W, $R_1$, $R_2$, and each $R_4$ are as defined herein, and n is 1, 2 or 3.

Those of the compounds of formula (Ia) wherein at least one $R_4$ is in meta position may be represented by a common general formula (Iab):

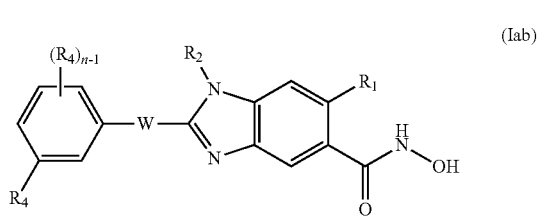
(Iab)

wherein W, $R_1$, $R_2$, and each $R_4$ are as defined herein, and n is 1, 2 or 3.

In some embodiments of a compound of formula (Iab), one $R_4$ in meta position is selected from phenyl, optionally substituted by one or more $R_{12}$, e.g. 1, 2, or 3 $R_{12}$; and phenoxy, optionally substituted by one or more $R_{16}$, e.g. 1, 2, or 3 $R_{16}$.

In some embodiments of a compound of formula (Iab), one $R_4$ in meta position is phenyl, optionally substituted by 1, 2, or 3 $R_{12}$, and the compound of formula (Iab) may then be represented by formula (Iab-1):

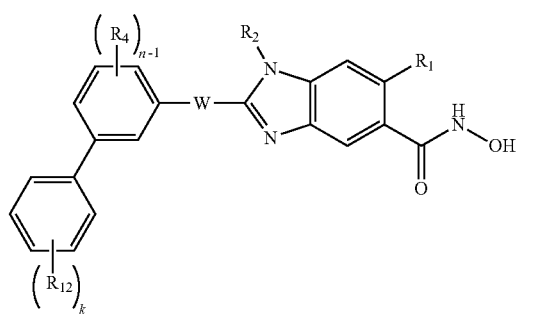
(Iab-1)

wherein W, $R_1$, $R_2$, each $R_4$, and each $R_{12}$ are as defined herein, n is 1, 2 or 3, and k is an integer of from 0 to 3, or from 0 to 2, e.g. 0 or 1.

In some other embodiments of a compound of formula (Iab), one $R_4$ in meta position is phenoxy, optionally substituted by 1, 2, or 3 $R_{16}$, and the compound of formula (Iab) may then be represented by formula (Iab-2):

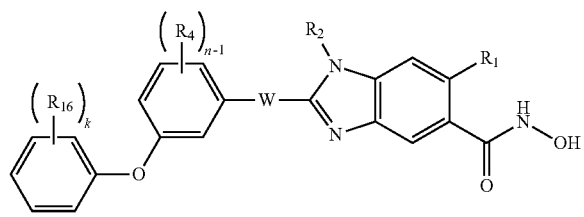
(Iab-2)

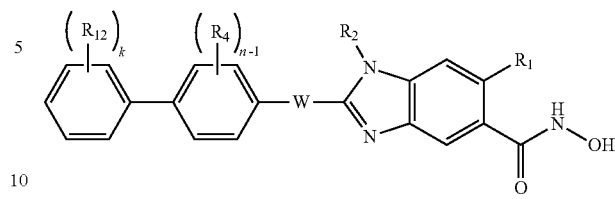
(Iac-1)

wherein W, $R_1$, $R_2$, each $R_4$, and each $R_{16}$ are as defined herein, n is 1, 2 or 3, and k is an integer of from 0 to 3, or from 0 to 2, e.g. 0 or 1.

In some embodiments of a compound of formula (Iab-1) or (Iab-2), k is 2. In some other embodiments, k is 1. In still other embodiments, k is 0.

In some embodiments of a compound of formula (Iab-1) or (Iab-2), when n is 2 or 3, each one of the further, (n−1) $R_4$ present is independently selected from halogen, C1-C6 alkyl, $R_5O$, $R_6C(O)$, $R_7R_8NX_1$, $R_9C(O)N(R_{10})$, $NO_2$, COOH, and CN; from halogen, C1-C6 alkyl, $R_5O$, $R_6C(O)$, $R_7R_8NX_1$, $R_9C(O)N(R_{10})$, $NO_2$, and CN; from halogen, C1-C6 alkyl, $R_5O$, $R_6C(O)$, $R_7R_8NX_1$, $R_9C(O)N(R_{10})$, COOH, and CN; from halogen, C1-C6 alkyl, $R_5O$, $R_6C(O)$, $R_7R_8NX_1$, $R_9C(O)N(R_{10})$, and CN; or from halogen, C1-C6 alkyl, and $R_5O$; wherein $R_5$ and R % are preferably selected from H and C1-C6 alkyl, e.g. H and C1-C3 alkyl, or H and methyl.

In some embodiments of a compound of formula (Iab-1) or (Iab-2), n−1 is 0. In some other embodiments of a compound of formula (Iab-1) or (Iab-2), n−1 is 1. In some embodiments of a compound of formula (Iab-1) or (Iab-2), n−1 is 0 and k is 0. In some other embodiments of a compound of formula (Iab-1) or (Iab-2), n−1 is 1 and k is 0. In some other embodiments of a compound of formula (Iab-1) or (Iab-2), n−1 is 0 and k is 1. In still other embodiments of a compound of formula (Iab-1) or (Iab-2), n−1 is 1 and k is 1. In other embodiments of a compound of formula (Iab-1) or (Iab-2), n−1 is 0 and k is 2

Compounds of formula (Ia) having one $R_4$ in para position may be represented by a common general formula (Iac):

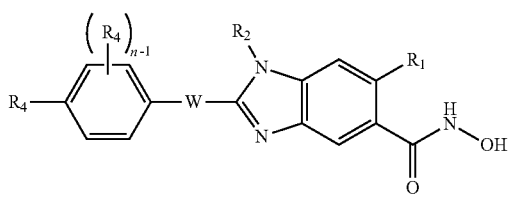
(Iac)

wherein W, $R_1$, $R_2$, and each $R_4$ are as defined herein, and n is 1, 2 or 3.

In some embodiments of a compound of formula (Iac), the $R_4$ in para position is selected from phenyl, optionally substituted by one or more $R_{12}$, e.g. 1, 2, or 3 $R_{12}$; and phenoxy, optionally substituted by one or more $R_{16}$, e.g. 1, 2, or 3 $R_{16}$.

In embodiments of a compound of formula (Iac) where the $R_4$ in para position is phenyl, optionally substituted by 1, 2, or 3 $R_{12}$, the compound of formula (Iac) may be represented by formula (Iac-1):

wherein W, $R_1$, $R_2$, each $R_4$, and each $R_{12}$ are as defined herein, n is 1, 2 or 3, and k is an integer of from 0 to 3, or from 0 to 2, e.g. 0 or 1.

In embodiments of a compound of formula (Iac) where the $R_4$ in para position is phenoxy, optionally substituted by 1, 2, or 3 $R_{16}$, the compound of formula (Iac) may be represented by formula (Iac-2):

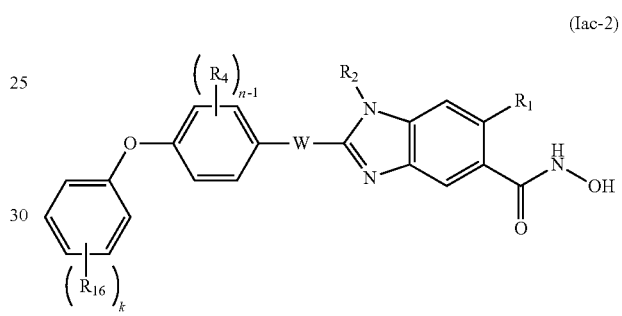
(Iac-2)

wherein W, $R_1$, $R_2$, each $R_4$, and each $R_{16}$ are as defined herein, n is 1, 2 or 3, and k is an integer of from 0 to 3, or from 0 to 2, e.g. 0 or 1.

In some embodiments of a compound of formula (Iac-1) or (Iac-2), k is 0. In some other embodiments, k is 1. In still other embodiments, k is 2.

In some embodiments of a compound of formula (Iac-1), k is 1, 2 or 3, e.g. k is 1 or 2, and one $R_{12}$ is in para position, i.e. the compound is a compound of formula (Iac-3)

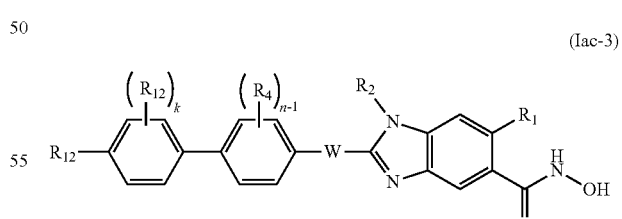
(Iac-3)

wherein W, $R_1$, $R_2$, each $R_4$, and each $R_{12}$ are as defined herein, n is 1, 2 or 3, and k is 1, 2 or 3, e.g. k is 1 or 2, or k is 1.

In some further embodiments of a compound of formula (Iac-1), k is 1, 2 or 3, e.g. k is 1 or 2, and one $R_{12}$ is in meta position, i.e. the compound is a compound of formula (Iac-4)

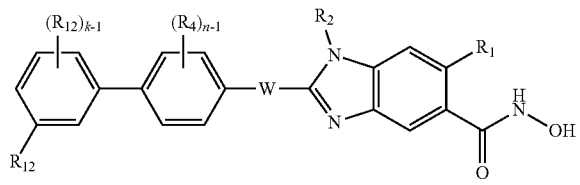
(Iac-4)

wherein W, $R_1$, $R_2$, each $R_4$, and each $R_{12}$ are as defined herein, n is 1, 2 or 3, and k is 1, 2 or 3, e.g. k is 1 or 2, or k is 1.

In some embodiments of a compound of formula (Iac-1), (Iac-2), (Iac-3), or (Iac-4), n–1 is 0. In some other embodiments of a compound of formula ((Iac-1), (Iac-2), (Iac-3), or (Iac-4), n–1 is 1. In some particular embodiments of a compound of formula ((Iac-1) or (Iac-2) n–1 is 0 and k is 0. In some other embodiments of a compound of formula (Iac-1) or (Iac-2), n–1 is 1 and k is 0. In some other embodiments of a compound of formula (Iac-1), (Iac-2), (Iac-3), or (Iac-4), n–1 is 0 and k is 1. In still other embodiments of a compound of formula (Iac-1), (Iac-2), (Iac-3), or (Iac-4), n–1 is 1 and k is 1. In other embodiments of a compound of formula (Iac-1), (Iac-2), (Iac-3), or (Iac-4), n–1 is 0 and k is 2

In a compound of formula (Ia), any $R_4$ present in ortho position (i.e. adjacent to the carbon atom attached to W) preferably is not selected from (optionally substituted) phenyl or (optionally substituted) phenoxy, e.g. any $R_4$ in ortho position is selected from halogen, C1-C6 alkyl, and $R_5O$—, wherein $R_5$ is selected from H and C1-C6 alkyl.

In some embodiments of a compound of formula (Ia), each $R_4$ is independently selected from halogen, C1-C6 alkyl, and $R_5O$—, wherein $R_5$ is selected from H and C1-C6 alkyl.

In some embodiments of a compound of formula (I), when $R_3$ is a moiety of formula (II), ring A is naphthyl. In these embodiments, the compound of formula (I) may be represented by formula (Ib):

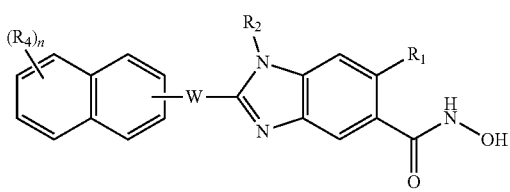
(Ib)

wherein n, W, $R_1$, $R_2$, and each $R_4$ are as defined herein.

In some embodiments of a compound of formula (Ib), n is 1, 2 or 3; e.g. n is 1 or 2; or n is 1. In some embodiments of a compound of formula (Ib), n is 0, 1, or 2; e.g. n is 0 or 1; or n is 0.

In some embodiments, a compound of formula (Ib) is more particularly a compound of formula (Ib-1):

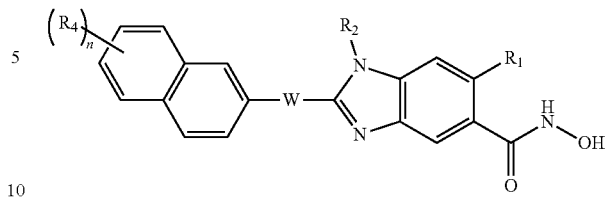
(Ib-1)

wherein n, W, $R_1$, $R_2$, and each $R_4$ are as defined herein.

In some other embodiments, a compound of formula (Ib) is more particularly a compound of formula (Ib-2):

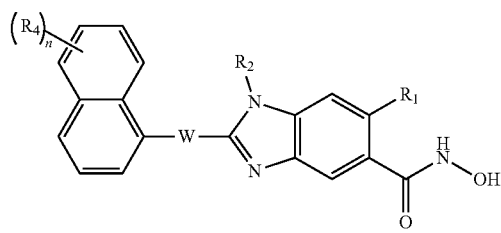
(Ib-2)

wherein n, W, $R_1$, $R_2$, and each $R_4$ are as defined herein.

It should be understood that in formula (Ib), any $R_4$ may be attached to either one of the two rings (i.e. either the proximal, or the distal) of the naphthyl moiety.

In some embodiments of a compound of formula (Ib), any $R_4$ present is attached to the distal ring. In some embodiments, n is 1 and $R_4$ is attached to the distal ring.

In some other embodiments of a compound of formula (Ib), any $R_4$ present is attached to the proximal ring. In some embodiments, n is 1 and $R_4$ is attached to the proximal ring.

In a compound of formula (Ib), each $R_4$ is as defined herein above.

In some embodiments of a compound of formula (Ib), any $R_4$ present in ortho position on the proximal benzene ring preferably is not selected from (optionally substituted) phenyl or (optionally substituted) phenoxy.

In some embodiments of a compound of formula (Ib), any $R_4$ present on the proximal benzene ring preferably is not selected from (optionally substituted) phenyl or (optionally substituted) phenoxy.

In some embodiments of a compound of formula (Ib), any $R_4$ present preferably is not selected from (optionally substituted) phenyl or (optionally substituted) phenoxy.

In some embodiments of a compound of formula (Ib), each $R_4$ is independently selected from halogen, C1-C6 alkyl, and $R_5O$—, wherein $R_5$ is selected from H and C1-C6 alkyl.

In some embodiments of a compound of formula (I), when $R_3$ is a moiety of formula (II), ring A is ring A is 5- to 10-membered mono- or bicyclic heteroaryl. In some of these embodiments ring A is or 9- to 10 membered bicyclic heteroaryl containing at least one benzene ring fused with a heteroaromatic ring. In these embodiments, the benzene ring may be either the proximal or distal ring. In some embodiments, A is or 9- to 10 membered bicyclic heteroaryl containing a benzene ring, and the benzene ring is the proximal ring. The compound of formula (I) may then be represented by formula (Ik):

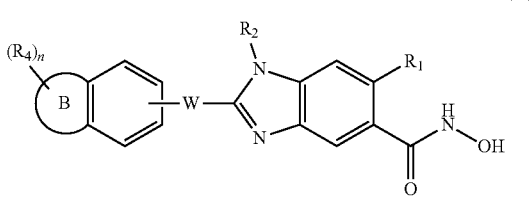

(Ik)

wherein ring B is a heteroaromatic 5- or 6-membered ring, and n, W, $R_1$, $R_2$, and each $R_4$ are as defined herein, and each $R_4$ may be attached either to ring B or to the benzene ring.

In some embodiments, the compound of formula (Ik) may more particularly be represented by formula (Ik-1):

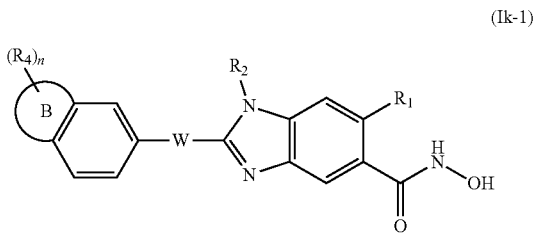

(Ik-1)

wherein ring B is a heteroaromatic 5- or 6-membered ring, and n, W, $R_1$, $R_2$, and each $R_4$ are as defined herein, and each $R_4$ may be attached either to ring B or to the benzene ring.

In some other embodiments, the compound of formula (Ik) may more particularly be represented by formula (Ik-2):

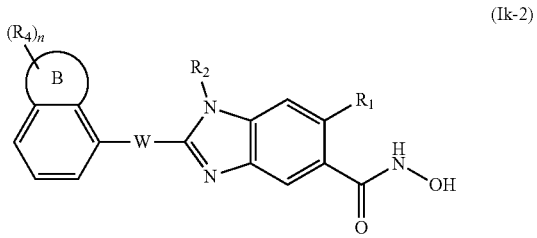

(Ik-2)

wherein ring B is a heteroaromatic 5- or 6-membered ring, and n, W, $R_1$, $R_2$, and each $R_4$ are as defined herein, and each $R_4$ may be attached either to ring B or to the benzene ring.

In still other embodiments, A is or 9- to 10 membered bicyclic heteroaryl containing a benzene ring, which benzene ring according to the above definition is the distal ring, i.e. the compound is as represented by formula (Im):

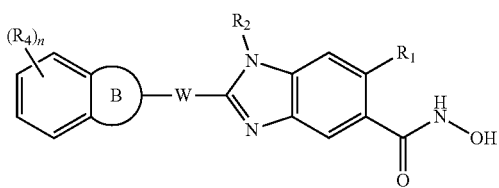

(Im)

wherein ring B is a heteroaromatic 5- or 6-membered ring, and n, W, $R_1$, $R_2$, and each $R_4$ are as defined herein, and each $R_4$ may be attached either to ring B or to the benzene ring.

In some embodiments of a compound of formula (Ik) or (Im), ring B is a 5-membered heteroaromatic ring containing 1, 2 or 3 heteroatoms in the ring, e.g. 1 or 2 heteroatoms, or 1 heteroatom.

In some other embodiments of a compound of formula (Ik) or (Im), ring B is a 6-membered heteroaromatic ring containing 1, 2, 3 or 4 heteroatoms in the ring, e.g. 1, 2 or 3 heteroatoms; or 1 or 2 heteroatoms, e.g. 1 heteroatom.

In some particular embodiments of a compound of formula (Ik) or (Im), each $R_4$ is attached to the benzene ring. In some other embodiments, at least one $R_4$ is attached to the benzene ring.

In some embodiments of a compound of formula (Ik) or (Im), n is 0 or 1. In some other embodiments, n is 0. In still other embodiments, n is an integer of from 1 to 3, e.g. n is 1 or 2, in particular n is 1.

In some embodiments of a compound of formula (Ik) or (Im), any $R_4$ present in ortho position on the proximal ring (or more generally: attached to the atom adjacent to the bond to X) preferably is not selected from (optionally substituted) phenyl or (optionally substituted) phenoxy.

In some embodiments of a compound of formula (Ik) or (Im), any $R_4$ attached to the proximal ring preferably is not selected from (optionally substituted) phenyl or (optionally substituted) phenoxy.

In some embodiments of a compound of formula (Ik) or (Im), any $R_4$ present preferably is not selected from (optionally substituted) phenyl or (optionally substituted) phenoxy.

In some embodiments of a compound of formula (Ik) or (Im), each $R_4$ is independently selected from halogen, C1-C6 alkyl, and $R_5O$—, wherein $R_5$ is selected from H and C1-C6 alkyl.

Each heteroatom in ring B may suitably be selected from N, O and S. In some embodiments, of a compound of formula (Ik) or (Im), ring B contains at least one N. In some other embodiments, ring B contains N as only heteroatom.

In a compound of formula (I), the moiety W is a direct bond, C1-C3 alkylene, or C2-C3 alkenylene, said alkylene or alkenylene optionally being substituted by one or more C1-C3 alkyl, e.g. one or more methyl. In some embodiments, W is a direct bond, C1-C2 alkylene, or C2 alkenylene, said alkylene or alkenylene optionally being substituted by one or more C1-C3 alkyl, e.g. one or more methyl. In some embodiments, W is a direct bond, $CH_2$, $CH(CH_3)$, $CH_2CH_2$, or $CH=CH$. In some embodiments, W is a direct bond or $CH_2$, e.g. W is a direct bond. In some other embodiments, W is C1-C3 alkylene, or C2-C3 alkenylene, said alkylene or alkenylene optionally being substituted by one or more C1-C3 alkyl, e.g. C1-C2 alkylene, or C2 alkenylene, said alkylene or alkenylene optionally being substituted by one or more C1-C3 alkyl, e.g. one or more methyl, e.g. W is $CH_2$, $CH(CH_3)$, $CH_2CH_2$, or $CH=CH$.

In some embodiments of a compound of formula (I), when $R_3$ is a moiety of formula (II), ring A is a monocyclic heteroaryl as described herein above. In some embodiments, when ring A is a monocyclic heteroaryl, the compound is represented by formula (In)

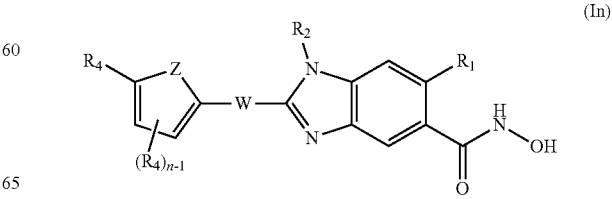

(In)

wherein W, $R_1$, $R_2$, and each $R_4$ are as defined herein, and n is 1 or 2, in particular n is 1, and Z is a O, S or $NR_4$, in particular Z is O or S.

In some particular embodiments the compound may be represented by formula (In-1)

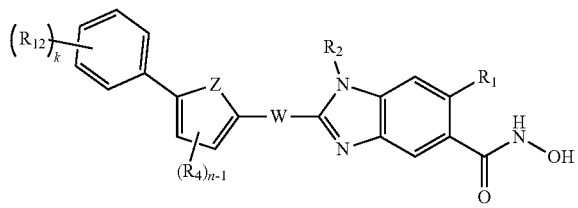

(In-1)

wherein W, $R_1$, $R_2$, and each $R_4$ are as defined herein, n is 1 or 2, in particular n is 1, k is an integer of from 0 to 3, e.g. from 0 to 2, such as 0 or 1, and Z is a O, S or $NR_4$, in particular Z is O or S.

It should be noted that in a compound of formula (I), any alkyl is optionally substituted with one or more F. For example, any methyl group may be substituted with 1, 2 or 3 F, e.g. 2 or 3 F, in particular 3F.

Unless the contrary is clearly apparent from the context or specifically indicated, it is contemplated that any of the above outlined different features of the compound of formula (I) may be independently combined to give rise to various embodiments within the scope of the invention, whether or not these embodiments are represented by specific formulas (Ia) to (Im). Furthermore, unless the contrary is clearly apparent from the context or specifically indicated, any reference to a compound of formula (I) also should be construed as a reference to a compound according to any of the formulas (Ia) to (Im), or any of the embodiments thereof.

Stereoisomers

Whenever a chiral carbon is present in the compound of formula (I), it is intended that all stereoisomers associated with that chiral carbon are encompassed formula (I), unless otherwise specified. Using the Cahn-Ingold-Prelog RS notational system, any asymmetric carbon atom may be present in the (R)- or (S)-configuration, and the compound may be present as a mixture of its stereoisomers, e.g. a racemic (equal) or unequal mixture, or one stereoisomer only. Stereoisomers include enantiomers and diastereomers.

Tautomers

Formula (I) includes all tautomers of the compound of the invention. For example, the benzimidazole moiety exists in two tautomeric forms:

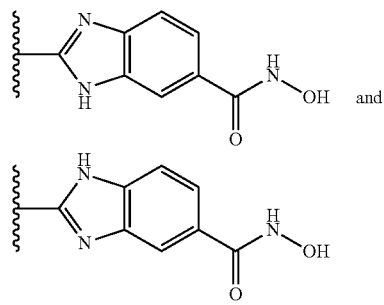

and both are considered as within the scope of the present invention.

Pharmaceutically Acceptable Salts

A pharmaceutically acceptable salt of the compound of formula (I) may be an acid addition salt or a base addition salt.

In the preparation of acid or base addition salts, such acids or bases are used which form suitable pharmaceutically acceptable salts. Examples of such acids are inorganic acids such as hydrohalogen acids, sulfuric acid, phosphoric acid, nitric acid; organic aliphatic, alicyclic, aromatic or heterocyclic carboxylic or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybenzoic acid, embonic acid, methanesulfonic acid, ethanesulfonic acid, hydroxyethanesulfonic acid, halogenbenzenesulfonic acid, toluenesulfonic acid or naphthalenesulfonic acid.

Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Examples of bases useful in preparing salts of the present invention include sodium hydroxide, potassium hydroxide, ammonium hydroxide, potassium carbonate, and the like.

Pharmaceutical Formulations

A pharmaceutical composition according to the invention may be for topical (local) or systemic administration, e.g. for enteral administration, such as rectal or oral administration, or for parenteral administration to a mammal (especially a human), and comprises a therapeutically effective amount of a compound according to the invention or a pharmaceutically acceptable salt thereof, as active ingredient, in association with a pharmaceutically acceptable excipient, e.g. a pharmaceutically acceptable carrier. The therapeutically effective amount of the active ingredient is as defined herein above and depends e.g. on the species of mammal, the body weight, the age, the individual condition, individual pharmacokinetic data, the disease to be treated and the mode of administration.

For enteral, e.g. oral, administration, the compounds of the invention may be formulated in a wide variety of dosage forms. The pharmaceutical compositions and dosage forms may comprise a compound or compounds of the present invention or pharmaceutically acceptable salt(s) thereof as the active component. The pharmaceutically acceptable carriers may be either solid or liquid. Solid form preparations include powders, tablets, pills, lozenges, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The formulation of the active compound may comprise an encapsulating material as carrier, providing a capsule in which the active component, with or without carriers, is surrounded by a carrier, which is in association with it.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

The compounds of the invention also may be administered parenterally, e.g. by inhalation, injection or infusion, e.g. by intravenous, intraarterial, intraosseous, intramuscular, intracerebral, intracerebroventricular, intrasynovial, intrasternal, intrathecal, intralesional, intracranial, intratumoral, intracutaneous and subcutaneous injection or infusion.

Thus, for parenteral administration, the pharmaceutical compositions of the invention may be in the form of a sterile injectable or infusible preparation, for example, as a sterile aqueous or oleaginous suspension. This suspension may be formulated according to techniques known in the art using suitable dispersing or wetting agents (e.g. Tween 80), and suspending agents. The sterile injectable or infusible preparation may also be a sterile injectable or infusible solution or suspension in a non-toxic parenterally acceptable diluent or solvent. For example, the pharmaceutical composition may be a solution in 1,3-butanediol. Other examples of acceptable vehicles and solvents that may be employed in the compositions of the present invention include, but are not limited to, mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

Solutions for parenteral use also may contain suitable stabilizing agents, and if necessary, buffer substances. Suitable stabilizing agents include antioxidizing agents, such as sodium bisulfate, sodium sulfite or ascorbic acid, either alone or combined, citric acid and its salts and sodium EDTA. Parenteral solutions may also contain preservatives, such as benzalkonium chloride, methyl- or propyl-paraben, and chlorobutanol.

For inhalation or nasal administration, suitable pharmaceutical formulations are as particles, aerosols, powders, mists or droplets, e.g. with an average size of about 10 μm in diameter or less. For example, compositions for inhalation may be prepared as solutions in saline, employing benzyl alcohol or other suitable preservatives, absorption promoters to enhance bioavailability, fluorocarbons, and/or other solubilizing or dispersing agents known in the art.

The pharmaceutical compositions of the invention also may be administered topically, to the skin or to a mucous membrane. For topical application, the pharmaceutical composition may be e.g. a lotion, a gel, a paste, a tincture, a transdermal patch, a gel for transmucosal delivery. The composition may be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition may be formulated as a suitable lotion or cream containing the active compound suspended or dissolved in a carrier. Suitable carriers include, but are not limited to, mineral oil, sorbitan monostearate, polysorbate 60, cetyl esters wax, cetaryl alcohol, 2-octyldodecanol, benzyl alcohol and water. The pharmaceutical compositions of this invention may also be topically applied to the lower intestinal tract by rectal suppository formulation or in a suitable enema formulation.

Suitable pharmaceutical excipients, e.g. carriers, and methods of preparing pharmaceutical dosage forms are described in Remington's Pharmaceutical Sciences, Mack Publishing Company, a standard reference text in art of drug formulation.

The pharmaceutical compositions may comprise from approximately 1% to approximately 95%, preferably from approximately 20% to approximately 90% of a compound of formula (I), together with at least one pharmaceutically acceptable excipient. In general, the compounds of the invention will be administered in a therapeutically effective amount by any of the accepted modes of administration for agents that serve similar utilities. Suitable daily dosages typically ranges from 1 to 1000 mg, e.g. 1-500 mg daily, or 1-50 mg daily, depending upon numerous factors such as the severity of the disease to be treated, the age and relative health of the patient, the potency of the compound used, the route and form of administration, and the indication towards which the administration is directed, etc. One of ordinary skill in the art of treating such diseases will be able, without undue experimentation and in reliance upon personal knowledge and the disclosure of this application, to ascertain a therapeutically effective amount of the compounds of the present invention for a given disease. Compounds of the invention may be administered as pharmaceutical formulations including those suitable for enteral or parenteral administration. The preferred manner of administration is generally oral using a convenient daily dosage regimen which can be adjusted according to the degree of affliction.

The compounds of the present invention may also be used or administered in combination with one or more additional therapeutically active agents, e.g. drugs useful in the treatment of a disorder selected from autoimmune disorders, mental disorders, neurodegenerative disorders and cancers. The components may be in the same formulation or in separate formulations for administration simultaneously or sequentially.

Accordingly, in a further aspect of the invention, there is provided a combination product comprising:
(A) a compound of the invention, as defined herein; and
(B) another therapeutic agent, e.g. one that is useful in the treatment of a disorder selected from autoimmune disorders, mental disorders, neurodegenerative disorders and cancers; whereby (A) and (B) is formulated in admixture with a pharmaceutically acceptable excipient.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention, as hereinbefore defined, another therapeutic agent, and a pharmaceutically acceptable excipient, e.g. an adjuvant, diluent or carrier; and
(2) a kit of parts comprising, as components:
(a) a pharmaceutical formulation including a compound of the invention, as defined herein, in admixture with a pharmaceutically acceptable excipient, e.g. an adjuvant, diluent or carrier; and
(b) a pharmaceutical formulation including another therapeutic agent in admixture with a pharmaceutically acceptable excipient, e.g. an adjuvant, diluent or carrier, which components (a) and (b) are each provided in a form that is suitable for administration in conjunction with the other.

The compounds of the present invention may also be used or administered in combination with other treatment such as irradiation for the treatment of cancer.

Methods of Treatment

According to one aspect, the present invention relates to a method of treatment of a disease that responds to inhibition of histone deacetylase 6, e.g. a disorder selected from autoimmune disorders, neurodegenerative disorders, and hyperproliferative disorders, such as cancers, which method comprises administering a therapeutically effective amount of a compound of formula (I), or pharmaceutically acceptable salt thereof, to a warm-blooded animal, e.g. a mammal, such as a human, in need of such treatment.

While the compounds of the invention may be administered to a subject in need of treatment e.g. by use of a pharmaceutical formulation and administration route as generally outlined herein above, it should be realized that precise treatment regime, e.g. dosage, will normally be determined by the treating physician.

In some embodiments, the disorder to be treated is an autoimmune disorder, such as any of the autoimmune disorders mentioned herein above, e.g. colitis, or allograft rejection.

In some embodiments, the disorder is a neurodegenerative disorder, such as any of the neurodegenerative disorders mentioned herein above, for example Alzheimer's disease, Parkinson's disease or Huntington's disease.

In some embodiments, the disorder is a mental disorder, such as any of the mental disorders referred to herein above, e.g. a depressive disorder or a stress-induced mental disorder.

In some embodiments, the disorder is a hyperproliferative disorder, such as any of the hyperproliferative disorders mentioned herein above, e.g, a malignant hyperproliferative disorder (cancer).

Methods of Preparation

The compounds of formula (I) may be prepared by the person of ordinary skill in the art, using conventional methods of chemical synthesis. The preparation of some intermediates and compounds according to the present invention may in particular be illustrated by the following Schemes.

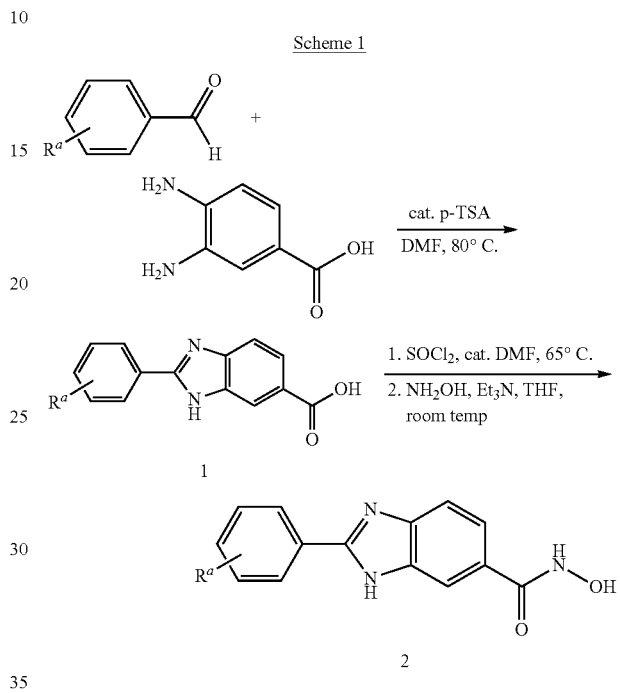

Compounds of formula (I) may for example be prepared according to the route shown in Scheme 1. Condensation of the 3,4-diaminobenzoic acid with an aromatic or heteroaromatic aldehyde in the presence of air and p-toluenesulfonic acid in DMF at 80° C. results in the formation of benzimidazoles of formula (1) (Xiangming, H. et al., *ARKIVOC*, 2007, xiii, 150-154). Transformation of carboxylic acids (1) to hydroxamic acids (2) by reaction with hydroxylamine may be accomplished in a two-step procedure where an intermediate acid chloride is formed by SOCl$_2$ in the presence of catalytic amounts of DMF.

Compounds of formula (I) may also for example be prepared according to the route shown in Scheme 2. Amide coupling between methyl 3,4-diaminobenzoate and phenyl acetic acids results in the formation of intermediates of formula (3). Subsequent ring closure under acidic conditions gives benzimidazoles (4) (Charton, J. et al., *Bioorg. Med. Chem*, 2006, 14, 4490-4518), which may be transformed into the corresponding hydroxamic acids (5) according to the two-step procedure described in Scheme 1.

Scheme 2

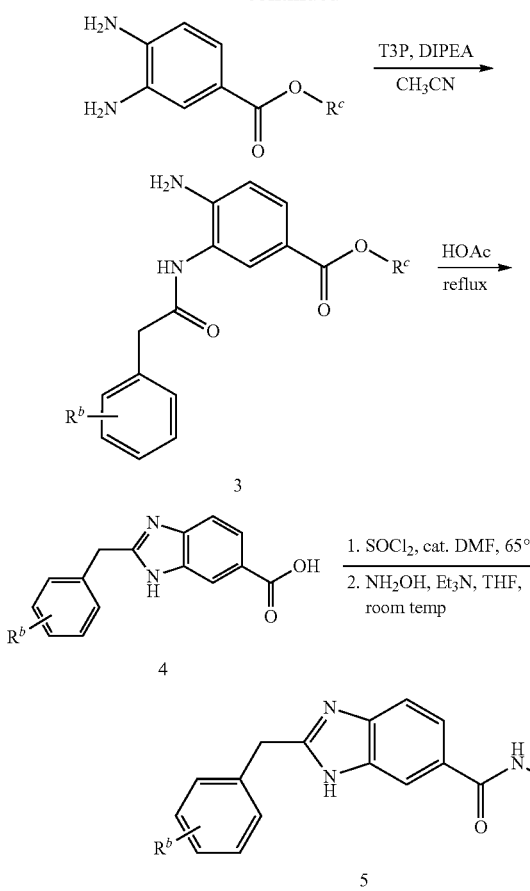

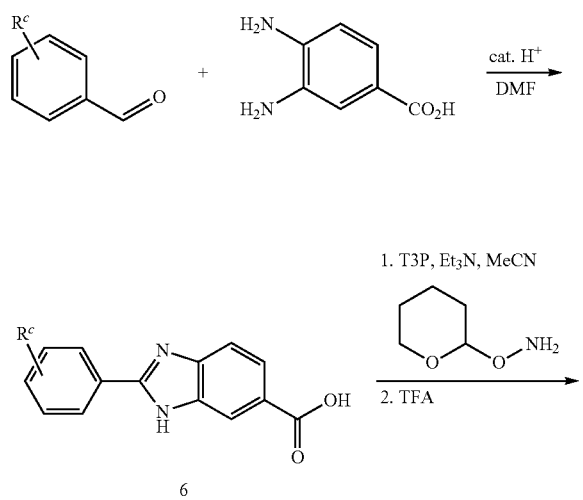

Compounds of formula (I) may also be prepared according to the route shown in Scheme 3. Acid catalyzed condensation of aldehyde and 3,4-diaminobenzoic acid in the presence of air gives benzimidazole carboxylic acid (6). Amide coupling with O-(tetrahydropyran-2-yl)-hydroxylamine followed by deprotection using TFA affords the corresponding hydroxamic acid (7).

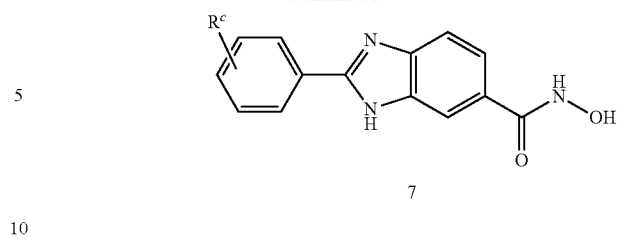

Compounds of formula (I) may also be prepared according to the route shown in Scheme 4. Amide coupling of 4-amino-3-nitrobenzoic acid and O-benzylprotected hydroxylamine followed by hydrogenation gives 3,4-diamino-N-hydroxylbenzamide (8). Acid catalyzed condensation with aldehyde in the presence of air gives the desired hydroxamic acid (9).

Scheme 4

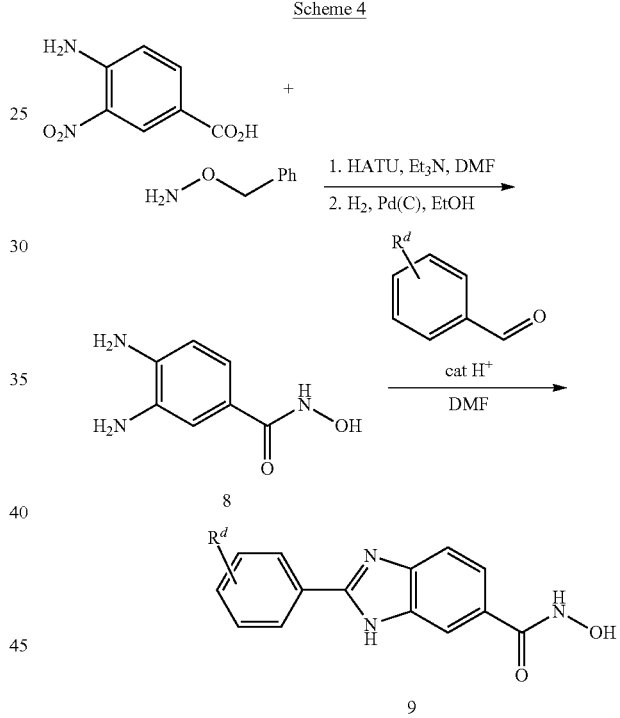

Compounds of formula (I) may also be prepared according to the route shown in Scheme 5. Acid catalyzed condensation of bromobenzaldehyde and methyl 3,4-diaminobenzoate in presence of air gives the bromoaryl intermediate (10) which is used as a substrate in coupling with arylboronic acids (or esters) under Suzuki coupling conditions. The resulting biaryl benzimidazole ester (11) is transformed to hydroxamic acid (12) using potassium salt of hydroxylamine in MeOH.

Scheme 5

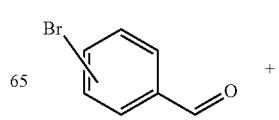

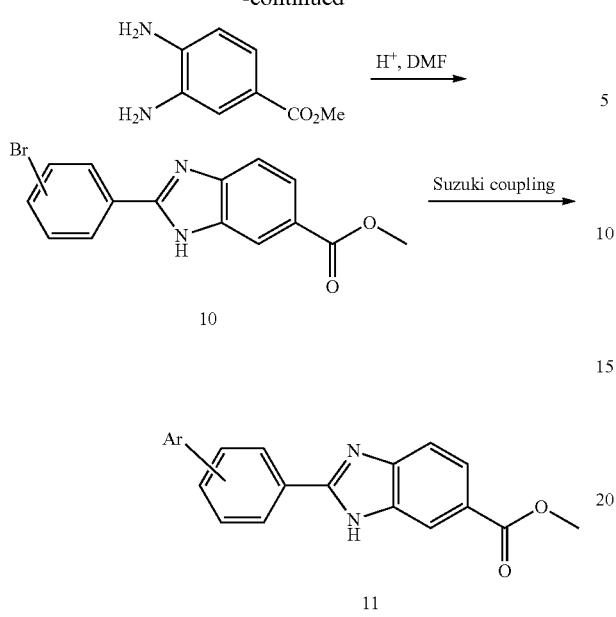

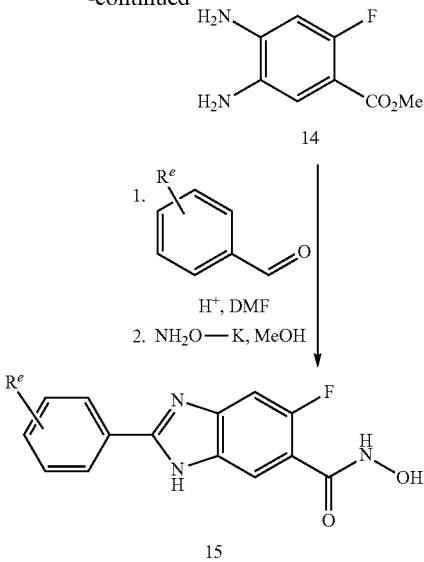

Compounds of formula (I) may also be prepared according to the route shown in Scheme 6. tert-Butylamine and methyl 2,4-difluoro-5-nitrobenzoate in the presence of base gives the protected amine (13) which is deprotected in TFA followed by palladium catalyzed reduction under $H_2$. Acid catalyzed condensation of the diamine (14) and aldehyde gives the benzimidazole methyl ester which is transformed to the desired hydroxamic acid (15) using hydroxylamine potassium salt in methanol.

Compounds of formula (I) may also be prepared according to the route shown in Scheme 7. Amide coupling of 4-(methylamino)-3-nitrobenzoic acid and O-benzylprotected hydroxylamine followed by hydrogenation gives 3,4-diamino-N-hydroxylbenzamide (16). Acid catalyzed condensation with aldehyde in the presence of air gives the desired hydroxamic acid (17).

Scheme 7

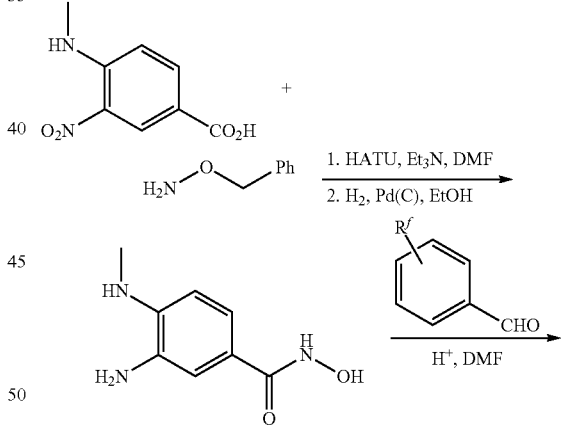

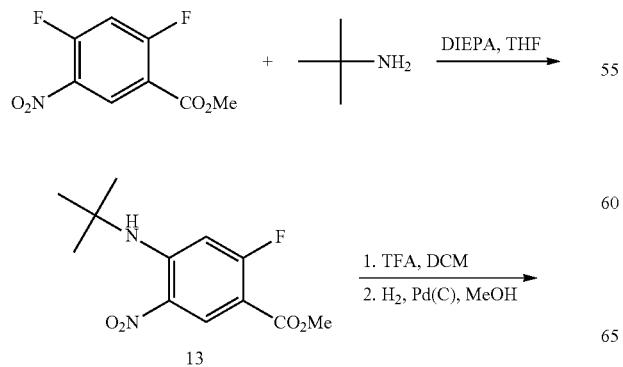

Compounds of formula (I) may also be prepared according to the route shown in Scheme 8. Carboxylic acid and methyl 3,4-diaminobenzoate in the presence of $POCl_3$ in MeCN is heated at 120° C. in microwave reactor to give benzimidazole methyl ester (18). The ester is converted to the desired hydroxamic acid (19) when reacted with hydroxylamine potassium salt in methanol.

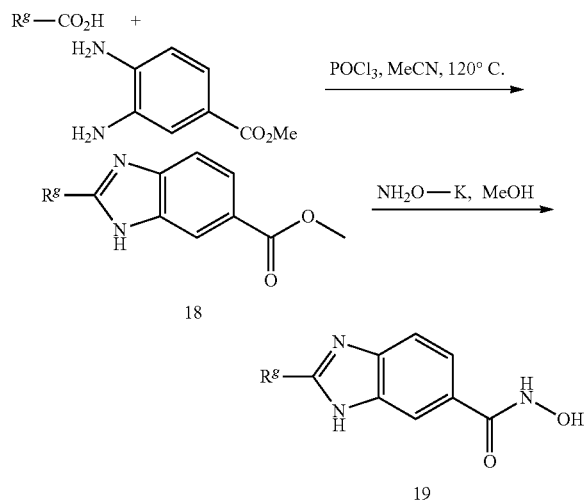

The necessary starting materials for preparation of the compounds of formula (I) are either commercially available, or may be prepared by methods known in the art.

The reactions described below in the experimental section may be carried out to give a compound of the invention in the form of a free base or as an acid or base addition salt. The term pharmaceutically acceptable salt of a compound refers to a salt that is pharmaceutically acceptable, as defined herein, and that possesses the desired pharmacological activity of the parent compound. A pharmaceutically acceptable acid addition salt may be obtained by dissolving the free base in a suitable organic solvent and treating the solution with an acid, in accordance with conventional procedures for preparation of acid addition salts from free bases.

The compounds of formula (I) may possess one or more chiral carbon atoms, and may therefore be obtained in the form of optical isomers, e.g. as a pure enantiomer, or as a mixture of enantiomers (racemate) or as a mixture of diastereomers. The separation of mixtures of optical isomers to obtain pure enantiomers is well known in the art and may, for example, be achieved by fractional crystallization of salts with optically active (chiral) acids or by chromatographic separation on chiral columns.

The chemicals used in the synthetic routes described herein may include, for example, solvents, reagents, catalysts, and protecting group and deprotecting group reagents. Examples of protecting groups are t-butoxycarbonyl (Boc), benzyl, trityl (triphenylmethyl) and trimethylsilyl. The methods described above may also additionally include steps, either before or after the steps described specifically herein, to add or to remove suitable protecting groups in order to ultimately allow synthesis of the compounds. In addition, various synthetic steps may be performed in an alternate sequence or order to give the desired compounds. Synthetic chemistry transformations and protecting group methodologies are known in the art and include, for example, those described in R. C. Larock, *Comprehensive Organic Transformations*, VCH Publishers (1989); L. Fieser and M. Fieser, *Fieser and Fieser's Reagents for Organic Synthesis*, John Wiley and Sons (1994); L. A. Paquette, ed., *Encyclopedia of Reagents for Organic Synthesis*, John Wiley and Sons (1995); T. H. Greene and P. G. M. Wuts, *Protective Groups in Organic Synthesis*, 3$^{rd}$ Ed., John Wiley and Sons (1999); and P. J. Kocieński, *Protecting Groups*, Georg Thieme Verlag, (2000) and subsequent editions thereof.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

The invention will now be further illustrated by the following non-limiting examples. The specific examples below are to be construed as merely illustrative, and not limitative of the remainder of the disclosure in any way whatsoever. Without further elaboration, it is believed that one skilled in the art can, based on the description herein, utilize the present invention to its fullest extent.

EXAMPLES

The following abbreviations have been used:
AcOH Acetic acid
DCM Dichloromethane
DIPEA N,N-diisopropylethylamine
DMF N,N-dimethylformamide
DMSO Dimethyl sulfoxide
dppf 1,1'-Bis(diphenylphosphino)ferrocene
ESI Electrospray ionization
Et$_3$N Triethylamine
EtOAc Ethyl acetate
HATU (1-[Bis(dimethylamino)methylene]-1H-1,2,3-triazolo[4,5-b]pyridinium-3-oxide hexafluorophosphate)
HPLC High Performance Liquid Chromatography
HOAc Acetic acid
MeOH Methanol
MS Mass Spectrometry
NMR Nuclear Magnetic Resonance
rt Room temperature
THF tetrahydrofurane
T3P Propylphosphonic anhydride
TFA Trifluoroacetic acid
p-TSA p-Toluenesulfonic acid Experimental Methods $^1$H NMR spectra were recorded on a Varian Inova 600 equipped with a triple resonance probe. All spectra were recorded using the residual solvent proton resonance or tetramethylsilane (TMS) as internal standard. Analytical HPLC was carried out on an Agilent Series 1100 system using either an ACE C8 (3 µm, 3.0×50 mm) column with 0.1% TFA in MilliQ H$_2$O/CH$_3$CN as mobile phase (Acidic system) or an XTerra (3.5 µm, 3.0×50 mm) column with 10 mM pH 10 NH$_4$HCO$_3$/CH$_3$CN as mobile phase (Basic system). Electrospray ionization mass spectrometry (ESI-MS) was performed using an Agilent 1100 Series Liquid Chromatograph/Mass Selective Detector (MSD) to obtain the pseudo molecular [M+H]$^+$ ion of the target molecules. Preparative HPLC was performed on a Gilson 306 HPLC system using an ACE C8 (5 µm, 21×50 mm) or Kinetex C18 (5 µm, 21×100 mm) column with 0.1% TFA in MilliQ H$_2$O/CH$_3$CN as mobile phase (Acidic systems) (flow 25 ml/min, gradient over 6 or 12 min), or Gemini-NX C18 (5 µm, 21×50 mm) with 50 mM NH$_4$HCO$_3$ in MilliQ H$_2$O/CH$_3$CN as mobile phase (basic system) (flow 25 mL/min, gradient over 12 min). Fractions were collected based on the UV-signal at 254 nm. Preparative flash chromatography was performed on Merck silica gel 60 (230-400 mesh) or YMC gel 120 Å S-150 μm. The compounds were named using the software ACD Labs 10.0 Name module. Hydroxylamine potassium solution in MeOH was prepared according to the procedure reported by C. Blackburn et. al. (U.S. Pat. Appl. Publ. 20120015943). Hydroxylamine hydrochloride (2.0 g, 29 mmol) in methanol (10 ml) was heated at 90° C. for 15 min. Everything dissolved. KOH (2.85 g, 50.8 mmol) was dissolved in MeOH (6 ml) and added to the solution of hydroxylamine hydrochloride (white precipitate upon addition). The mixture was heated at 90° C. for 30 min. Cooled to room temperature and centrifuged. The clear solution was taken out by a syringe.

Intermediate 1

3,4-Diamino-N-hydroxybenzamide

Step 1. Triethylamine (3.0 g, 30 mmol), HATU (4.2 g, 11 mmol) and 4-amino-3-nitrobenzoic acid (1.8 g, 10 mmol) were mixed in 100 ml of DMF at ambient temperature. After 15 minutes O-benzylhydroxylamine hydrochloride (1.76 g, 11 mmol) was added. Brine and EtOAc were added after 2 h. The organic phase was washed with water, saturated $NaHCO_3$ (aq) and brine, dried over $MgSO_4$, filtered and concentrated. The residue was recrystallized from water/methanol. The intermediate 4-amino-N-(benzyloxy)-3-nitrobenzamide was obtained as a yellow solid in 75% yield (2.1 g). MS (ESI+) m/z 288 [M+H]$^+$. HPLC purity: 100%. $^1$H NMR (600 MHz, DMSO-d6) δ ppm 11.73 (s, 1H) 8.46 (d, J=1.83 Hz, 1H) 7.81 (br. s., 2H) 7.75 (dd, J=8.85, 2.14 Hz, 1H) 7.31-7.48 (m, 5H) 7.03 (d, J=8.85 Hz, 1H) 4.90 (s, 2H).

Step 2. 4-Amino-N-(benzyloxy)-3-nitrobenzamide (0.55 g, 1.9 mmol) and palladium on charcoal (10%, 0.2 g) were mixed in 20 ml of ethanol. The reaction flask was evacuated and flushed with hydrogen gas. After 2 h under hydrogen gas the reaction mixture was filtered through a pad of Celite and concentrated to yield the title compound in 74% yield (0.24 g). MS (ESI+) m/z 168 [M+H]$^+$. $^1$H NMR (600 MHz, DMSO-d6) δ ppm 10.63 (s, 1H) 8.56 (s, 1H) 6.98 (d, J=1.83 Hz, 1H) 6.85 (dd, J=8.09, 1.98 Hz, 1H) 6.45 (d, J=7.93 Hz, 1H) 4.76 (br. s., 4H).

Intermediate 2

Methyl 2-(4-bromophenyl)-1H-benzimidazole-6-carboxylate

4-Bromobenzaldehyde (1.02 g, 5.51 mmol) in DMF (30 ml) was added dropwise over 3 h to a solution of methyl 3,4-diaminobenzoate (1.02 g, 6.14 mmol) and methanesulfonic acid (100 μl) in DMF (80 ml) at 50° C. The mixture was stirred overnight at 50° C. The mixture was poured over ice and filtered. The solid material was dissolved in EtOAc and MeOH and silica gel was added. The solvents were evaporated and the dry silica applied on a flash column which was eluted with 10-30% EtOAc in toluene. Yield: 1.15 g (63%); pale yellow solid. MS (ESI+) m/z 331/333 [M+H]$^+$. HPLC purity: 100%

Intermediate 3

Methyl 2-(4-bromo-3-fluorophenyl)-1H-benzimidazole-6-carboxylate

4-Bromo-3-fluorobenzaldehyde (100 mg, 0.492 mmol) in DMF (2 ml) was added drop-wise (2 h) to a solution of methyl 3,4-diaminobenzoate (81.8 mg, 0.492 mmol) and $MeSO_3H$ (2 μl) in DMF (8 ml) at 50° C. The mixture was allowed to stir at 50° C. overnight. The volume was reduced by evaporation to about 1 ml and water was added. The precipitate was isolated by centrifugation was washed twice with water. The solid material was dissolved in EtOAc, dried ($MgSO_4$) and evaporated. Yield: 160 mg (93%); yellow solid. The material was used without further purifications. MS (ESI+) m/z 349/351 [M+H]$^+$. HPLC purity: 95%

Intermediate 4

Methyl 2-(4'-formylbiphenyl-4-yl)-1H-benzimidazole-6-carboxylate

Pd(dppf)Cl$_2$ (9 mg) was added to a nitrogen flushed tube containing methyl 2-(4-bromophenyl)-1H-benzimidazole-6-carboxylate, INTERMEDIATE 2 (206 mg, 0.623 mmol), 4-formylphenylboronic acid (140 mg, 0.935 mmol) and potassium carbonate (172 mg, 1.25 mmol) in toluene/MeOH (1:1, 5 ml). The mixture was heated at 100° C. for 30 min in a microwave reactor. White solid precipitated. The solid material was washed with MeOH and water and dried at high vacuum. Yield: 183 mg (82%); white solid. MS (ESI+) m/z 357 [M+H]$^+$. HPLC purity: 100%. $^1$H NMR (600 MHz, DMSO-d$_6$) δ ppm 13.38 (br. s., 1H), 10.09 (s, 1H), 8.34 (d, J=8.2 Hz, 2H), 8.22 (br. s., 1H), 8.03 (d, J=8.5 Hz, 6H), 7.88 (d, J=8.2 Hz, 1H), 7.71 (br. s., 1H), 3.89 (s, 3H)

Intermediate 5

Methyl 2-(3'-formylbiphenyl-4-yl)-1H-benzimidazole-6-carboxylate

Pd(dppf)Cl$_2$ (9 mg) was added to a nitrogen flushed tube containing methyl 2-(4-bromophenyl)-1H-benzimidazole-6-carboxylate, INTERMEDIATE 2 (206 mg, 0.623 mmol), 3-formylphenylboronic acid (140 mg, 0.935 mmol) and potassium carbonate (172 mg, 1.25 mmol) in toluene/MeOH (1:1, 5 ml). The mixture was heated at 100° C. for 30 min in a microwave reactor. EtOAc and water were added. Organic layer was separated, dried (MgSO$_4$) and evaporated. Yield: 263 mg; beige solid. The material was used without further purifications. MS (ESI+) m/z 357 [M+H]$^+$. HPLC purity: 90%. $^1$H NMR (600 MHz, DMSO-d$_6$) δ ppm 3.89 (s, 3H) 7.75 (t, J=7.78 Hz, 2H) 7.87 (br. s., 1H) 7.96 (d, J=7.63 Hz, 1H) 8.01 (d, J=8.24 Hz, 2H) 8.15 (d, J=8.24 Hz, 1H) 8.32-8.37 (m, 3H) 10.13 (s, 1H) 13.36 (br. s., 1H)

Intermediate 6

2-(3-Bromophenyl)-1H-benzimidazole-6-carboxylic Acid

3-Bromo-benzaldehyde (1.8 g, 10 mmol) in DMF (50 ml) was added drop-wise (3 h) to a solution of 3,4-diaminobenzoic acid (2.0 g, 13 mmol) and MeSO$_3$H (0.2 g, 2 mmol) in DMF (100 ml) at 90° C. The mixture was allowed to stir overnight. Water (200 ml) was added. The precipitate was isolated by filtration and washed with water and acetonitrile. Yield: 2.9 g (92%); brown solid. MS (ESI+) m/z 317 [M+H]+. HPLC purity: 100%. $^1$H NMR (600 MHz, MeOD-d$_4$) δ ppm 8.34 (s, 1H) 8.32 (t, J=1.68 Hz, 1H) 8.06-8.12 (m, 1H) 7.99 (dd, J=8.39, 1.68 Hz, 1H) 7.69-7.74 (m, 1H) 7.66 (d, J=8.55 Hz, 1H) 7.50 (t, J=7.93 Hz, 1H)

Intermediate 7

2-(4-Bromophenyl)-1H-benzimidazole-6-carboxylic Acid

The product was prepared according to the procedure described for INTERMEDIATE 6, using 4-bromobenzaldehyde (1.8 g, 10 mmol). The title compound was obtained in 61% yield (1.9 g). MS (ESI+) m/z 317 [M+H]$^+$. HPLC purity: 99%. $^1$H NMR (600 MHz, MeOD-d$_4$) δ ppm 8.33 (br. s., 1H) 8.02-8.06 (m, 2H) 7.99 (dd, J=8.55, 1.53 Hz, 1H) 7.72-7.79 (m, 2H) 7.66 (d, 1H)

Intermediate 8

2-(5-Bromofuran-2-yl)-1H-benzimidazole-6-carboxylic Acid

The product was prepared according to the procedure described for INTERMEDIATE 6, using 5-bromo-2-furaldehyde (0.52 g, 3.0 mmol), 3,4-diaminobenzoic acid (0.59 g, 3.9 mmol) and MeSO$_3$H (0.06 g, 0.6 mmol) using a modified workup. The reaction mixture was diluted with water and ethyl acetate. The organic phase was washed with brine, dried over MgSO$_4$, filtered and concentrated. The residue was recrystallized from water/acetonitrile. The title compound was obtained in 67% yield (0.62 g). MS (ESI+) m/z 307 [M+H]$^+$. HPLC purity: 100%. $^1$H NMR (600 MHz, MeOD-d$_4$) δ ppm 8.29 (s, 1H) 7.98 (dd, J=8.55, 1.53 Hz, 1H) 7.62 (d, J=8.24 Hz, 1H) 7.25 (d, J=3.36 Hz, 1H) 6.71 (d, 1H)

Intermediate 9

2-(5-Bromothiophen-2-yl)-1H-benzimidazole-6-carboxylic Acid

The product was prepared according to the procedure described for INTERMEDIATE 6, using 5-bromo-2-thiophenecarboxaldehyde (0.57 g, 3.0 mmol), 3,4-diaminobenzoic acid (0.59 g, 3.9 mmol) and MeSO$_3$H (0.06 g, 0.6 mmol) using a modified workup. The reaction mixture was diluted with water and ethyl acetate. The organic phase was washed with brine, dried over MgSO$_4$, filtered and concentrated. The residue was recrystallized from water/acetonitrile. MS (ESI+) m/z 323 [M+H]$^+$. HPLC purity: 95%. $^1$H NMR (600 MHz, DMSO-d6) δ ppm 7.70 (d, J=3.66 Hz, 1H) 7.40 (d, J=3.97 Hz, 1H)

Intermediate 10

2-Bromo-1H-benzimidazole-6-carboxylic Acid

Step 1. Methyl 2-oxo-2,3-dihydro-1H-1,3-benzimidazole-5-carboxylate (1.3 g, 6.6 mmol), pyridine hydrobromide (1.0 g, 6.6 mmol) and phosphorous oxybromide (3.7 g, 13 mmol) were mixed in EtOAc (100 ml). The reaction mixture was stirred at reflux for 7 d. Water was added. The organic phase was washed with NaHCO$_3$ (sat., aq), dried over MgSO$_4$, filtered and concentrated. The intermediate methyl 2-bromo-1H-benzimidazole-6-carboxylate was obtained in 100% yield (1.6 g). MS (ESI+) m/z 255 [M+H]$^+$. HPLC purity: 95%. $^1$H NMR (600 MHz, MeOD-d$_4$) δ ppm 8.21 (s, 1H) 7.96 (dd, J=8.55, 1.53 Hz, 1H) 7.58 (d, J=8.55 Hz, 1H) 3.93 (s, 3H)

Step 2. The ester from above was dissolved in 0.5 M NaOH (50 ml). The reaction mixture was stirred at 50° C. for 2 h. 1 M phosphonic acid was added until pH~5 followed by EtOAc. The organic phase was washed with brine, dried over MgSO$_4$, filtered and concentrated. The title compound was obtained as a white solid (1.2 g, 76%). MS (ESI+) m/z 241 [M+H]$^+$. HPLC purity: 98%. $^1$H NMR (600 MHz, MeOD-d$_4$) δ ppm 8.25 (br. s., 1H) 7.97 (d, J=8.55 Hz, 1H) 7.57 (br. s., 1H)

Intermediate 11

Methyl 4,5-diamino-2-fluorobenzoate tert-Butylamine (420 μl, 2.00 mmol) in THF (5 ml) was added dropwise to a solution of methyl 2,4-difluoro-5-nitrobenzoate (826 mg, 2.80 mmol) and DIEPA (1.29 ml, 7.6 mmol) in THF (10 ml) at 0° C. and the mixture slowly reached room temperature overnight. One more portion of tert-butylamine (420 μl, 2.00 mmol) was added and the mixture stirred at room temperature for 2 h. EtOAc and water were added. The organic layer was washed with sat. NaHCO$_3$ and evaporated. The residue was purified by flash chromatography using toluene as eluent. Yield: 731 mg; yellow solid. methyl 4-(tert-butylamino)-2-fluoro-5-nitrobenzoate. MS(ESI+) m/z 271 [M+H]$^+$. HPLC purity: 100%. $^1$H NMR (600 MHz, DMSO-d$_6$) δ ppm 8.68 (d, J=7.9 Hz, 1H), 8.53 (s, 1H), 7.02 (d, J=14.0 Hz, 1H), 3.82 (s, 3H), 1.47 (s, 9H).

The material from above (366 mg, 1.35 mmol) was stirred in DCM (2 ml) and TFA (2 ml) for 2 h at room temperature before TFA (1 ml) was added and the suspension stirred for 1 h at. Most of the solvents were evaporated and sat. NaHCO$_3$ and EtOAc were added. The organic layer was dried (MgSO4) and evaporated. Yield: 294 mg; yellow solid. Methyl 4-amino-2-fluoro-5-nitrobenzoate. $^1$H NMR (600 MHz, DMSO-d$_6$) δ ppm 8.59 (d, J=7.6 Hz, 1H), 8.07 (br. s., 2H), 6.78 (d, J=13.4 Hz, 1H), 3.81 (s, 3H).

10% palladium on charcoal was added to methyl 4-amino-2-fluoro-5-nitrobenzoate in MeOH, and the mixture stirred under an atmosphere of H$_2$ for 3 h, filtered through Celite and concentrated. Methyl 4,5-diamino-2-fluorobenzoate. MS (ESI+) m/z 185 [M+H]$^+$. HPLC purity: 93%.

Intermediate 12

3-Amino-N-hydroxy-4-(methylamino)benzamide

Step 1. Triethylamine (3.0 g, 30 mmol), HATU (4.2 g, 11 mmol) and 4-(methylamino)-3-nitrobenzoic acid (2.0 g, 10 mmol) were mixed in 100 ml of DMF at ambient temperature. After 15 minutes O-benzylhydroxylamine hydrochloride (1.76 g, 11 mmol) was added. Brine and ethyl acetate were added after 2 h. The organic phase was washed with water, saturated NaHCO$_3$ (aq) and brine, dried over MgSO$_4$, filtered and concentrated. The residue was recrystallized from water/methanol. The intermediate 4-amino-N-(benzyloxy)-3-nitrobenzamide was obtained as a yellow solid. MS (ESI+) m/z 302 [M+H]$^+$. HPLC purity: 100%. $^1$H NMR (600 MHz, DMSO-d6) δ ppm 11.78 (s, 1H) 8.55 (d, J=2.14 Hz, 1H) 8.46 (q, J=4.58 Hz, 1H) 7.90 (dd, J=9.00, 1.98 Hz, 1H) 7.27-7.50 (m, 5H) 7.05 (d, J=9.16 Hz, 1H) 4.91 (s, 2H) 2.99 (d, J=4.88 Hz, 3H).

Step 2. 4-Amino-N-(benzyloxy)-3-nitrobenzamide and palladium on charcoal (10%, catalytical amount) were mixed in 20 ml of ethanol. The reaction flask was evacuated and flushed with hydrogen gas. After 2 h under hydrogen gas the reaction mixture was filtered through a pad of Celite and concentrated to yield the title compound. MS (ESI+) m/z 182 [M+H]$^+$. HPLC purity: 95%. $^1$H NMR (600 MHz, DMSO-d6) δ ppm 10.66 (s, 1H) 8.57 (br. s., 1H) 6.91-7.05 (m, J=4.27, 2.14, 2.14, 1.83 Hz, 2H) 6.25-6.38 (m, 1H) 5.08 (br. s., 1H) 4.61 (br. s., 2H) 2.74 (s, 3H)

Example 1

2-(3-Chlorophenyl)-N-hydroxy-1H-benzimidazole-6-carboxamide

General Procedure A

A solution of 3,4-diaminobenzoic acid (15.2 mg, 0.100 mmol) and p-TSA (3.8 mg, 0.020 mmol) in DMF (1 mL) was heated at 80° C. To the mixture was added 3-chlorobenzaldehyde (11 μL, 0.100 mmol) in DMF (0.4 mL) in 4 portions, with ca. 1 h between each addition. After additional 1 h of stirring at 80° C., most of the DMF was removed on a rotary evaporator and then 1 M NaOH was added (1.5 ml, 1.5 mmol). To facilitate precipitation the pH was adjusted to 5-6 using 6 M HCl and 6 M NaOH. The mixture was centrifuged (3000 rpm, 5 min) and the supernatant was removed. The pellet was washed twice with water and then dried in vacuum giving 2-(3-chlorophenyl)-1H-benzimidazole-6-carboxylic acid in 98% yield (26.7 mg, 99% purity) which was used without further purification. $^1$H NMR (600 MHz, CD$_3$OD) δ ppm 7.55-7.59 (m, 2H) 7.67 (d, J=8.39 Hz, 1H) 8.00 (dd, J=8.39, 1.53 Hz, 1H) 8.03-8.08 (m, 1H) 8.16-8.18 (m, 1H) 8.34 (br. s., 1H). MS (ESI$^+$) m/z 273 [M+H]$^+$.

A solution of 2-(3-chlorophenyl)-1H-benzimidazole-6-carboxylic acid from above (13.6 mg, 0.05 mmol), SOCl$_2$ (300 μL, 4.1 mmol) and a catalytic amount of DMF was heated at 65° C. for 2.5 h. Hexane was added, and the solvents were removed by evaporation. The residue was dissolved in THF (900 μL). Triethylamine (21 μL, 0.15 mmol) and hydroxylamine (50% w/w in water, 31 μL, 0.50 mmol) were added. The reaction mixture was stirred at room temperature for 1 h and then concentrated on the rotary evaporator. The residue was dissolved in a mixture of MeOH, DMSO and H$_2$O with 30 μL TFA, and then purified by preparative HPLC giving 2-(3-chlorophenyl)-N-hydroxy-1H-benzimidazole-6-carboxamide in 70% yield (10.0 mg, 0.035 mmol).

Example 20

2-[4-(Acetylamino)phenyl]-N-hydroxy-1H-benzimidazole-6-carboxamide

General Procedure B 3,4-Diaminobenzoic acid (15 mg, 0.10 mmol) and methanesulfonic acid (2 mg, 0.02 mmol) were mixed in 500 μl of DMF. The mixture was stirred at 90° C. in an open to air vial. 4-Acetamidobenzaldehyde (0.075 mmol) in DMF (500 μl) was added in portions of 50 μl over 2 h. The reaction mixture was stirred for an additional 3 h and purified with reversed phase chromatography (ACE C8, 5 μm, 21×100 mm, flow 25 ml/min, gradient: water+0.1% TFA/acetonitrile over 12 minutes). The pure fractions were concentrated and dried in vacuum. The intermediate from above was dissolved in acetonitrile (500 μl) and triethylamine (15 mg, 0.15 mmol) and propylphosphonic anhydride (50% in EtOAc, 64 μl, 0.10 mmol) were added. After 30 minutes O-(tetrahydropyran-2-yl)-hydroxylamine (18 mg, 0.15 mmol) was added. The reaction mixture was stirred at 50° C. for 2 h. TFA (1 M, 300 μl) was added. After 2 h at 50° C. the deprotection was complete. The reaction mixture was purified with reversed phase chromatography (ACE C8, 5 μm, 21×100 mm, flow 25 ml/min, gradient: water+0.1% TFA/acetonitrile over 12 minutes). The title compound was obtained after concentration of the pure fractions Example 80

2-(4-Ethynylphenyl)-N-hydroxy-1H-benzimidazole-6-carboxamide

General Procedure C 3,4-Diamino-N-hydroxybenzamide, INTERMEDIATE 1 (8 mg, 0.050 mmol) and methanesulfonic acid (0.5 mg, 0.005 mmol) were mixed in 500 μl of DMF. The mixture was stirred at 50° C. in an open to air vial. 4-Ethynylbenzaldehyde (0.050 mmol) in 200 μl of DMF was added in portions of 20 μl over 2 h. The reaction mixture was stirred overnight and purified with reversed phase chromatography (Kinetex C18, 5 μm, 21×100 mm, flow 25 ml/min, gradient: water+0.1% TFA/acetonitrile over 15 minutes). The title compound was obtained after concentration of the pure fractions.

Example 121

N-Hydroxy-2-(4-propoxyphenyl)-1H-benzimidazole-6-carboxamide

General Procedure D

A mixture of 4-hydroxybenzaldehyde (12 mg, 0.10 mmol), potassium carbonate (41 mg, 0.30 mmol) and 1-iodopropane (0.10 mmol) was stirred in 700 μl of DMF at 50° C. for 2 days. The reaction mixture was diluted with EtOAc (5 ml) and filtered through a pad of hydromatrix (diatomaceous earth). The eluate was concentrated to ~200 μl. The intermediate alkyloxybenzaldehyde was used as such in preparation of the title compound according to GENERAL PROCEDURE C Example 145

2-(4-Chlorobenzyl)-N-hydroxy-1H-benzimidazole-6-carboxamide

General Procedure E

4-Chlorophenylacetyl chloride (0.075 mmol) in acetonitrile (500 μl) was added in 50 μl portions over 1 h at ambient temperature to a solution of 3,4-diaminobenzoic acid (15 mg, 0.10 mmol) of acetonitrile/DMF (1:1, 500 μl). Upon completed addition, acetic acid (200 μl) was added. The reaction was stirred at 80° C. overnight to complete the cyclization. The reaction mixture was purified with reversed phase chromatography (ACE C8, 5 μm, 21×100 mm, flow 25 ml/min, gradient: water+0.1% TFA/acetonitrile over 12 minutes). The pure fractions were concentrated and dried in vacuum.

The isolated carboxylic acid was dissolved in acetonitrile (500 μl). Triethylamine (15 mg, 0.15 mmol) and propylphosphonic anhydride (50% in EtOAc, 64 μl, 0.10 mmol) were added. After 30 minutes at room temperature, O-(tetrahydropyran-2-yl)-hydroxylamine (18 mg, 0.15 mmol) was added. The reaction mixture was stirred at 50° C. for 2 h before TFA (1 M in water, 300 μl) was added. After 2 h at 50° C. the deprotection was complete. The reaction mixture was purified with reversed phase chromatography (ACE C8, 5 μm, 21×100 mm, flow 25 ml/min, gradient: water+0.1% TFA/acetonitrile over 12 minutes). The title compound was obtained after concentration of the pure fractions.

Example 148

N-Hydroxy-2-(4'-methoxybiphenyl-3-yl)-1H-benzimidazole-6-carboxamide

General Procedure F

Pd(dppf)Cl$_2$ (ca 2 mg) was added to a mixture of INTERMEDIATE 6 (0.075 mmol), triethylamine (15 mg, 0.15 mmol), water (100 µl) and 4-methoxyphenylboronic acid (0.090 mmol) in acetonitrile (1 ml). The mixture was stirred at 80° C. in a sealed tube overnight. The reaction mixture was acidified with TFA, filtered and purified with reversed phase chromatography (ACE C8, 5 µm, 21×100 mm, flow 25 ml/min, gradient: water+0.1% TFA/acetonitrile over 12 minutes). The pure fractions were concentrated and dried in vacuum. The isolated carboxylic acid was dissolved in acetonitrile (500 µl) and triethylamine (15 mg, 0.15 mmol) and propylphosphonic anhydride (50% in EtOAc, 64 µl, 0.10 mmol) were added. After 30 minutes O-(tetrahydropyran-2-yl)-hydroxylamine (18 mg, 0.15 mmol) was added. The reaction mixture was stirred at 50° C. for 2 h. TFA (1 M, 300 µl) was added. After 2 h at 50° C. was the deprotection complete. The reaction mixture was purified with reversed phase chromatography (ACE C8, 5 µm, 21×100 mm, flow 25 ml/min, gradient: water+0.1% TFA/acetonitrile over 12 minutes). The title compound was obtained after concentration of the pure fractions.

Example 150

N-Hydroxy-2-(4'-methoxybiphenyl-4-yl)-1H-benzimidazole-6-carboxamide

General Procedure G

The title compound was obtained according to GENERAL PROCEDURE F using INTERMEDIATE 7 and 4-methoxyphenylboronic acid.

Example 152

N-Hydroxy-2-[4-(methylsulfonyl)phenyl]-1H-benzimidazole-6-carboxamide

General Procedure H

The title compound was obtained according to GENERAL PROCEDURE F using INTERMEDIATE 10 and 4-methanesulfonylphenylboronic acid.

Example 153

N-Hydroxy-2-(5-phenylfuran-2-yl)-1H-benzimidazole-6-carboxamide

General Procedure I

The title compound was obtained according to GENERAL PROCEDURE F using INTERMEDIATE 8 and phenylboronic acid.

Example 176

2-[5-(2-Fluorophenyl)thiophen-2-yl]-N-hydroxy-1H-benzimidazole-6-carboxamide

General Procedure J

The title compound was obtained according to GENERAL PROCEDURE F using INTERMEDIATE 9 and 2-fluorophenylboronic acid.

Example 180

2-(2-Fluorobiphenyl-4-yl)-N-hydroxy-1H-benzimidazole-6-carboxamide

General Procedure K

Pd(dppf)Cl$_2$ (ca 2 mg) was added to a nitrogen flushed tube containing methyl 2-(4-bromo-3-fluorophenyl)-1H-benzimidazole-6-carboxylate, INTERMEDIATE 3 (26.5 mg, 76 µmol), phenylboronic acid (13.9 mg, 114 µmol) and potassium carbonate (21 mg, 152 µmol) in toluene (1 ml) and MeOH (1 ml). The mixture was heated in a microwave reactor for 20 min at 100° C. The mixture was diluted with toluene (5 ml) and filtered through silica (500 mg) and eluted with 10% MeOH in toluene. Solvents were evaporated and the crude material stirred in freshly prepared hydroxylamine potassium salt solution in MeOH (1.7 M, 1.5 ml) for 1 h at ambient temperature. The mixture was quenched with AcOH (0.5 ml) and product isolated by reversed phase chromatography (ACE 5 C8, 5 µm, 30×100 mm, flow 40 ml/min, gradient 0.1% TFA in water/acetonitrile over 15 minutes). Yield: 7.2 mg (27%); white solid.

Example 184

2-(3'-{[(cis)-2,6-Dimethylmorpholin-4-yl]methyl}biphenyl-4-yl)-N-hydroxy-1H-benzimidazole-6-carboxamide trifluoroacetate General Procedure L cis-2,6-Dimethylmorpholine (18.9 mg, 0.164 mmol) was added to a solution of methyl 2-(3'-formylbiphenyl-4-yl)-H-benzimidazole-6-carboxylate, INTERMEDIATE 5 (29.2 mg. 0.0819 mmol) and AcOH (3 µl) in THF (1 ml). The mixture was stirred at rt for 1 h before sodium triacetoxyborohydride (43 mg, 0.205 mmol) was added and stirring continued for 30 min. MeOH was added and the ester intermediate purified with reversed phase chromatography (Gemini-NX C18, 5 µm, 21×50 mm, flow 25 ml/min, gradient: water (50 mM NH$_4$HCO$_3$ pH 10)/acetonitrile over 12 minutes). Yield: 29.5 mg (78%); colourless oil.

The ester from above was dissolved in MeOH (1 ml). KOH (5 mg) and 50% hydroxylamine in water (0.5 ml) were added and the mixture was heated at 60° C. for 1.5 h, quenched with AcOH (0.5 ml) and purified by reversed phase chromatography (Kinetex C18, 5 µm, 21.2×100 mm, flow 25 ml/min, gradient 0.1% TFA in water/acetonitrile over 15 minutes). Yield: 20.1 mg (55%); white solid.

Example 189

N-Hydroxy-2-(trifluoromethyl)-1H-benzimidazole-6-carboxamide 3,4-Diaminobenzoic acid (15 mg, 0.10 mmol) and 1 M TFA (aq) (500 µl) was stirred at 90° C. for 3 h. The reaction mixture was purified with reversed phase chromatography (ACE C8, 5 µm, 21×100 mm, flow 25 ml/min, gradient: water+0.1% TFA/acetonitrile over 12 minutes). The pure fractions were concentrated and dried in vacuum. The residue (2-(trifluoromethyl)-1H-benzimidazole-6-carboxylic acid, MS (ESI+) m/z 231 [M+H]$^+$) was mixed in 500 µl of acetonitrile together with triethylamine (15 mg, 0.15 mmol) and propylphosphonic anhydride (50% in EtOAc, 64 µl, 0.10 mmol). After 30 minutes O-(tetrahydropyran-2-yl)-hydroxylamine (18 mg, 0.15 mmol) was added. The reaction mixture was stirred at 50° C. for 2 h. TFA (1 M in water, 300 µl) was added. After 2 h at 50° C. was the deprotection complete. The reaction mixture was purified with reversed phase chromatography (ACE C8, 5 µm, 21×100 mm, flow 25 ml/min, gradient: water+0.1% TFA/acetonitrile over 12 minutes). The title compound was obtained after concentration of the pure fractions.

Example 190

N-Hydroxy-2-[4'-(morpholin-4-ylmethyl)biphenyl-4-yl]-1H-benzimidazole-6-carboxamide trifluoroacetate Sodium triacetoxyborohydride (18.9 mg, 0.0892 mmol) was added to a solution of methyl 2-(4'-formylbiphenyl-4-yl)-1H-benzimidazole-6-carboxylate, INTERMEDIATE 4 (15.9 mg, 0.0446 mmol) and morpholine (6.7 mg, 0.0769 mmol) in DMF (0.5 ml). The mixture was stirred at ambient temperature overnight. Water was added and solvents evaporated. Freshly prepared hydroxylamine potassium salt in MeOH (ca 1.7 M, 1.5 ml) was added and the mixture stirred at ambient temperature overnight. AcOH (500 µl) was added and the product isolated by reversed phase chromatography (ACE 5 C8, 5 µm, 30×100 mm, flow 40 ml/min, gradient 0.1% TFA in water/acetonitrile over 15 minutes). Yield: 3.2 mg (13%); white solid.

Example 191

N-Hydroxy-2-(4'-{[(3-methoxypropyl)amino]methyl}biphenyl-4-yl)-1H-benzimidazole-6-carboxamide trifluoroacetate Sodium triacetoxyborohydride (18.9 mg, 0.0892 mmol) was added to a solution of methyl 2-(4'-formylbiphenyl-4-yl)-1H-benzimidazole-6-carboxylate, INTERMEDIATE 4 (16.2 mg, 0.0455 mmol) and 3-methoxypropylamine (8 µl, 0.0774 mmol) in DMF (0.5 ml). The mixture was stirred at ambient temperature overnight, diluted with MeOH, filtered and solvents evaporated. Freshly prepared hydroxylamine potassium salt in MeOH (ca 1.7 M, 2 ml) was added and the mixture was stirred at ambient temperature overnight. AcOH (500 µl) was added and the product isolated by reversed phase chromatography (ACE 5 C8, 5 µm, 30×100 mm, flow 40 ml/min, gradient 0.1% TFA in water/acetonitrile over 15 minutes). Yield: 10.5 mg (54%); beige solid.

Example 192 and 193

2-(4'-Formylbiphenyl-4-yl)-N-hydroxy-1H-benzimidazole-6-carboxamide (EXAMPLE 192) and N-hydroxy-2-{4'-[(E)-(hydroxyimino)methyl]biphenyl-4-yl}-1H-benzimidazole-6-carboxamide (EXAMPLE 193)

Methyl 2-(4'-formylbiphenyl-4-yl)-1H-benzimidazole-6-carboxylate, INTERMEDIATE 4 (12.8 mg, 0.0359 mmol) was stirred with freshly prepared hydroxylamine potassium salt in MeOH (ca 1.7 M, 1.5 ml) for 2 h. Two products were isolated by reversed phase chromatography (ACE 5 C8, 5 µm, 30×100 mm, flow 40 ml/min, gradient 0.1% TFA in water/acetonitrile over 15 minutes). 2-(4'-formylbiphenyl-4-yl)-N-hydroxy-1H-benzimidazole-6-carboxamide: Yield: 2.4 mg (19%); white solid. MS(ESI+) m/z 358 [M+H]$^+$. HPLC purity: 95%. And N-hydroxy-2-{4'-[(E)-(hydroxyimino)methyl]biphenyl-4-yl}-1H-benzimidazole-6-carboxamide: Yield: 5.2 mg (39%); yellow solid.

Example 194

2-[4'-(Aminomethyl)biphenyl-4-yl]-N-hydroxy-1H-benzimidazole-6-carboxamide trifluoroacetate Pd(dppf)Cl$_2$ (ca 2 mg) was added to a nitrogen flushed tube containing methyl 2-(4-bromophenyl)-1H-benzimidazole-6-carboxylate, INTERMEDIATE 2 (25 mg, 0.0755 mmol), (4-aminomethylphenyl)boronic acid (21.4 mg, 0.114 mmol) and potassium carbonate (21 mg, 0.152 mmol) in toluene (1 ml) and MeOH (1 ml). The mixture was heated at 100° C. for 45 min in a microwave reactor and diluted with toluene and filtered through a plug of silica (0.5 g). Solvents were evaporated and freshly prepared hydroxylamine potassium salt in MeOH (ca 1.7 M, 2 ml) was added and the mixture heated at 50° C. for 1 h. AcOH (500 µl) was added and the title compound isolated by reversed phase chromatography (ACE 5 C8, 5 µm, 30×100 mm, flow 40 ml/min, gradient 0.1% TFA in water/acetonitrile over 15 minutes). Yield: 3.9 mg (11%); white solid.

Example 195

2-[3'-(Dimethylcarbamoyl)biphenyl-4-yl]-N-hydroxy-1H-benzimidazole-6-carboxamide Pd(dppf)Cl$_2$ (ca 2 mg) was added to a nitrogen flushed tube containing methyl 2-(4-bromophenyl)-1H-benzimidazole-6-carboxylate, INTERMEDIATE 2 (25 mg, 0.0755 mmol), [3-(N,N-dimethylaminocarbonyl)phenyl]boronic acid (22.0 mg, 0.114 mmol) and potassium carbonate (21 mg, 0.152 mmol) in toluene (1 ml) and MeOH (1 ml). The mixture was heated at 100° C. for 45 min in a microwave reactor and diluted with toluene and filtered through a plug of silica (0.5 g). Solvents were evaporated and freshly prepared hydroxylamine potassium salt in MeOH (ca 1.7 M, 2 ml) was added and the mixture heated at 50° C. for 1 h. The mixture was quenched with AcOH (300 µl) and the product isolated by reversed phase chromatography (ACE 5 C8, 5 µm, 30×100 mm, flow 40 ml/min, gradient 0.1% TFA in water/acetonitrile over 15 minutes). Yield: 13.1 mg (44%); white solid.

Example 196

N-Hydroxy-2-[4'-(hydroxymethyl)biphenyl-4-yl]-1H-benzimidazole-6-carboxamide

Pd(dppf)Cl$_2$ (ca 2 mg) was added to a nitrogen flushed tube containing methyl 2-(4-bromophenyl)-1H-benzimidazole-6-carboxylate, INTERMEDIATE 2 (25 mg, 0.0755 mmol), 4-(hydroxymethyl)phenylboronic acid (17.3 mg, 0.114 mmol) and potassium carbonate (21 mg, 0.152 mmol) in toluene (1 ml) and MeOH (1 ml). The mixture was heated at 100° C. for 45 min in a microwave reactor and diluted with toluene and filtered through a plug of silica (0.5 g).

Solvents were evaporated and freshly prepared hydroxylamine potassium salt in MeOH (ca 1.7 M, 2 ml) was added and the mixture heated at 50° C. for 1 h before quench with AcOH (300 µl) and the product isolated by reversed phase chromatography (ACE 5 C8, 5 µm, 30×100 mm, flow 40 ml/min, gradient 0.1% TFA in water/acetonitrile over 15 minutes). Yield: 4.2 mg (15%); beige solid.

Example 197 and 198

N-Hydroxy-2-[4'-(pyrrolidin-1-ylmethyl)biphenyl-4-yl]-1H-benzimidazole-6-carboxamide trifluoroacetate (EXAMPLE 197) and 2-{4'-[(dimethylamino)methyl]biphenyl-4-yl}-N-hydroxy-1H-benzimidazole-6-carboxamide trifluoroacetate (EXAMPLE 198)

Sodium triacetoxyborohydride (32 mg, 0.150 mmol) was added to a solution of methyl 2-(4'-formylbiphenyl-4-yl)-1H-benzimidazole-6-carboxylate, INTERMEDIATE 4 (26.7 mg, 0.075 mmol) and pyrrolidine (8.0 mg, 0.113 mmol) in DMF (1 ml) and the mixture was stirred at ambient temperature overnight. Two intermediates were isolated with reversed phase chromatography (Gemini-NX C18, 5 µm, 21×50 mm, flow 25 ml/min, gradient: water (50 mM NH$_4$HCO$_3$ pH 10)/acetonitrile over 12 minutes).
methyl 2-[4'-(pyrrolidin-1-ylmethyl) biphenyl-4-yl]-1H-benzimidazole-6-carboxylate
Yield: 7.9 mg (25%); white solid
methyl 2-{4'-[(dimethylamino)methyl]biphenyl-4-yl}-1H-benzimidazole-6-carboxylate
Yield: 15.5 mg (54%); white solid.
To the two esters from above were added 50% hydroxylamine in water (0.5 ml), MeOH (1 ml) and KOH (5 mg). The mixtures were heated at 60° C. for 1.5 h, quenched with AcOH (500 µl) and the products purified by reversed phase chromatography (Kinetex C18, 5 µm, 21.2×100 mm, flow 25 ml/min, gradient 0.1% TFA in water/acetonitrile over 15 minutes)
N-hydroxy-2-[4'-(pyrrolidin-1-ylmethyl) biphenyl-4-yl]-H-benzimidazole-6-carboxamide trifluoroacetate. Yield: 6.9 mg (68%); white solid.
2-{4'-[(dimethylamino)methyl]biphenyl-4-yl}-N-hydroxy-1H-benzimidazole-6-carboxamide trifluoroacetate. Yield: 13.3 mg (66%); white solid.

Example 199

2-(4'-{[Bis(2-methylpropyl)amino]methyl}biphenyl-4-yl)-N-hydroxy-1H-benzimidazole-6-carboxamide trifluoroacetate Sodium triacetoxyborohydride (32 mg, 0.150 mmol) was added to a solution of methyl 2-(4'-formylbiphenyl-4-yl)-1H-benzimidazole-6-carboxylate, INTERMEDIATE 4 (26.7 mg, 0.075 mmol) and diisobutylamine (14.6 mg, 0.113 mmol) in DMF (1 ml) and the mixture was stirred at ambient temperature overnight. Solvents were evaporated and freshly prepared hydroxylamine potassium salt solution (2 ml) added. After 1 h the temperature was raised to 50° C. and stirring continued. After 2 h heating was discontinued and mixture stirred at rt for 3 d. The intermediate was isolated by reversed phase chromatography (Kinetex C18, 5 µm, 21.2×100 mm, flow 25 ml/min, gradient 0.1% TFA in water/acetonitrile over 15 minutes) ((2-(4'-{[bis(2-methylpropyl)amino]methyl}biphenyl-4-yl)-1H-benzimidazole-6-carboxylic acid trifluoroacetate): yield: 14.3 mg (33%).
HATU (19.1 mg, 50 µmol) was added to the material from above (14.3 mg, 25 µmol) and DIPEA (13 µl, 75 µmol) in MeCN (1 ml) and DMF (0.5 ml). O-Tetrahydropyran-2-yl)-hydroxylamine (5.6 mg, 50 µmol) was added and the mixture stirred at ambient temperature for 2 h. TFA (300 µl) and water (150 µl) were added and the mixture heated at 50° C. for 1 h. The compound was purified by reversed phase chromatography (Kinetex C18, 5 µm, 21.2×100 mm, flow 25 ml/min, gradient 0.1% TFA in water/acetonitrile over 15 minutes). Yield: 11.9 mg (81%); beige solid.

Example 200

N-Hydroxy-2-[4'-(piperidin-1-ylmethyl)biphenyl-4-yl]-1H-benzimidazole-6-carboxamide trifluoroacetate Sodium triacetoxyborohydride (29.7 mg, 0.140 mmol) was added to a solution of methyl 2-(4'-formylbiphenyl-4-yl)-1H-benzimidazole-6-carboxylate, INTERMEDIATE 4 (25.0 mg, 0.0701 mmol) and piperidine (10 mg, 0.105 mmol) in THF (2 ml) and the mixture was stirred at ambient temperature overnight. The intermediate ester was isolated with reversed phase chromatography (Gemini-NX C18, 5 µm, 21×50 mm, flow 25 ml/min, gradient: water (50 mM NH$_4$HCO$_3$ pH 10)/acetonitrile over 12 minutes). Yield: 12.0 mg.
To the ester from above were added MeOH (1 ml), KOH (5 mg) and 50% hydroxylamine in water (0.5 ml). The mixture was heated at 60° C. for 1.5 h before quenched with AcOH (0.5 ml) and purified by reversed phase chromatography (Kinetex C18, 5 µm, 21.2×100 mm, flow 25 ml/min, gradient 0.1% TFA in water/acetonitrile over 15 minutes). Yield: 10.5 mg (69%); white solid.

Example 201

2-(4'-{cis)-2,6-Dimethylmorpholin-4-yl]methyl}biphenyl-4-yl)-N-hydroxy-1H-benzimidazole-6-carboxamide trifluoroacetate Sodium triacetoxyborohydride (29.7 mg, 0.140 mmol) was added to a solution of methyl 2-(4'-formylbiphenyl-4-yl)-1H-benzimidazole-6-carboxylate, INTERMEDIATE 4 (25.0 mg, 0.0701 mmol) and 2,6-cis-dimethylmorpholine (12.1 mg, 0.105 mmol) in THF (2 ml) and the mixture was stirred at ambient temperature overnight. The intermediate ester was isolated with reversed phase chromatography (Gemini-NX C18, 5 µm, 21×50 mm, flow 25 ml/min, gradient: water (50 mM NH$_4$HCO$_3$ pH 10)/acetonitrile over 12 minutes). Yield: 2.5 mg.
To the ester from above were added MeOH (1 ml), KOH (5 mg) and 50% hydroxylamine in water (0.5 ml). The mixture was heated at 60° C. for 1.5 h before quenched with AcOH (0.5 ml) and purified by reversed phase chromatography (Kinetex C18, 5 µm, 21.2×100 mm, flow 25 ml/min, gradient 0.1% TFA in water/acetonitrile over 15 minutes). Yield: 2.2 mg (73%); white solid.

Example 202

N-Hydroxy-2-[3'-(hydroxymethyl)biphenyl-4-yl]-1H-benzimidazole-6-carboxamide

Pd(dppf)Cl$_2$ (15 mg, 0.02 mmol) was added to a nitrogen flushed tube containing 4-bromobenzaldehyde (326 mg, 1.76 mmol), 3-(hydroxymethyl)phenylboronic acid (321 mg, 2.11 mmol) and potassium carbonate (487 mg, 3.52 mmol) in toluene (2 ml) and MeOH (2 ml). The mixture was heated in microwave reactor at 100° C. for 45 min, solvents evaporated and residue purified by flash chromatography using hexanes/EtOAc 1:1 as eluent. Yield: 296 mg (79%); colourless oil. 3'-(hydroxymethyl)biphenyl-4-carbaldehyde. MS(ESI+) m/z 213 [M+H]$^+$. HPLC purity: 99%. $^1$H NMR (600 MHz, DMSO-$d_6$) δ ppm 4.59 (d, 2H) 5.28 (t, J=5.65 Hz, 1H) 7.40 (d, J=7.94 Hz, 1H) 7.47 (t, J=7.63 Hz, 1H) 7.64 (d, J=7.63 Hz, 1H) 7.71 (s, 1H) 7.91 (d, J=8.24 Hz, 2H) 8.00 (d, J=8.54 Hz, 2H) 10.06 (s, 1H).

The aldehyde from above (12.2 mg, 0.058 mmol), p-benzoquinone (5.4 mg, 0.0500 mmol) and 3,4-diamino-N-hydroxybenzamide, INTERMEDIATE 1 (8 mg, 0.050 mmol) in MeOH (1 ml) was heated at 60° C. overnight before AcOH (0.5 ml) was added and title compound isolated by reversed phase chromatography (Kinetex C18, 5 μm, 21.2× 100 mm, flow 25 ml/min, gradient 0.1% TFA in water/acetonitrile over 15 minutes). Yield: 2.3 mg (13%); white solid.

Example 203

2-(3'-Carbamoylbiphenyl-4-yl)-N-hydroxy-1H-benzimidazole-6-carboxamide

Pd(dppf)Cl$_2$ (10 mg, 0.014 mmol) was added to a nitrogen flushed tube containing 4-bromobenzaldehyde (92 mg, 0.497 mmol), 3-carbamoylphenylboronic acid (98 mg, 0.597 mmol) and potassium carbonate (137 mg, 0.994 mmol) in toluene (1 ml) and MeOH (1 ml). The mixture was heated in a microwave reactor at 100° C. for 30 min. EtOAc and water was added. The organic phase was separated and concentrated. The residue was purified by flash chromatography using 50-100% EtOAc in hexanes as eluent. 4'-formylbiphenyl-3-carboxamide: Yield: 58.8 mg (52%); white solid. MS(ESI+) m/z 226 [M+H]$^+$. HPLC purity: 80%. $^1$H NMR (600 MHz, DMSO-$d_6$) δ ppm 7.47 (br. s., 1H) 7.60 (t, J=7.78 Hz, 1H) 7.86-8.01 (m, 4H) 8.01-8.06 (m, 2H) 8.14 (br. s., 1H) 8.26 (s, 1H) 10.07 (s, 1H)

The aldehyde from above (15.0 mg, 0.0666 mmol), p-benzoquinone (5.4 mg, 0.0500 mmol) and 3,4-diamino-N-hydroxybenzamide, INTERMEDIATE 1 (8 mg, 0.050 mmol) in MeOH (1 ml) was heated at 60° C. overnight before AcOH (0.5 ml) was added and title compound isolated by reversed phase chromatography (Kinetex C18, 5 μm, 21.2× 100 mm, flow 25 ml/min, gradient 0.1% TFA in water/acetonitrile over 15 minutes). Yield: 0.8 mg; white solid.

Example 204

N-Hydroxy-2-{4'-[(methylsulfonyl)amino]biphenyl-4-yl}-1H-benzimidazole-6-carboxamide Pd(dppf)Cl$_2$ (10 mg, 0.014 mmol) was added to a nitrogen flushed tube containing 4-bromobenzaldehyde (92 mg, 0.497 mmol), 4-methanesulfonylaminophenylboronic acid, pinacol ester (128 mg, 0.597 mmol) and potassium carbonate (137 mg, 0.994 mmol) in toluene (1 ml) and MeOH (1 ml). The mixture was heated in a microwave reactor at 100° C. for 30 min. EtOAc and water was added. The organic phase evaporated and residue purified by flash chromatography using 33-50% EtOAc in hexanes as eluent. Yield: 81.8 mg (60%); yellow solid. N-(4'-formylbiphenyl-4-yl)methanesulfonamide. MS (ESI+) m/z 276 [M+H]$^+$. HPLC purity: 95%. $^1$H NMR (600 MHz, DMSO-$d_6$) δ ppm 3.32 (s, 3H) 7.33 (d, J=8.85 Hz, 2H) 7.77 (d, J=8.85 Hz, 2H) 7.89 (d, J=8.24 Hz, 2H) 7.98 (d, J=8.24 Hz, 2H) 9.97 (br. s., 1H) 10.04 (s, 1H).

The aldehyde from above (18.4 mg, 0.0668 mmol), methyl 3,4-diaminobenzoate (11.1 mg, 0.668 mmol) and p-benzoquinone (7.2 mg, 0.0668 mmol) in EtOH was heated at 60° C. for 1 h and 80° C. for 3 h. Solvents were evaporated. The residue was dissolved in MeOH (1 ml) and KOH (5 mg) and 50% hydroxylamine in water (0.5 ml) was added. The mixture was heated at 60° C. overnight, quenched with AcOH and title compound isolated by reversed phase chromatography (Kinetex C18, 5 μm, 21.2× 100 mm, flow 25 ml/min, gradient 0.1% TFA in water/acetonitrile over 15 minutes). Yield: 2.9 mg (10%); brown solid.

Example 205

N-Hydroxy-2-[4-(morpholin-4-ylmethyl)phenyl]-1H-benzimidazole-6-carboxamide trifluoroacetate General Procedure M A solution of terephthalaldehyde monoethylacetale (50 mg, 0.24 mmol), morpholine (31 μL, 0.36 mmol) and NaBH(OAc)$_3$ (102 mg, 0.48 mmol) in CH$_2$Cl$_2$ (2 mL) was stirred at room temperature for 24 h. Sat. NaHCO$_3$-solution was added and the phases were separated. The organic phase was dried over sodium sulfate. The solvents were removed in vacuo.

The crude product was dissolved in DCM (1 ml) and HCl (0.5 ml of a 2 M solution in water) was added and the mixture was stirred vigorously for 1 h at room temperature. The solution was basified with 1 M NaOH and the phases were separated. The organic phase was dried over sodium sulfate. The solvents were removed in vacuo to give the crude product that was used in the next step without further purification. Yield: 45 mg (91%); colorless oil. 4-(morpholin-4-ylmethyl)benzaldehyde. MS (ESI+) m/z 206 [M+H]$^+$. $^1$H NMR (600 MHz, CHLOROFORM-d) δ ppm 9.99 (s, 1H) 7.83 (d, J=8.24 Hz, 2H) 7.52 (d, J=7.93 Hz, 2H) 3.68-3.81 (m, 4H) 3.32 (s, 2H) 2.37-2.62 (m, 4H).

The aldehyde from above (14.7 mg, 0.072 mmol) in DMF (0.5 ml) was added dropwise to a solution of 3,4-diamino-N-hydroxybenzamide, INTERMEDIATE 1 (10 mg, 0.060 mmol) and methanesulfonic acid (2 μl, 0.024 mmol) in DMF (0.5 ml) at 50° C. in an open flask. The mixture was stirred for 2 h at 50° C. (monitored by LCMS). The crude product was diluted with 2 ml water and the title compound was isolated by reversed phase chromatography (Kinetex C18, 5 μm, 21.2×100 mm, flow 25 ml/min, gradient 0.1% TFA in water/acetonitrile over 15 minutes). Yield: 10.0 mg (47%); colorless oil.

Example 209

N-Hydroxy-2-[4-(morpholin-4-ylmethyl)phenyl]-1H-benzimidazole-5-carboxamide

General Procedure N

To a solution of 100 mg of 3-(bromomethyl)benzonitrile (100 mg, 0.51 mmol) in abs. EtOH (2 ml) were added morpholine (44 μl, 0.51 mmol) and potassium carbonate (212 mg, 1.53 mmol) The reaction was heated to 65° C. for 5 h. Water and DCM were added and the phases were separated. The organic phase was collected and the solvents were removed in vacuo. The crude product was used in the next step without further purification. Yield: 105 mg (quant.); yellow oil. MS(ESI+) m/z 203 [M+H]+. HPLC purity: 83%.

The crude nitrile (100 mg, 0.49 mmol) was dissolved in formic acid (3 ml) and Raney-Nickel in water (1.25 ml of a suspension, 100 g/1 L) was added. The mixture was stirred at 90° C. for 5 h in an open vial. The mixture was filtered through a pad of Celite with EtOAc. Water and more EtOAc were added to the filtered solution and the aqueous phase was basified with 2M NaOH and extracted twice with EtOAc, the organic phase was dried over sodium sulfate and the solvents were removed in vacuo. Yield: 97 mg (96%); yellow oil. 3-(morpholin-4-ylmethyl)benzaldehyde. MS(ESI+) m/z 206 [M+H]+. HPLC purity: 93%. $^1$H NMR (600 MHz, CHLOROFORM-d) δ ppm 10.02 (s, 1H) 7.88 (br. s., 1H) 7.80 (d, J=7.32 Hz, 1H) 7.68 (br. s., 1H) 7.51 (t, J=7.48 Hz, 1H) 3.75 (br. s., 4H) 3.56-3.69 (m, 2H) 2.52 (br. s., 4H).

The aldehyde from above (14.7 mg, 0.072 mmol) in DMF (0.5 ml) was added dropwise to a solution of 3,4-diamino-N-hydroxybenzamide, INTERMEDIATE 1 (10 mg, 0.060 mmol) and methanesulfonic acid (2 µl, 0.024 mmol) in DMF (0.5 ml) at 50° C. in an open flask. The mixture was stirred for 2 h at 50° C. (monitored by LCMS). The crude product was diluted with 2 ml water and the title compound was isolated by reversed phase chromatography, Gemini-NX C18, 5 µm, 21×50 mm, flow 25 ml/min, gradient: water (50 mM NH$_4$HCO$_3$ pH 10)/acetonitrile over 12 minutes). Yield: 7.0 mg (42%); white solid.

Example 214

5-Fluoro-N-hydroxy-2-[4-(1-methylethyl)phenyl]-1H-benzimidazole-6-carboxamide

General Procedure O

4-Isopropylbenzaldehyde (0.075 mmol) in DMF (1 ml) was added dropwise to methyl 4,5-diamino-2-fluorobenzoate, INTERMEDIATE 11 (0.075 mmol) in DMF (2 ml) containing MeSO$_3$H (2 µl) at 50 degrees. Solvent was evaporated and freshly made hydroxylamine potassium salt solution in MeOH (ca 1.7 M, 1.5 ml) was added to the crude material. After stirring for 2 h at room temperature, the mixture was quenched with AcOH and title compound isolated by reversed phase chromatography (ACE 5 C8, 5 µm, 30×100 mm, flow 40 ml/min, gradient 0.1% TFA in water/acetonitrile over 15 minutes).

Example 221

N-Hydroxy-2-(4-methoxyphenyl)-1-methyl-1H-benzimidazole-5-carboxamide

General Procedure P

3-Amino-N-hydroxy-4-(methylamino)benzamide, INTERMEDIATE 12 (9 mg, 0.050 mmol) and methanesulfonic acid (0.5 mg, 0.005 mmol) were dissolved in DMF (500 µl). The mixture was stirred at 50° C. in an open to air vial. 4-Methoxybenzaldehyde (0.050 mmol) in 200 µl of DMF was added in portions of 20 µl over 2 h. The reaction mixture was stirred overnight and purified with reversed phase chromatography (Kinetex C18, 5 µm, 21×100 mm, flow 25 ml/min, gradient: water+0.1% TFA/acetonitrile over 15 minutes). The title compound was obtained after concentration of the pure fractions.

Example 232

2-[3,5-Bis(trifluoromethyl)phenyl]-N-hydroxy-1H-benzimidazole-6-carboxamide

Pd(dppf)Cl$_2$ (5 mg) was added to a mixture of methyl 2-bromo-1H-benzimidazole-6-carboxylate, INTERMEDIATE 10 (28 mg, 0.110 mmol), 3,5-bis(trifluoromethyl)phenylboronic acid (42 mg, 0.165 mmol) and potassium carbonate (30 mg, 0.220 mmol) in MeOH (1 ml) and toluene (1 ml). The mixture was heated in a microwave reactor at 140° C. for 45 min before diluted with EtOAc and filtered through a short plug of silica (1 g). Solvent was evaporated and the crude material was used in the next step without further purifications.

To the crude material from above was added freshly prepared hydroxylamine potassium salt in MeOH (ca 1.7 M, 2 ml) and the mixture was stirred at rt for 2 h, quenched with AcOH (500 µl) and purified by reversed phase chromatography (Kinetex C18, 5 µm, 21.2×100 mm, flow 25 ml/min, gradient 0.1% TFA in water/acetonitrile over 15 minutes). Yield: 13.5 mg (32%, two steps); white solid.

Example 233

2-(Cyclohexylmethyl)-N-hydroxy-1H-benzimidazole-6-carboxamide

General Procedure Q

Cyclohexylacetic acid (10.7 mg, 75 µmol) and methyl 3,4-diaminobenzoate (12.5 mg, 75 µmol) was heated in MeCN (0.5 ml) and POCl$_3$ (100 µl) at 120° C. for 30 min in a microwave reactor. Sat. NaHCO$_3$ (2 ml) and EtOAc (2 ml) was added. The aqueous layer was extracted with EtOAc (2 ml). Combined organic layers were filtered and concentrated.

Freshly prepared hydroxylamine potassium salt in MeOH (ca 1.7 M, 2 ml) was added and the mixture stirred at rt for 3 h before quench with AcOH (500 µl). The title compound was isolated by reversed phase chromatography (Kinetex C18, 5 µm, 21.2×100 mm, flow 25 ml/min, gradient 0.1% TFA in water/acetonitrile over 15 minutes). Yield: 8.8 mg (43%); white solid.

Examples of the present invention are listed in Table 1, with analytical data and synthetic details listed in Table 2.

TABLE 1

| EX | Structural formula | Chemical name |
|---|---|---|
| 1 | | 2-(3-chlorophenyl)-N-hydroxy-1H-benzimidazole-6-carboxamide |

TABLE 1-continued

| EX | Structural formula | Chemical name |
|---|---|---|
| 2 | | N-hydroxy-2-(2-methoxyphenyl)-1H-benzimidazole-6-carboxamide |
| 3 | | 2-(4-bromophenyl)-N-hydroxy-1H-benzimidazole-6-carboxamide |
| 4 | | N-hydroxy-2-(4-methylphenyl)-1H-benzimidazole-6-carboxamide |
| 5 | | N-hydroxy-2-[4-(trifluoromethyl)phenyl]-1H-benzimidazole-6-carboxamide |
| 6 | | 2-biphenyl-4-yl-N-hydroxy-1H-benzimidazole-6-carboxamide |
| 7 | | N-hydroxy-2-(1H-indol-5-yl)-1H-benzimidazole-6-carboxamide trifluoroacetate |
| 8 | | N-hydroxy-2-(4-phenoxyphenyl)-1H-benzimidazole-6-carboxamide |
| 9 | | N-hydroxy-2-naphthalen-2-yl-1H-benzimidazole-6-carboxamide |
| 10 | | N-hydroxy-2-(6-methoxynaphthalen-2-yl)-1H-benzimidazole-6-carboxamide |

TABLE 1-continued

| EX | Structural formula | Chemical name |
|---|---|---|
| 11 | | 2-(2,3-dihydro-1,4-benzodioxin-6-yl)-N-hydroxy-1H-benzimidazole-6-carboxamide |
| 12 | | 2-[4-(difluoromethoxy)phenyl]-N-hydroxy-1H-benzimidazole-6-carboxamide |
| 13 | | 2-(4-fluoro-3-methoxyphenyl)-N-hydroxy-1H-benzimidazole-6-carboxamide |
| 14 | | N-hydroxy-2-(4-hydroxy-3-methoxyphenyl)-1H-benzimidazole-6-carboxamide |
| 15 | | N-hydroxy-2-(4-hydroxy-2,6-dimethylphenyl)-1H-benzimidazole-6-carboxamide |
| 16 | | 2-(4-fluorophenyl)-N-hydroxy-1H-benzimidazole-6-carboxamide |
| 17 | | 2-(2-chlorophenyl)-N-hydroxy-1H-benzimidazole-6-carboxamide |
| 18 | | N-hydroxy-2-[2-(trifluoromethyl)phenyl]-1H-benzimidazole-6-carboxamide |
| 19 | | N-hydroxy-2-(4-methoxyphenyl)-1H-benzimidazole-6-carboxamide |

TABLE 1-continued

| EX | Structural formula | Chemical name |
|---|---|---|
| 20 | | 2-[4-(acetylamino)phenyl]-N-hydroxy-1H-benzimidazole-6-carboxamide |
| 21 | | 2-(3-bromophenyl)-N-hydroxy-1H-benzimidazole-6-carboxamide |
| 22 | | N-hydroxy-2-(4-methoxy-3-methylphenyl)-1H-benzimidazole-6-carboxamide |
| 23 | | 2-(4-chlorophenyl)-N-hydroxy-1H-benzimidazole-6-carboxamide |
| 24 | | N-hydroxy-2-(3-methoxy-2-nitrophenyl)-1H-benzimidazole-6-carboxamide |
| 25 | | 2-(3,4-difluorophenyl)-N-hydroxy-1H-benzimidazole-6-carboxamide |
| 26 | | N-hydroxy-2-(4-methoxynaphthalen-1-yl)-1H-benzimidazole-6-carboxamide |
| 27 | | 2-(3-fluoro-2-methylphenyl)-N-hydroxy-1H-benzimidazole-6-carboxamide |
| 28 | | N-hydroxy-2-(3-phenoxyphenyl)-1H-benzimidazole-6-carboxamide |

TABLE 1-continued

| EX | Structural formula | Chemical name |
|---|---|---|
| 29 | | 2-[3-fluoro-5-(trifluoromethyl)phenyl]-N-hydroxy-1H-benzimidazole-6-carboxamide |
| 30 | | N-hydroxy-2-(4-nitrophenyl)-1H-benzimidazole-6-carboxamide |
| 31 | | 2-(5-chloro-2-nitrophenyl)-N-hydroxy-1H-benzimidazole-6-carboxamide |
| 32 | | 2-(4-chloro-3-nitrophenyl)-N-hydroxy-1H-benzimidazole-6-carboxamide |
| 33 | | 2-[4-(diethylamino)phenyl]-N-hydroxy-1H-benzimidazole-6-carboxamide |
| 34 | | 2-[2-chloro-3-(trifluoromethyl)phenyl]-N-hydroxy-1H-benzimidazole-6-carboxamide |
| 35 | | 2-(2,3-difluorophenyl)-N-hydroxy-1H-benzimidazole-6-carboxamide |
| 36 | | 2-[2-fluoro-4-(trifluoromethyl)phenyl]-N-hydroxy-1H-benzimidazole-6-carboxamide |
| 37 | | 2-(2,4-dichlorophenyl)-N-hydroxy-1H-benzimidazole-6-carboxamide |

TABLE 1-continued

| EX | Structural formula | Chemical name |
|---|---|---|
| 38 | | N-hydroxy-2-[3-(trifluoromethyl)phenyl]-1H-benzimidazole-6-carboxamide |
| 39 | | N-hydroxy-2-(3-methoxyphenyl)-1H-benzimidazole-6-carboxamide |
| 40 | | 2-(3,4-dichlorophenyl)-N-hydroxy-1H-benzimidazole-6-carboxamide |
| 41 | | N-hydroxy-2-(3-methylphenyl)-1H-benzimidazole-6-carboxamide |
| 42 | | 2-(2,4-dimethoxyphenyl)-N-hydroxy-1H-benzimidazole-6-carboxamide |
| 43 | | N-hydroxy-2-(3-nitrophenyl)-1H-benzimidazole-6-carboxamide |
| 44 | | 2-(3-cyanophenyl)-N-hydroxy-1H-benzimidazole-6-carboxamide |
| 45 | | 2-(2,5-dimethoxyphenyl)-N-hydroxy-1H-benzimidazole-6-carboxamide |
| 46 | | 2-(3,4-dimethoxyphenyl)-N-hydroxy-1H-benzimidazole-6-carboxamide |

TABLE 1-continued

| EX | Structural formula | Chemical name |
|---|---|---|
| 47 | | N-hydroxy-2-(2-methoxynaphthalen-1-yl)-1H-benzimidazole-6-carboxamide |
| 48 | | N-hydroxy-2-naphthalen-1-yl-1H-benzimidazole-6-carboxamide |
| 49 | | 2-(2-fluoro-5-nitrophenyl)-N-hydroxy-1H-benzimidazole-6-carboxamide |
| 50 | | N-hydroxy-2-[4-(1-methylethyl)phenyl]-1H-benzimidazole-6-carboxamide |
| 51 | | 2-(2-chloro-5-nitrophenyl)-N-hydroxy-1H-benzimidazole-6-carboxamide |
| 52 | | 2-(3,5-dimethoxyphenyl)-N-hydroxy-1H-benzimidazole-6-carboxamide |
| 53 | | 2-furan-3-yl-N-hydroxy-1H-benzimidazole-6-carboxamide |
| 54 | | 2-furan-2-yl-N-hydroxy-1H-benzimidazole-6-carboxamide |

TABLE 1-continued

| EX | Structural formula | Chemical name |
|---|---|---|
| 55 | | N-hydroxy-2-(1-methyl-1H-pyrrol-2-yl)-1H-benzimidazole-6-carboxamide |
| 56 | | N-hydroxy-2-pyridin-3-yl-1H-benzimidazole-6-carboxamide |
| 57 | | N-hydroxy-2-(1H-pyrrol-2-yl)-1H-benzimidazole-6-carboxamide |
| 58 | | N-hydroxy-2-thiophen-3-yl-1H-benzimidazole-6-carboxamide |
| 59 | | N-hydroxy-2-(5-methylfuran-2-yl)-1H-benzimidazole-6-carboxamide |
| 60 | | N-hydroxy-2-(2-phenyl-1H-imidazol-4-yl)-1H-benzimidazole-6-carboxamide |
| 61 | | N-hydroxy-2-(3-methylthiophen-2-yl)-1H-benzimidazole-6-carboxamide |
| 62 | | 2-(1,3-benzodioxol-5-yl)-N-hydroxy-1H-benzimidazole-6-carboxamide |
| 63 | | 2-(1-benzofuran-2-yl)-N-hydroxy-1H-benzimidazole-6-carboxamide |

TABLE 1-continued

| EX | Structural formula | Chemical name |
|---|---|---|
| 64 | | N-hydroxy-2-(1-methyl-1H-indol-3-yl)-1H-benzimidazole-6-carboxamide |
| 65 | | N-hydroxy-2-(6-methylpyridin-2-yl)-1H-benzimidazole-6-carboxamide |
| 66 | | N-hydroxy-2-quinolin-4-yl-1H-benzimidazole-6-carboxamide trifluoroacetate |
| 67 | | 2-(4-bromothiophen-2-yl)-N-hydroxy-1H-benzimidazole-6-carboxamide |
| 68 | | N-hydroxy-2-(2-methyl-1H-indol-3-yl)-1H-benzimidazole-6-carboxamide |
| 69 | | N-hydroxy-2-(1H-indol-3-yl)-1H-benzimidazole-6-carboxamide |
| 70 | | 2-(5-chlorothiophen-2-yl)-N-hydroxy-1H-benzimidazole-6-carboxamide |
| 71 | | N-hydroxy-2-(5-nitrothiophen-2-yl)-1H-benzimidazole-6-carboxamide |

TABLE 1-continued

| EX | Structural formula | Chemical name |
|---|---|---|
| 72 | | 2-(5-bromofuran-2-yl)-N-hydroxy-1H-benzimidazole-6-carboxamide |
| 73 | | N-hydroxy-2-[(E)-2-phenylethenyl]-1H-benzimidazole-6-carboxamide |
| 74 | | 2-(5-bromothiophen-2-yl)-N-hydroxy-1H-benzimidazole-6-carboxamide |
| 75 | | 2-(2,2-dimethylpropyl)-N-hydroxy-1H-benzimidazole-6-carboxamide |
| 76 | | N-hydroxy-2-(2-phenylethyl)-1H-benzimidazole-6-carboxamide |
| 77 | | N-hydroxy-2-(1,3,5-trimethyl-1H-pyrazol-4-yl)-1H-benzimidazole-6-carboxamide |
| 78 | | 2-butyl-N-hydroxy-1H-benzimidazole-6-carboxamide |
| 79 | | 2-(1-ethylpropyl)-N-hydroxy-1H-benzimidazole-6-carboxamide |
| 80 | | 2-(4-ethynylphenyl)-N-hydroxy-1H-benzimidazole-6-carboxamide |

TABLE 1-continued

| EX | Structural formula | Chemical name |
|---|---|---|
| 81 | | 2-(5-tert-butyl-2-hydroxyphenyl)-N-hydroxy-1H-benzimidazole-6-carboxamide |
| 82 | | 2-[3-(4-tert-butylphenoxy)phenyl]-N-hydroxy-1H-benzimidazole-6-carboxamide |
| 83 | | N-hydroxy-2-(2-methylbiphenyl-3-yl)-1H-benzimidazole-6-carboxamide |
| 84 | | N-hydroxy-2-(4-hydroxyphenyl)-1H-benzimidazole-6-carboxamide |
| 85 | | N-hydroxy-2-(2-hydroxy-3-methoxyphenyl)-1H-benzimidazole-6-carboxamide |
| 86 | | N-hydroxy-2-(2-hydroxynaphthalen-1-yl)-1H-benzimidazole-6-carboxamide |
| 87 | | 2-(4-ethoxyphenyl)-N-hydroxy-1H-benzimidazole-6-carboxamide |
| 88 | | N-hydroxy-2-(1,3-thiazol-2-yl)-1H-benzimidazole-6-carboxamide |

TABLE 1-continued

| EX | Structural formula | Chemical name |
|---|---|---|
| 89 | | N-hydroxy-2-(4-hydroxy-2-methoxyphenyl)-1H-benzimidazole-6-carboxamide |
| 90 | | N-hydroxy-2-(4-hydroxy-2-methylphenyl)-1H-benzimidazole-6-carboxamide |
| 91 | | 2-(3-fluoro-2-hydroxyphenyl)-N-hydroxy-1H-benzimidazole-6-carboxamide |
| 92 | | N-hydroxy-2-(3-hydroxyphenyl)-1H-benzimidazole-6-carboxamide |
| 93 | | N-hydroxy-2-(4-hydroxy-3-methoxyphenyl)-1H-benzimidazole-6-carboxamide |
| 94 | | N-hydroxy-2-(2-hydroxyphenyl)-1H-benzimidazole-6-carboxamide |
| 95 | | N-hydroxy-2-(2-methylphenyl)-1H-benzimidazole-6-carboxamide |
| 96 | | 2-(2,3-dihydro-1-benzofuran-5-yl)-N-hydroxy-1H-benzimidazole-6-carboxamide |
| 97 | | N-hydroxy-2-[4-(1-methylethoxy)phenyl]-1H-benzimidazole-6-carboxamide |
| 98 | | N-hydroxy-2-thiophen-2-yl-1H-benzimidazole-6-carboxamide |

TABLE 1-continued

| EX | Structural formula | Chemical name |
|---|---|---|
| 99 | | 2-(5-chloro-2-hydroxyphenyl)-N-hydroxy-1H-benzimidazole-6-carboxamide |
| 100 | | N-hydroxy-2-(4-hydroxy-2,6-dimethylphenyl)-1H-benzimidazole-6-carboxamide |
| 101 | | 2-(4-fluoro-3-methylphenyl)-N-hydroxy-1H-benzimidazole-6-carboxamide |
| 102 | | 2-(4,5-dimethylthiophen-2-yl)-N-hydroxy-1H-benzimidazole-6-carboxamide |
| 103 | | 2-(2,5-dimethylphenyl)-N-hydroxy-1H-benzimidazole-6-carboxamide |
| 104 | | 2-(2,4-dimethylphenyl)-N-hydroxy-1H-benzimidazole-6-carboxamide |
| 105 | | 2-(3,4-dimethylphenyl)-N-hydroxy-1H-benzimidazole-6-carboxamide |
| 106 | | 2-(3-fluoro-4-methylphenyl)-N-hydroxy-1H-benzimidazole-6-carboxamide |
| 107 | | 2-(2,3-dimethylphenyl)-N-hydroxy-1H-benzimidazole-6-carboxamide |

TABLE 1-continued

| EX | Structural formula | Chemical name |
|---|---|---|
| 108 | | N-hydroxy-2-(3-methyl-1-phenyl-1H-pyrazol-4-yl)-1H-benzimidazole-6-carboxamide |
| 109 | | 2-(4-ethylphenyl)-N-hydroxy-1H-benzimidazole-6-carboxamide |
| 110 | | 2-(2-ethylphenyl)-N-hydroxy-1H-benzimidazole-6-carboxamide |
| 111 | | N-hydroxy-2-(4-pentylphenyl)-1H-benzimidazole-6-carboxamide |
| 112 | | N-hydroxy-2-(1-methyl-1H-indol-2-yl)-1H-benzimidazole-6-carboxamide |
| 113 | | N-hydroxy-2-[3-(4-methoxyphenoxy)phenyl]-1H-benzimidazole-6-carboxamide |
| 114 | | N-hydroxy-2-(3'-methoxybiphenyl-4-yl)-1H-benzimidazole-6-carboxamide |
| 115 | | 2-(3,5-di-tert-butyl-4-hydroxyphenyl)-N-hydroxy-1H-benzimidazole-6-carboxamide |
| 116 | | 2-(4-bromo-3-fluorophenyl)-N-hydroxy-1H-benzimidazole-6-carboxamide |

TABLE 1-continued

| EX | Structural formula | Chemical name |
| --- | --- | --- |
| 117 | | 2-(4-chloro-3-fluorophenyl)-N-hydroxy-1H-benzimidazole-6-carboxamide |
| 118 | | 2-(3-fluorophenyl)-N-hydroxy-1H-benzimidazole-6-carboxamide |
| 119 | | 2-biphenyl-2-yl-N-hydroxy-1H-benzimidazole-6-carboxamide |
| 120 | | 2-(2-fluorophenyl)-N-hydroxy-1H-benzimidazole-6-carboxamide |
| 121 | | N-hydroxy-2-(4-propoxyphenyl)-1H-benzimidazole-6-carboxamide |
| 122 | | N-hydroxy-2-[4-(2-methylpropoxy)phenyl]-1H-benzimidazole-6-carboxamide |
| 123 | | N-hydroxy-2-{4-[2-(2-methoxyethoxy)ethoxy]phenyl}-1H-benzimidazole-6-carboxamide |

TABLE 1-continued

| EX | Structural formula | Chemical name |
|---|---|---|
| 124 | | N-hydroxy-2-[4-(2-morpholin-4-ylethoxy)phenyl]-1H-benzimidazole-6-carboxamide |
| 125 | | 2-{4-[2-(diethylamino)ethoxy]phenyl}-N-hydroxy-1H-benzimidazole-6-carboxamide |
| 126 | | 2-[4-(2-ethoxyethoxy)phenyl]-N-hydroxy-1H-benzimidazole-6-carboxamide |
| 127 | | N-hydroxy-2-[4-(2-phenoxyethoxy)phenyl]-1H-benzimidazole-6-carboxamide |
| 128 | | N-hydroxy-2-(3-propoxyphenyl)-1H-benzimidazole-6-carboxamide |
| 129 | | N-hydroxy-2-[3-(2-methylpropoxy)phenyl]-1H-benzimidazole-6-carboxamide |

TABLE 1-continued

| EX | Structural formula | Chemical name |
|---|---|---|
| 130 | | N-hydroxy-2-{3-[2-(2-methoxyethoxy)ethoxy]phenyl}-1H-benzimidazole-6-carboxamide |
| 131 | | N-hydroxy-2-[3-(2-morpholin-4-ylethoxy)phenyl]-1H-benzimidazole-6-carboxamide trifluoroacetate |
| 132 | | 2-{3-[2-(diethylamino)ethoxy]phenyl}-N-hydroxy-1H-benzimidazole-6-carboxamide trifluoroacetate |
| 133 | | 2-[3-(2-ethoxyethoxy)phenyl]-N-hydroxy-1H-benzimidazole-6-carboxamide |
| 134 | | N-hydroxy-2-[3-(2-phenoxyethoxy)phenyl]-1H-benzimidazole-6-carboxamide |
| 135 | | N-hydroxy-2-[3-(2-morpholin-4-yl-2-oxoethoxy)phenyl]-1H-benzimidazole-6-carboxamide |

TABLE 1-continued

| EX | Structural formula | Chemical name |
|---|---|---|
| 136 | | N-hydroxy-2-[3-(2-hydroxyethoxy)phenyl]-1H-benzimidazole-6-carboxamide |
| 137 | | N-hydroxy-2-(2-propoxyphenyl)-1H-benzimidazole-6-carboxamide |
| 138 | | N-hydroxy-2-[2-(2-methylpropoxy)phenyl]-1H-benzimidazole-6-carboxamide |
| 139 | | N-hydroxy-2-{2-[2-(2-methoxyethoxy)ethoxy]phenyl}-1H-benzimidazole-6-carboxamide |
| 140 | | N-hydroxy-2-[2-(2-morpholin-4-ylethoxy)phenyl]-1H-benzimidazole-6-carboxamide trifluoroacetate |
| 141 | | 2-{2-[2-(diethylamino)ethoxy]phenyl}-N-hydroxy-1H-benzimidazole-6-carboxamide trifluoroacetate |

TABLE 1-continued

| EX | Structural formula | Chemical name |
|---|---|---|
| 142 | | 2-[2-(2-ethoxyethoxy)phenyl]-N-hydroxy-1H-benzimidazole-6-carboxamide |
| 143 | | N-hydroxy-2-[2-(2-phenoxyethoxy)phenyl]-1H-benzimidazole-6-carboxamide |
| 144 | | N-hydroxy-2-[2-(2-morpholin-4-yl-2-oxoethoxy)phenyl]-1H-benzimidazole-6-carboxamide |
| 145 | | 2-(4-chlorobenzyl)-N-hydroxy-1H-benzimidazole-6-carboxamide |
| 146 | | 2-(4-fluorobenzyl)-N-hydroxy-1H-benzimidazole-6-carboxamide |
| 147 | | 2-cyclohexyl-N-hydroxy-1H-benzimidazole-6-carboxamide |

TABLE 1-continued

| EX | Structural formula | Chemical name |
|---|---|---|
| 148 | | N-hydroxy-2-(4'-methoxybiphenyl-3-yl)-1H-benzimidazole-6-carboxamide |
| 149 | | 2-(3'-chlorobiphenyl-3-yl)-N-hydroxy-1H-benzimidazole-6-carboxamide |
| 150 | | N-hydroxy-2-(4'-methoxybiphenyl-4-yl)-1H-benzimidazole-6-carboxamide |
| 151 | | 2-(3'-chlorobiphenyl-4-yl)-N-hydroxy-1H-benzimidazole-6-carboxamide |
| 152 | | N-hydroxy-2-[4-(methylsulfonyl)phenyl]-1H-benzimidazole-6-carboxamide |
| 153 | | N-hydroxy-2-(5-phenylfuran-2-yl)-1H-benzimidazole-6-carboxamide |
| 154 | | 2-[5-(3-chlorophenyl)furan-2-yl]-N-hydroxy-1H-benzimidazole-6-carboxamide |

TABLE 1-continued

| EX | Structural formula | Chemical name |
|---|---|---|
| 155 | | N-hydroxy-2-[5-(4-methoxyphenyl)furan-2-yl]-1H-benzimidazole-6-carboxamide |
| 156 | | 2-[5-(2-fluorophenyl)furan-2-yl]-N-hydroxy-1H-benzimidazole-6-carboxamide |
| 157 | | N-hydroxy-2-(5-pyridin-3-ylfuran-2-yl)-1H-benzimidazole-6-carboxamide trifluoroacetate |
| 158 | | N-hydroxy-2-{5-[4-(methylsulfonyl)phenyl]furan-2-yl}-1H-benzimidazole-6-carboxamide |
| 159 | | 2-(4-tert-butylphenyl)-N-hydroxy-1H-benzimidazole-6-carboxamide |
| 160 | | N-hydroxy-2-(4-methoxy-3,5-dimethylphenyl)-1H-benzimidazole-6-carboxamide |
| 161 | | 2-(4-nonylphenyl)-N-hydroxy-1H-benzimidazole-6-carboxamide |

TABLE 1-continued

| EX | Structural formula | Chemical name |
|---|---|---|
| 162 | | 2-(4-butylphenyl)-N-hydroxy-1H-benzimidazole-6-carboxamide |
| 163 | | 2-(2'-fluorobiphenyl-3-yl)-N-hydroxy-1H-benzimidazole-6-carboxamide |
| 164 | | N-hydroxy-2-[4'-(methylsulfonyl)biphenyl-3-yl]-1H-benzimidazole-6-carboxamide |
| 165 | | N-hydroxy-2-(3-pyridin-3-ylphenyl)-1H-benzimidazole-6-carboxamide |
| 166 | | 2-biphenyl-3-yl-N-hydroxy-1H-benzimidazole-6-carboxamide |
| 167 | | 2-(2'-fluorobiphenyl-4-yl)-N-hydroxy-1H-benzimidazole-6-carboxamide |
| 168 | | N-hydroxy-2-[4'-(methylsulfonyl)biphenyl-4-yl]-1H-benzimidazole-6-carboxamide |

TABLE 1-continued

| EX | Structural formula | Chemical name |
|---|---|---|
| 169 | | 2-(2',5'-difluorobiphenyl-3-yl)-N-hydroxy-1H-benzimidazole-6-carboxamide |
| 170 | | 2-(3',4'-dimethoxybiphenyl-3-yl)-N-hydroxy-1H-benzimidazole-6-carboxamide |
| 171 | | N-hydroxy-2-[4'-(trifluoromethyl)biphenyl-3-yl]-1H-benzimidazole-6-carboxamide |
| 172 | | N-hydroxy-2-[4'-(trifluoromethyl)biphenyl-4-yl]-1H-benzimidazole-6-carboxamide |
| 173 | | 2-[5-(2,5-difluorophenyl)furan-2-yl]-N-hydroxy-1H-benzimidazole-6-carboxamide |
| 174 | | 2-[5-(3,4-dimethoxyphenyl)furan-2-yl]-N-hydroxy-1H-benzimidazole-6-carboxamide |

TABLE 1-continued

| EX | Structural formula | Chemical name |
|---|---|---|
| 175 | | N-hydroxy-2-{5-[4-(trifluoromethyl)phenyl]furan-2-yl}-1H-benzimidazole-6-carboxamide |
| 176 | | 2-[5-(2-fluorophenyl)thiophen-2-yl]-N-hydroxy-1H-benzimidazole-6-carboxamide |
| 177 | | 2-[5-(3-chlorophenyl)thiophen-2-yl]-N-hydroxy-1H-benzimidazole-6-carboxamide |
| 178 | | N-hydroxy-2-[5-(4-methoxyphenyl)thiophen-2-yl]-1H-benzimidazole-6-carboxamide |
| 179 | | N-hydroxy-2-(5-phenylthiophen-2-yl)-1H-benzimidazole-6-carboxamide |
| 180 | | 2-(2-fluorobiphenyl-4-yl)-N-hydroxy-1H-benzimidazole-6-carboxamide |
| 181 | | 2-(2,2'-difluorobiphenyl-4-yl)-N-hydroxy-1H-benzimidazole-6-carboxamide |

TABLE 1-continued

| EX | Structural formula | Chemical name |
|---|---|---|
| 182 | | 2-(2,5'-difluoro-2'-hydroxybiphenyl-4-yl)-N-hydroxy-1H-benzimidazole-6-carboxamide |
| 183 | | 2-(2,4'-difluorobiphenyl-4-yl)-N-hydroxy-1H-benzimidazole-6-carboxamide |
| 184 | | 2-(3'-{[(cis)-2,6-dimethylmorpholin-4-yl]methyl}biphenyl-4-yl)-N-hydroxy-1H-benzimidazole-6-carboxamide trifluoroacetate |
| 185 | | N-hydroxy-2-[3'-(morpholin-4-ylmethyl)biphenyl-4-yl]-1H-benzimidazole-6-carboxamide trifluoroacetate |
| 186 | | N-hydroxy-2-[3'-(piperidin-1-ylmethyl)biphenyl-4-yl]-1H-benzimidazole-6-carboxamide trifluoroacetate |
| 187 | | 2-{3'-[(diethylamino)methyl]biphenyl-4-yl}-N-hydroxy-1H-benzimidazole-6-carboxamide trifluoroacetate |
| 188 | | 2-(3'-{[bis(2-methylpropyl)amino]methyl}biphenyl-4-yl)-N-hydroxy-1H-benzimidazole-6-carboxamide trifluoroacetate |
| 189 | | N-hydroxy-2-(trifluoromethyl)-1H-benzimidazole-6-carboxamide |

TABLE 1-continued

| EX | Structural formula | Chemical name |
|---|---|---|
| 190 | | N-hydroxy-2-[4'-(morpholin-4-ylmethyl)biphenyl-4-yl]-1H-benzimidazole-6-carboxamide trifluoroacetate |
| 191 | | N-hydroxy-2-(4'-{[(3-methoxypropyl)amino]methyl}biphenyl-4-yl)-1H-benzimidazole-6-carboxamide trifluoroacetate |
| 192 | | 2-(4'-formylbiphenyl-4-yl)-N-hydroxy-1H-benzimidazole-6-carboxamide |
| 193 | | N-hydroxy-2-{4'-[(E)-(hydroxyimino)methyl]biphenyl-4-yl}-1H-benzimidazole-6-carboxamide |
| 194 | | 2-[4'-(aminomethyl)biphenyl-4-yl]-N-hydroxy-1H-benzimidazole-6-carboxamide trifluoroacetate |
| 195 | | 2-[3'-(dimethylcarbamoyl)biphenyl-4-yl]-N-hydroxy-1H-benzimidazole-6-carboxamide |
| 196 | | N-hydroxy-2-[4'-(hydroxymethyl)biphenyl-4-yl]-1H-benzimidazole-6-carboxamide |
| 197 | | N-hydroxy-2-[4'-(pyrrolidin-1-ylmethyl)biphenyl-4-yl]-1H-benzimidazole-6-carboxamide trifluoroacetate |

TABLE 1-continued

| EX | Structural formula | Chemical name |
|---|---|---|
| 198 | | 2-{4'-[(dimethylamino)methyl]biphenyl-4-yl}-N-hydroxy-1H-benzimidazole-6-carboxamide trifluoroacetate |
| 199 | | 2-(4'-{[bis(2-methylpropyl)amino]methyl}biphenyl-4-yl)-N-hydroxy-1H-benzimidazole-6-carboxamide trifluoroacetate |
| 200 | | N-hydroxy-2-[4'-(piperidin-1-ylmethyl)biphenyl-4-yl]-1H-benzimidazole-6-carboxamide trifluoroacetate |
| 201 | | 2-(4'-{cis)-2,6-dimethylmorpholin-4-yl]methyl}biphenyl-4-yl)-N-hydroxy-1H-benzimidazole-6-carboxamide trifluoroacetate |
| 202 | | N-hydroxy-2-[3'-(hydroxymethyl)biphenyl-4-yl]-1H-benzimidazole-6-carboxamide |
| 203 | | 2-(3'-carbamoylbiphenyl-4-yl)-N-hydroxy-1H-benzimidazole-6-carboxamide |
| 204 | | N-hydroxy-2-{4'-[(methylsulfonyl)amino]biphenyl-4-yl}-1H-benzimidazole-6-carboxamide |
| 205 | | N-hydroxy-2-[4-(morpholin-4-ylmethyl)phenyl]-1H-benzimidazole-6-carboxamide trifluoroacetate |

TABLE 1-continued

| EX | Structural formula | Chemical name |
|---|---|---|
| 206 | | N-hydroxy-2-[4-(piperidin-1-ylmethyl)phenyl]-1H-benzimidazole-6-carboxamide |
| 207 | | N-hydroxy-2-{4-[(4-methylpiperazin-1-yl)methyl]phenyl}-1H-benzimidazole-6-carboxamide |
| 208 | | N-hydroxy-2-(4-{[(2-methoxyethyl)amino]methyl}phenyl)-1H-benzimidazole-6-carboxamide |
| 209 | | N-hydroxy-2-[3-(morpholin-4-ylmethyl)phenyl]-1H-benzimidazole-6-carboxamide |
| 210 | | N-hydroxy-2-[3-(piperidin-1-ylmethyl)phenyl]-1H-benzimidazole-6-carboxamide |
| 211 | | N-hydroxy-2-{3-[(4-methylpiperazin-1-yl)methyl]phenyl}-1H-benzimidazole-6-carboxamide |
| 212 | | N-hydroxy-2-(3-{[(2-methoxyethyl)amino]methyl}phenyl)-1H-benzimidazole-6-carboxamide |

TABLE 1-continued

| EX | Structural formula | Chemical name |
|---|---|---|
| 213 | 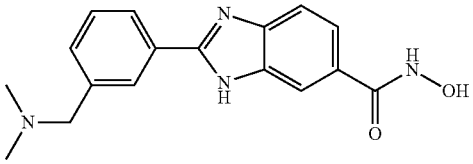 [SMILES: CN(C)Cc1cccc(-c2nc3ccc(C(=O)NO)cc3[nH]2)c1] | 2-{3-[(dimethylamino)methyl]phenyl}-N-hydroxy-1H-benzimidazole-6-carboxamide |
| 214 | 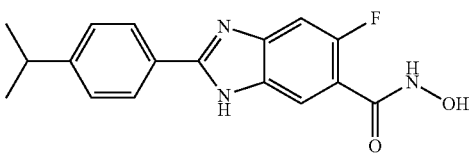 [SMILES: CC(C)c1ccc(-c2nc3cc(F)c(C(=O)NO)cc3[nH]2)cc1] | 5-Fluoro-N-hydroxy-2-[4-(1-methylethyl)phenyl]-1H-benzimidazole-6-carboxamide |
| 215 | 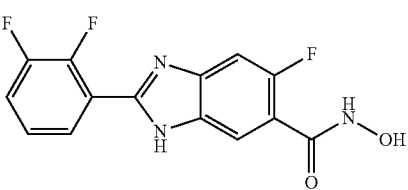 [SMILES: O=C(NO)c1cc2[nH]c(-c3cccc(F)c3F)nc2cc1F] | 2-(2,3-Difluorophenyl)-5-fluoro-N-hydroxy-1H-benzimidazole-6-carboxamide |
| 216 | 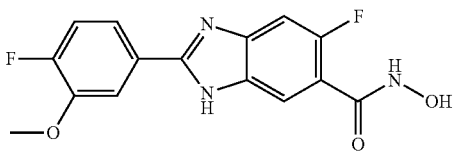 [SMILES: COc1cc(-c2nc3cc(F)c(C(=O)NO)cc3[nH]2)ccc1F] | 5-Fluoro-2-(4-fluoro-3-methoxyphenyl)-N-hydroxy-1H-benzimidazole-6-carboxamide |
| 217 | 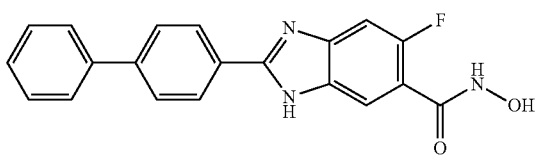 [SMILES: O=C(NO)c1cc2[nH]c(-c3ccc(-c4ccccc4)cc3)nc2cc1F] | 2-Biphenyl-4-yl-5-fluoro-N-hydroxy-1H-benzimidazole-6-carboxamide |
| 218 | 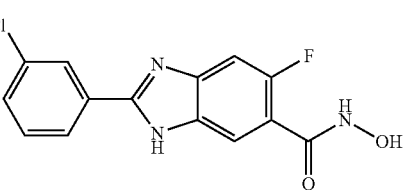 | 2-(3-Chlorophenyl)-5-fluoro-N-hydroxy-1H-benzimidazole-6-carboxamide |
| 219 | 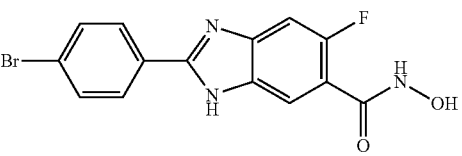 [SMILES: O=C(NO)c1cc2[nH]c(-c3ccc(Br)cc3)nc2cc1F] | 2-(4-bromophenyl)-5-fluoro-N-hydroxy-1H-benzimidazole-6-carboxamide |
| 220 | 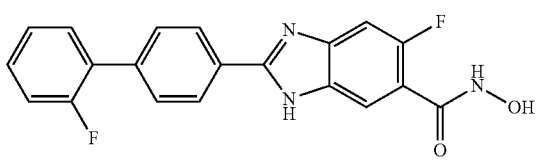 [SMILES: O=C(NO)c1cc2[nH]c(-c3ccc(-c4ccccc4F)cc3)nc2cc1F] | 5-Fluoro-2-(2'-fluorobiphenyl-4-yl)-N-hydroxy-1H-benzimidazole-6-carboxamide |
| 221 | 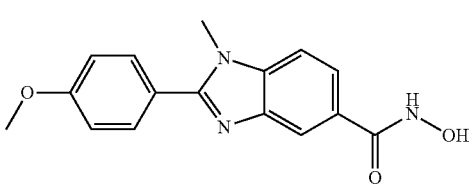 [SMILES: COc1ccc(-c2nc3cc(C(=O)NO)ccc3n2C)cc1] | N-hydroxy-2-(4-methoxyphenyl)-1-methyl-1H-benzimidazole-5-carboxamide |

TABLE 1-continued

| EX | Structural formula | Chemical name |
|---|---|---|
| 222 | | 2-(2,3-difluorophenyl)-N-hydroxy-1-methyl-1H-benzimidazole-5-carboxamide |
| 223 | | N-hydroxy-1-methyl-2-[4-(1-methylethyl)phenyl]-1H-benzimidazole-5-carboxamide |
| 224 | | 2-(4-fluoro-3-methoxyphenyl)-N-hydroxy-1-methyl-1H-benzimidazole-5-carboxamide |
| 225 | | 2-biphenyl-4-yl-N-hydroxy-1-methyl-1H-benzimidazole-5-carboxamide |
| 226 | | 2-(3-chlorophenyl)-N-hydroxy-1-methyl-1H-benzimidazole-5-carboxamide |
| 227 | | N-hydroxy-1-methyl-2-(2-methylphenyl)-1H-benzimidazole-5-carboxamide |
| 228 | | N-hydroxy-2-(4-methoxy-3,5-dimethylphenyl)-1-methyl-1H-benzimidazole-5-carboxamide |
| 229 | | N-hydroxy-2-(2-hydroxynaphthalen-1-yl)-1-methyl-1H-benzimidazole-5-carboxamide |

TABLE 1-continued

| EX | Structural formula | Chemical name |
|---|---|---|
| 230 | | 2-(5-chloro-2-hydroxyphenyl)-N-hydroxy-1-methyl-1H-benzimidazole-5-carboxamide |
| 231 | | N-hydroxy-1-methyl-2-[4-(methylsulfonyl)phenyl]-1H-benzimidazole-5-carboxamide |
| 232 | | 2-[3,5-bis(trifluoromethyl)phenyl]-N-hydroxy-1H-benzimidazole-6-carboxamide |
| 233 | | 2-(cyclohexylmethyl)-N-hydroxy-1H-benzimidazole-6-carboxamide |
| 234 | | 2-(2-fluorobenzyl)-N-hydroxy-1H-benzimidazole-6-carboxamide |
| 235 | | N-hydroxy-2-[3-(trifluoromethyl)benzyl]-1H-benzimidazole-6-carboxamide |

TABLE 1-continued

| EX | Structural formula | Chemical name |
|---|---|---|
| 236 | | 2-[1-(3-fluorobiphenyl-4-yl)ethyl]-N-hydroxy-1H-benzimidazole-6-carboxamide |
| 237 | | N-hydroxy-2-[(1S)-1-(6-methoxynaphthalen-2-yl)ethyl]-1H-benzimidazole-6-carboxamide |
| 238 | | 2-(3-bromophenyl)-N-hydroxy-1H-benzimidazole-6-carboxamide |

TABLE 2

| EX | MS (ESI)+ m/z [M + H]+ | $^1$H NMR (600 MHz, DMSO-$d_6$ d ppm (unless otherwise stated) | General proced. |
|---|---|---|---|
| 1 | 288 | $^1$H NMR (600 MHz, CD$_3$OD) δ ppm 7.62-7.71 (m, 2 H) 7.75-7.80 (m, 1 H) 7.81-7.87 (m, 1 H) 8.06 (ddd, J = 7.54, 1.72, 1.24 Hz, 1 H) 8.14-8.17 (m, 1 H) 8.19 (t, J = 1.75 Hz, 1 H) | A |
| 2 | 284 | $^1$H NMR (600 MHz, CD$_3$OD) δ ppm 4.16 (s, 3 H) 7.30 (ddd, J = 7.85, 7.39, 0.88 Hz, 1 H) 7.42 (dd, J = 8.55, 0.88 Hz, 1 H) 7.77 (ddd, J = 8.55, 7.39, 1.63 Hz, 1 H) 7.88 (dd, J = 8.60, 0.70 Hz, 1 H) 7.94 (dd, J = 8.60, 1.53 Hz, 1 H) 8.11 (dd, J = 7.85, 1.63 Hz, 1 H) 8.24 (dd, J = 1.53, 0.70 Hz, 1 H) | A |
| 3 | 332 | $^1$H NMR (600 MHz, CD$_3$OD) δ ppm 7.78 (dd, J = 8.54, 0.68 Hz, 1 H) 7.84-7.87 (m, 3 H) 8.02-8.06 (m, 2 H) 8.16 (dd, J = 1.51, 0.68 Hz, 1 H) | A |
| 4 | 268 | $^1$H NMR (600 MHz, CD$_3$OD) δ ppm 2.50 (s, 3 H) 7.51-7.55 (m, 2 H) 7.81 (dd, J = 8.55, 0.69 Hz, 1 H) 7.90 (dd, J = 8.55, 1.53 Hz, 1 H) 8.02-8.05 (m, 2 H) 8.17 (dd, J = 1.53, 0.69 Hz, 1 H | A |
| 5 | 322 | $^1$H NMR (600 MHz, CD$_3$OD) δ ppm 7.73-7.77 (m, 1 H) 7.77-7.81 (m, 1 H) 7.91-7.95 (m, 2 H) 8.13-8.15 (m, 1 H) 8.29-8.33 (m, 2 H) | A |
| 6 | 330 | $^1$H NMR (600 MHz, CD$_3$OD) δ ppm 7.42-7.47 (m, 1 H) 7.49-7.54 (m, 2 H) 7.73-7.78 (m, 2 H) 7.83 (dd, J = 8.55, 0.70 Hz, 1 H) 7.91 (dd, J = 8.55, 1.54 Hz, 1 H) 7.96-8.00 (m, 2 H) 8.20 (dd, J = 1.54, 0.70 Hz, 1 H) 8.21-8.24 (m, 2 H | A |
| 7 | 293 | $^1$H NMR (600 MHz, CD$_3$OD) δ ppm 6.71 (dd, J = 3.18, 0.88 Hz, 1 H) 7.48 (d, J = 3.18 Hz, 1 H) 7.69 (ddd, J = 8.58, 0.88, 0.59 Hz, 1 H) 7.80 (dd, J = 8.48, 0.64 Hz, 1 H) 7.88 (dd, J = 8.58, 1.83 Hz, 1 H) 7.89 (dd, J = 8.48, 1.50 Hz, 1 H) 8.16 (dd, J = 1.50, 0.64 Hz, 1 H) 8.44 (dd, J = 1.83, 0.59 Hz, 1 H) | A |
| 8 | 346 | $^1$H NMR (600 MHz, CD$_3$OD) δ ppm 7.13-7.17 (m, 2 H) 7.21-7.25 (m, 2 H) 7.25-7.30 (m, 1 H) 7.45-7.50 (m, 2 H) 7.79 (dd, | A |

TABLE 2-continued

| EX | MS (ESI)+ m/z [M + H]+ | ¹H NMR (600 MHz, DMSO-d₆ δ ppm (unless otherwise stated) | General proced. |
|---|---|---|---|
| | | J = 8.55, 0.63 Hz, 1 H) 7.88 (dd, J = 8.55, 1.50 Hz, 1 H) 8.10-8.14 (m, 2 H) 8.16 (dd, J = 1.50, 0.63 Hz, 1 H) | |
| 9 | 304 | ¹H NMR (600 MHz, CD₃OD) δ ppm 7.67-7.73 (m, 2 H) 7.85 (dd, J = 8.54, 0.63 Hz, 1 H) 7.91 (dd, J = 8.54, 1.50 Hz, 1 H) 8.02-8.05 (m, 1 H) 8.08-8.11 (m, 1 H) 8.16 (dd, J = 8.70, 1.83 Hz, 1 H) 8.17 (d, J = 8.70 Hz, 1 H) 8.21 (dd, J = 1.50, 0.63 Hz, 1 H) 8.71-8.72 (m, 1 H) | A |
| 10 | 334 | ¹H NMR (600 MHz, CD₃OD) δ ppm 3.97 (s, 3 H) 7.31 (dd, J = 9.00, 2.49 Hz, 1 H) 7.38 (d, J = 2.49 Hz, 1 H) 7.82 (dd, J = 8.55, 0.63 Hz, 1 H) 7.91 (dd, J = 8.55, 1.50 Hz, 1 H) 7.97 (d, J = 9.00 Hz, 1 H) 8.05 (d, J = 8.70 Hz, 1 H) 8.08 (dd, J = 8.70, 1.83 Hz, 1 H) 8.19 (dd, J = 1.50, 0.63 Hz, 1 H) 8.60 (d, J = 1.83 Hz, 1 H) | A |
| 11 | 312 | ¹H NMR (600 MHz, CD₃OD) δ ppm 4.35-4.38 (m, 2 H) 4.38-4.41 (m, 2 H) 7.15 (d, J = 8.55 Hz, 1 H) 7.64 (dd, J = 8.55, 2.29 Hz, 1 H) 7.68 (d, J = 2.29 Hz, 1 H) 7.78 (dd, J = 8.55, 0.47 Hz, 1 H) 7.89 (dd, J = 8.55, 1.35 Hz, 1 H) 8.14 (dd, J = 1.35, 0.47 Hz, 1 H) | A |
| 12 | 320 | ¹H NMR (600 MHz, CD₃OD) δ ppm 7.06 (t, J = 73.09 Hz, 1 H) 7.43-7.48 (m, 2 H) 7.80 (d, J = 8.50 Hz, 1 H) 7.87 (d, J = 8.50 Hz, 1 H) 8.16 (br. s., 1 H) 8.17-8.20 (m, 2 H) | A |
| 13 | 302 | ¹H NMR (600 MHz, CD₃OD) δ ppm 4.05 (s, 3 H) 7.41 (dd, J = 10.60, 8.47 Hz, 1 H) 7.72 (ddd, J = 8.47, 3.97, 2.16 Hz, 1 H) 7.79 (d, J = 8.40 Hz, 1 H) 7.87 (d, J = 8.40 Hz, 1 H) 7.91 (dd, J = 7.86, 2.16 Hz, 1 H) 8.16 (br. s., 1 H) | A |
| 14 | 300 | ¹H NMR (600 MHz, CD₃OD) δ ppm 4.03 (s, 3 H) 7.08 (d, J = 8.39 Hz, 1 H) 7.68 (dd, J = 8.39, 1.53 Hz, 1 H) 7.74 (d, J = 1.53 Hz, 1 H) 7.81 (d, J = 8.50 Hz, 1 H) 7.91 (d, J = 8.50 Hz, 1 H) 8.15 (br. s., 1 H) | A |
| 15 | 298 | ¹H NMR (600 MHz, CD₃OD) δ ppm 2.18 (s, 6 H) 6.73 (s, 2 H) 7.88 (d, J = 8.50 Hz, 1 H) 7.98 (d, J = 8.50 Hz, 1 H) 8.23 (br. s., 1 H) | A |
| 16 | 272 | ¹H NMR (600 MHz, CD₃OD) δ ppm 7.43-7.48 (m, 2 H) 7.81 (d, J = 8.40 Hz, 1 H) 7.88 (d, J = 8.40 Hz, 1 H) 8.17 (br. s., 1 H) 8.17-8.22 (m, 2 H) | A |
| 17 | 288 | ¹H NMR (600 MHz, CD₃OD) δ ppm 7.61 (td, J = 7.47, 1.24 Hz, 1 H) 7.69 (ddd, J = 8.12, 7.47, 1.67 Hz, 1 H) 7.74 (dd, J = 8.12, 1.24 Hz, 1 H) 7.84 (dd, J = 8.52, 0.70 Hz, 1 H) 7.88-7.93 (m, 2 H) 8.21 (dd, J = 1.50, 0.70 Hz, 1 | A |
| 18 | 322 | ¹H NMR (600 MHz, CD₃OD) δ ppm 7.81 (dd, J = 8.55, 0.61 Hz, 1 H) 7.85-7.92 (m, 4 H) 7.99-8.04 (m, 1 H) 8.18 (dd, J = 1.58, 0.61 Hz, 1 H) | A |
| 19 | 284 | ¹H NMR (600 MHz, CD₃OD) δ ppm 3.95 (s, 3 H) 7.23-7.28 (m, 2 H) 7.80 (dd, J = 8.54, 0.69 Hz, 1 H) 7.90 (dd, J = 8.54, 1.53 Hz, 1 H) 8.09-8.13 (m, 2 H) 8.16 (dd, J = 1.53, 0.69 Hz, 1 H) | A |
| 20 | 311 | ¹H NMR (600 MHz, CD₃OD) δ ppm 8.14 (s, 1 H) 8.05-8.11 (m, 2 H) 7.87-7.92 (m, 2 H) 7.84 (dd, J = 8.55, 1.53 Hz, 1 H) 7.76 (d, J = 8.55 Hz, 1 H) 2.19 (s, 3 H) | B |
| 21 | 332 | ¹H NMR (600 MHz, CD₃OD) δ ppm 8.34 (t, J = 1.68 Hz, 1 H) 8.08-8.14 (m, 2 H) 7.77 (dd, J = 8.39, 1.37 Hz, 2 H) 7.70-7.74 (m, 1 H) 7.54 (t, 1 H) | B |
| 22 | 298 | ¹H NMR (600 MHz, CD₃OD) δ ppm 8.12 (s, 1 H) 8.00 (dd, J = 8.39, 2.29 Hz, 1 H) 7.92-7.95 (m, 1 H) 7.85 (dd, J = 8.55, 1.22 Hz, 1 H) 7.75 (d, J = 8.54 Hz, 1 H) 7.21 (d, J = 8.54 Hz, 1 H) 3.98 (s, 3 H) 2.34 (s, 3 H) | B |
| 23 | 288 | ¹H NMR (600 MHz, CD₃OD) δ ppm 8.08-8.15 (m, 3 H) 7.76-7.82 (m, 1 H) 7.70-7.74 (m, 1 H) 7.62-7.67 (m, 2 H) | B |
| 24 | 329 | ¹H NMR (600 MHz, CD₃OD) δ ppm 8.03-8.09 (m, 1 H) 7.64-7.76 (m, 3 H) 7.47 (d, J = 8.24 Hz, 2 H) 4.00 (s, 3 H) | B |
| 25 | 290 | ¹H NMR (600 MHz, CD₃OD) δ ppm 8.09-8.11 (m, 1 H) 8.06 (ddd, J = 11.22, 7.40, 2.14 Hz, 1 H) 7.96 (ddd, J = 8.62, 4.04, 1.68 Hz, 1 H) 7.73-7.79 (m, 1 H) 7.68-7.73 (m, 1 H) 7.53 (dt, 1 H) | B |
| 26 | 334 | ¹H NMR (600 MHz, CD₃OD) δ ppm 8.43 (d, J = 7.93 Hz, 1 H) 8.31 (d, J = 8.54 Hz, 1 H) 8.21 (s, 1 H) 7.97 (d, J = 7.93 Hz, 1 H) 7.90 (dd, J = 8.55, 1.53 Hz, 1 H) 7.81-7.86 (m, 1 H) 7.71 (ddd, J = 8.39, 6.87, 1.22 Hz, 1 H) 7.65 (ddd, J = 8.24, 7.02, 1.22 Hz, 1 H) 7.18 (d, J = 7.93 Hz, 1 H) 4.15 (s, 3 H) | B |
| 27 | 286 | ¹H NMR (600 MHz, CD₃OD) δ ppm 8.15 (s, 1 H) 7.82 (dd, J = 8.55, 1.53 Hz, 1 H) 7.73-7.79 (m, 1 H) 7.52 (d, J = 7.32 Hz, 1 H) 7.41-7.48 (m, 1 H) 7.35 (t, J = 8.85 Hz, 1 H) 2.44 (d, J = 2.44 Hz, 3 H) | B |
| 28 | 346 | ¹H NMR (600 MHz, CD₃OD) δ ppm 8.11 (s, 1 H) 7.85-7.90 (m, 1 H) 7.81 (dd, J = 8.54, 1.22 Hz, 1 H) 7.77-7.79 (m, 1 H) 7.73 (d, J = 8.55 Hz, 1 H) 7.63 (t, J = 7.93 Hz, 1 H) 7.41-7.46 (m, 2 H) 7.27 (dd, J = 8.24, 1.83 Hz, 1 H) 7.21 (t, J = 7.32 Hz, 1 H) 7.08-7.13 (m, 2 H) | B |
| 29 | 340 | ¹H NMR (600 MHz, CD₃OD) δ ppm 8.33 (s, 1 H) 8.17 (ddd, J = 9.08, 1.98, 1.75 Hz, 1 H) 8.12 (s, 1 H) 7.66-7.79 (m, 3 H) | B |

TABLE 2-continued

| EX | MS (ESI)+ m/z [M + H]+ | 1H NMR (600 MHz, DMSO-d6 d ppm (unless otherwise stated) | General proced. |
|---|---|---|---|
| 30 | 299 | 1H NMR (600 MHz, CD3OD) δ ppm 8.41-8.48 (m, 2 H) 8.32-8.39 (m, 2 H) 8.13 (s, 1 H) 7.70-7.80 (m, 2 H) | B |
| 31 | 333 | 1H NMR (600 MHz, CD3OD) δ ppm 8.20 (d, J = 8.85 Hz, 1 H) 8.10 (d, J = 0.61 Hz, 1 H) 7.94 (d, J = 2.44 Hz, 1 H) 7.85 (dd, J = 8.85, 2.44 Hz, 1 H) 7.73-7.80 (m, 1 H) 7.69-7.74 (m, 1 H) | B |
| 32 | 333 | 1H NMR (600 MHz, CD3OD) δ ppm 8.70 (d, J = 2.14 Hz, 1 H) 8.36 (dd, J = 8.55, 2.14 Hz, 1 H) 8.10 (br. s., 1 H) 7.89 (d, J = 8.55 Hz, 1 H) 7.73 (br. s., 2 H) | B |
| 33 | 325 | 1H NMR (600 MHz, CD3OD) δ ppm 8.08 (d, 1 H) 7.92-7.98 (m, 2 H) 7.86 (dd, J = 8.55, 1.53 Hz, 1 H) 7.72 (d, J = 8.55 Hz, 1 H) 6.91-6.98 (m, 2 H) 3.55 (q, J = 7.32 Hz, 4 H) 1.25 (t, J = 7.02 Hz, 6 H) | B |
| 34 | 356 | 1H NMR (600 MHz, CD3OD) δ ppm 8.16 (s, 1 H) 8.02-8.09 (m, 2 H) 7.78-7.83 (m, 1 H) 7.71-7.78 (m, 2 H) | B |
| 35 | 291 | 1H NMR (600 MHz, CD3OD) δ ppm 8.14 (s, 1 H) 7.92-7.99 (m, 1 H) 7.71-7.81 (m, 2 H) 7.48-7.60 (m, 1 H) 7.36-7.45 (m, 1 H) | B |
| 36 | 340 | 1H NMR (600 MHz, CD3OD) δ ppm 8.41 (t, J = 7.63 Hz, 1 H) 8.15 (s, 1 H) 7.73-7.85 (m, 4 H) | B |
| 37 | 322 | 1H NMR (600 MHz, CD3OD) δ ppm 8.14 (s, 1 H) 7.87 (d, J = 8.55 Hz, 1 H) 7.71-7.81 (m, 3 H) 7.59 (dd, 1 H) | B |
| 38 | 322 | 1H NMR (600 MHz, CD3OD) δ ppm 8.48 (s, 1 H) 8.39 (d, J = 7.63 Hz, 1 H) 8.11 (s, 1 H) 7.87 (d, J = 8.55 Hz, 1 H) 7.80 (t, J = 7.93 Hz, 1 H) 7.68-7.76 (m, 2 H) | B |
| 39 | 284 | 1H NMR (600 MHz, CD3OD) δ ppm 8.14 (s, 1 H) 7.83 (dd, J = 8.70, 1.37 Hz, 1 H) 7.77 (d, J = 8.55 Hz, 1 H) 7.67-7.73 (m, 2 H) 7.56 (t, J = 7.93 Hz, 1 H) 7.24 (dd, J = 7.78, 2.90 Hz, 1 H) 3.94 (s, 3 H) | B |
| 40 | 322 | 1H NMR (600 MHz, CD3OD) δ ppm 8.32 (d, J = 2.14 Hz, 1 H) 8.10 (s, 1 H) 8.05 (dd, J = 8.54, 2.14 Hz, 1 H) 7.78 (d, J = 8.54 Hz, 1 H) 7.74-7.77 (m, 1 H) 7.69-7.74 (m, 1 H) | B |
| 41 | 268 | 1H NMR (600 MHz, CD3OD) δ ppm 8.15 (s, 1 H) 7.97 (s, 1 H) 7.93 (d, J = 7.63 Hz, 1 H) 7.85 (dd, J = 8.55, 1.53 Hz, 1 H) 7.75-7.80 (m, 1 H) 7.54 (dt, J = 15.49, 7.67 Hz, 2 H) 2.51 (s, 3 H) | B |
| 42 | 314 | 1H NMR (600 MHz, CD3OD) δ ppm 8.17 (s, 1 H) 8.08 (d, J = 8.55 Hz, 1 H) 7.86 (dd, J = 8.54, 1.22 Hz, 1 H) 7.76-7.82 (m, 1 H) 6.83-6.91 (m, 2 H) 4.15 (s, 3 H) 3.97 (s, 3 H) | B |
| 43 | 299 | 1H NMR (600 MHz, CD3OD) δ ppm 9.04 (t, J = 1.83 Hz, 1 H) 8.53 (d, J = 7.93 Hz, 1 H) 8.41 (dd, J = 7.78, 1.98 Hz, 1 H) 8.12 (br. s., 1 H) 7.85 (t, J = 7.93 Hz, 1 H) 7.74 (br. s., 2 H) | B |
| 44 | 279 | 1H NMR (600 MHz, CD3OD) δ ppm 8.47 (t, J = 1.53 Hz, 1 H) 8.39-8.44 (m, 1 H) 8.11 (s, 1 H) 7.90-7.96 (m, 1 H) 7.79 (t, J = 7.93 Hz, 1 H) 7.73-7.76 (m, 1 H) 7.69-7.73 (m, 1 H) | B |
| 45 | 314 | 1H NMR (600 MHz, CD3OD) δ ppm 8.19 (s, 1 H) 7.80-7.87 (m, 2 H) 7.76 (d, J = 2.75 Hz, 1 H) 7.23-7.32 (m, 2 H) 4.09 (s, 3 H) 3.90 (s, 3 H) | B |
| 46 | 314 | 1H NMR (600 MHz, CD3OD) δ ppm 8.14 (s, 1 H) 7.87 (dd, J = 8.55, 1.22 Hz, 1 H) 7.76-7.79 (m, 2 H) 7.74 (d, J = 2.14 Hz, 1 H) 7.25 (d, J = 8.54 Hz, 1 H) 4.00 (s, 3 H) 3.97 (s, 3 H) | B |
| 47 | 334 | 1H NMR (600 MHz, CD3OD) δ ppm 8.28 (d, 1 H) 8.25 (s, 1 H) 8.01 (d, J = 8.24 Hz, 1 H) 7.97 (dd, J = 8.55, 1.53 Hz, 1 H) 7.89 (d, J = 8.55 Hz, 1 H) 7.71 (d, J = 8.55 Hz, 1 H) 7.66 (d, J = 9.16 Hz, 1 H) 7.56-7.61 (m, 1 H) 7.46-7.53 (m, 1 H) 4.04 (s, 3 H) | B |
| 48 | 304 | 1H NMR (600 MHz, CD3OD) δ ppm 8.33 (d, J = 7.93 Hz, 1 H) 8.17-8.25 (m, 2 H) 8.04-8.12 (m, 1 H) 7.99 (dd, J = 7.02, 1.22 Hz, 1 H) 7.87-7.93 (m, 1 H) 7.82-7.87 (m, 1 H) 7.64-7.75 (m, 3 H) | B |
| 49 | 317 | 1H NMR (600 MHz, CD3OD) δ ppm 9.14 (dd, 1 H) 8.44-8.53 (m, 1 H) 8.16 (s, 1 H) 7.76 (d, J = 1.22 Hz, 2 H) 7.65 (dd, J = 10.38, 9.16 Hz, 1 H) | B |
| 50 | 296 | 1H NMR (600 MHz, CD3OD) δ ppm 8.14 (s, 1 H) 8.02-8.10 (m, 2 H) 7.85 (dd, J = 8.55, 1.22 Hz, 1 H) 7.77 (d, J = 8.24 Hz, 1 H) 7.56 (d, J = 8.24 Hz, 2 H) 3.06 (quin, J = 6.94 Hz, 1 H) 1.33 (d, J = 7.02 Hz, 6 H) | B |
| 51 | 333 | 1H NMR (600 MHz, CD3OD) δ ppm 8.77 (d, J = 2.75 Hz, 1 H) 8.41 (dd, J = 8.85, 2.75 Hz, 1 H) 8.16 (s, 1 H) 7.92 (d, J = 8.85 Hz, 1 H) 7.71-7.82 (m, 2 H) | B |
| 52 | 314 | 1H NMR (600 MHz, CD3OD) δ ppm 8.14 (s, 1 H) 7.84 (dd, J = 8.55, 1.53 Hz, 1 H) 7.74-7.78 (m, 1 H) 7.32 (d, J = 2.14 Hz, 2 H) 6.78 (t, J = 2.29 Hz, 1 H) 3.92 (s, 6 H) | B |
| 53 | 244 | 1H NMR (600 MHz, CD3OD) δ ppm 8.29 (s, 1 H) 8.02 (br. s., 1 H) 7.72 (t, J = 1.83 Hz, 1 H) 7.68 (dd, J = 8.39, 1.68 Hz, 1 H) 7.62 (d, J = 8.24 Hz, 1 H) 7.07 (dd, J = 1.83, 0.61 Hz, 1 H) | B |
| 54 | 244 | 1H NMR (600 MHz, CD3OD) δ ppm 8.03 (s, 1 H) 7.80 (d, J = 1.83 Hz, 1 H) 7.66-7.72 (m, 1 H) 7.61-7.65 (m, 1 H) 7.27 (d, J = 3.66 Hz, 1 H) 6.71 (dd, 1 H) | B |

TABLE 2-continued

| EX | MS (ESI)+ m/z [M + H]+ | 1H NMR (600 MHz, DMSO-d6 d ppm (unless otherwise stated) | General proced. |
|---|---|---|---|
| 55 | 257 | 1H NMR (600 MHz, CD3OD) δ ppm 8.00 (s, 1 H) 7.63-7.69 (m, 1 H) 7.57-7.62 (m, 1 H) 6.96 (t, J = 2.14 Hz, 1 H) 6.86 (dd, J = 3.97, 1.83 Hz, 1 H) 6.23 (dd, J = 3.97, 2.75 Hz, 1 H) 4.08 (s, 3 H) | B |
| 56 | 255 | 1H NMR (600 MHz, CD3OD) δ ppm 9.31 (d, J = 1.53 Hz, 1 H) 8.72 (dd, J = 4.88, 1.53 Hz, 1 H) 8.51-8.60 (m, 1 H) 8.12 (s, 1 H) 7.73-7.78 (m, 1 H) 7.70-7.73 (m, 1 H) 7.67 (dd, 1 H) | B |
| 57 | 243 | 1H NMR (600 MHz, CD3OD) δ ppm 7.99 (s, 1 H) 7.69 (d, J = 7.93 Hz, 1 H) 7.60 (d, J = 8.24 Hz, 1 H) 7.12 (br. s., 1 H) 7.01 (br. s., 1 H) 6.35 (br. s., 1 H) | B |
| 58 | 260 | 1H NMR (600 MHz, CD3OD) δ ppm 8.27 (br. s., 1 H) 8.07 (s, 1 H) 7.80 (dd, J = 5.19, 1.22 Hz, 1 H) 7.72-7.77 (m, 1 H) 7.65-7.71 (m, 2 H) | B |
| 59 | 258 | 1H NMR (600 MHz, CD3OD) δ ppm 8.00 (s, 1 H) 7.68 (dd, J = 8.55, 1.53 Hz, 1 H) 7.61 (d, J = 8.24 Hz, 1 H) 7.17 (d, J = 3.36 Hz, 1 H) 6.30-6.35 (m, 1 H) 2.46 (s, 3 H) | B |
| 60 | 320 | 1H NMR (600 MHz, CD3OD) δ ppm 8.08 (s, 1 H) 8.00-8.05 (m, 3 H) 7.75 (dd, J = 8.24, 1.53 Hz, 1 H) 7.66-7.71 (m, 1 H) 7.50-7.56 (m, 2 H) 7.44-7.49 (m, 1 H) | B |
| 61 | 274 | 1H NMR (600 MHz, CD3OD) δ ppm 8.05 (s, 1 H) 7.67-7.72 (m, 1 H) 7.63-7.66 (m, 1 H) 7.57 (d, J = 5.19 Hz, 1 H) 7.07 (d, J = 5.19 Hz, 1 H) 2.61 (s, 3 H) | B |
| 62 | 298 | 1H NMR (600 MHz, CD3OD) δ ppm 8.04 (s, 1 H) 7.70 (dd, J = 8.24, 1.53 Hz, 1 H) 7.67 (dd, J = 7.93, 1.83 Hz, 1 H) 7.63-7.66 (m, 1 H) 7.59 (d, J = 1.83 Hz, 1 H) 7.03 (d, J = 8.24 Hz, 1 H) 6.09 (s, 2 H) | B |
| 63 | 294 | 1H NMR (600 MHz, CD3OD) δ ppm 8.10 (br. s., 1 H) 7.63-7.81 (m, 5 H) 7.42-7.51 (m, 1 H) 7.30-7.40 (m, 1 H) | B |
| 64 | 307 | 1H NMR (600 MHz, CD3OD) δ ppm 8.28 (d, 1 H) 8.06 (s, 1 H) 8.04 (s, 1 H) 7.70-7.74 (m, 1 H) 7.64-7.68 (m, 1 H) 7.57 (d, J = 8.24 Hz, 1 H) 7.31-7.41 (m, 2 H) 3.97 (s, 3 H) | B |
| 65 | 269 | 1H NMR (600 MHz, CD3OD) δ ppm 8.09-8.15 (m, 2 H) 7.88 (t, J = 7.78 Hz, 1 H) 7.67-7.77 (m, 2 H) 7.41 (d, J = 7.63 Hz, 1 H) 2.67 (s, 3 H) | B |
| 66 | 305 | 1H NMR (600 MHz, CD3OD) δ ppm 9.07 (d, 1 H) 8.80 (d, J = 7.93 Hz, 1 H) 8.18-8.23 (m, 2 H) 7.96 (d, J = 4.58 Hz, 1 H) 7.92 (ddd, J = 8.47, 6.94, 1.37 Hz, 1 H) 7.81 (d, J = 0.92 Hz, 2 H) 7.78 (td, J = 7.78, 1.22 Hz, 1 H) | B |
| 67 | 338 | 1H NMR (600 MHz, CD3OD) δ ppm 8.02 (br. s., 1 H) 7.54-7.79 (m, 4 H) | B |
| 68 | 307 | 1H NMR (600 MHz, CD3OD) δ ppm 8.09 (s, 1 H) 7.88-7.95 (m, 1 H) 7.72-7.76 (m, 1 H) 7.68-7.72 (m, 1 H) 7.39-7.45 (m, 1 H) 7.16-7.25 (m, 2 H) 2.77 (s, 3 H) | B |
| 69 | 293 | 1H NMR (600 MHz, CD3OD) δ ppm 8.25-8.30 (m, 1 H) 8.13 (s, 1 H) 8.07 (d, J = 0.92 Hz, 1 H) 7.71-7.75 (m, 1 H) 7.66-7.69 (m, 1 H) 7.51-7.57 (m, 1 H) 7.27-7.34 (m, 2 H) | B |
| 70 | 294 | 1H NMR (600 MHz, CD3OD) δ ppm 8.01 (br. s., 1 H) 7.68 (br. s., 1 H) 7.63 (d, J = 3.97 Hz, 1 H) 7.60 (br. s., 1 H) 7.14 (d, 1 H) | B |
| 71 | 305 | n.a. | B |
| 72 | 322 | 1H NMR (600 MHz, CD3OD) δ ppm 8.03 (br. s., 1 H) 7.51-7.80 (m, 2 H) 7.24 (d, J = 3.66 Hz, 1 H) 6.71 (d, 1 H) | B |
| 73 | 280 | 1H NMR (600 MHz, CD3OD) δ ppm 8.03 (d, J = 1.22 Hz, 1 H) 7.61-7.75 (m, 5 H) 7.43-7.48 (m, 2 H) 7.37-7.41 (m, 1 H) 7.20 (d, J = 16.48 Hz, 1 H) | B |
| 74 | 338 | 1H NMR (600 MHz, CD3OD) δ ppm 8.00 (br. s., 1 H) 7.65-7.72 (m, 1 H) 7.62 (br. s., 1 H) 7.59 (d, J = 3.97 Hz, 1 H) 7.26 (d, 1 H) | B |
| 75 | 248 | 1H NMR (600 MHz, CD3OD) δ ppm 8.05 (s, 1 H) 7.75 (dd, J = 8.39, 1.07 Hz, 1 H) 7.66 (d, J = 8.55 Hz, 1 H) 2.89 (s, 2 H) 1.07 (s, 9 H) | B |
| 76 | 282 | 1H NMR (600 MHz, CD3OD) δ ppm 8.00 (s, 1 H) 7.72 (dd, J = 8.54, 1.53 Hz, 1 H) 7.61 (d, J = 8.55 Hz, 1 H) 7.22-7.28 (m, 2 H) 7.14-7.22 (m, 3 H) 3.27-3.30 (m, 2 H, overlap with solvent peak) 3.19 (t, J = 7.78 Hz, 2 H) | B |
| 77 | 286 | 1H NMR (600 MHz, CD3OD) δ ppm 8.06 (d, 1 H) 7.69-7.75 (m, 1 H) 7.64-7.69 (m, 1 H) 3.82 (s, 3 H) 2.50 (s, 3 H) 2.41 (s, 3 H) | B |
| 78 | 234 | 1H NMR (600 MHz, CD3OD) δ ppm 7.99 (d, J = 1.22 Hz, 1 H) 7.69 (dd, J = 8.55, 1.53 Hz, 1 H) 7.59 (d, J = 8.85 Hz, 1 H) 2.93-3.02 (m, 2 H) 1.85 (dt, J = 15.26, 7.63 Hz, 2 H) 1.44 (dq, J = 14.92, 7.44 Hz, 2 H) 0.99 (t, J = 7.48 Hz, 3 H) | B |
| 79 | 248 | 1H NMR (600 MHz, CD3OD) δ ppm 8.01 (s, 1 H) 7.70 (dd, J = 8.55, 1.53 Hz, 1 H) 7.62 (d, J = 8.24 Hz, 1 H) 2.83-2.91 (m, 1 H) 1.78-1.93 (m, 4 H) 0.87 (t, J = 7.32 Hz, 6 H) | B |
| 80 | 278 | 11.25 (br. s., 1 H) 8.20 (d, J = 8.5 Hz, 2 H) 8.04 (s, 1 H) 7.55-7.78 (m, 4 H) 4.42 (s, 1 H) | C |

TABLE 2-continued

| EX | MS (ESI)+ m/z [M + H]+ | 1H NMR (600 MHz, DMSO-d6 d ppm (unless otherwise stated) | General proced. |
|---|---|---|---|
| 81 | 326 | 11.30 (br. s., 1 H) 8.09 (d, J = 2.4 Hz, 2 H) 7.76 (br. s., 2 H) 7.50 (d, J = 7.0 Hz, 1 H) 7.03 (d, J = 8.5 Hz, 1 H) 1.35 (s, 9 H) | C |
| 82 | 402 | 11.23 (br. s., 1 H) 8.01 (s, 1 H) 7.95 (d, J = 8.2 Hz, 1 H) 7.83 (d, J = 1.8 Hz, 1 H) 7.63-7.72 (m, 2 H) 7.60 (t, J = 8.1 Hz, 1 H) 7.46 (d, J = 8.5 Hz, 2 H) 7.18 (dd, J = 7.8, 2.0 Hz, 1 H) 7.04 (q, J = 5.2 Hz, 2 H) 1.31 (s, 9 H) | C |
| 83 | 344 | 11.27 (br. s., 1 H) 8.22 (d, J = 7.9 Hz, 1 H) 8.17 (s, 1 H) 8.04 (s, 1 H) 7.64-7.75 (m, 3 H) 7.56 (d, J = 7.6 Hz, 1 H) 7.28-7.39 (m, 4 H) 2.30 (s, 3 H) | C |
| 84 | 270 | 8.03-8.08 (m, 2 H) 8.01 (s, 1 H) 7.76 (d, J = 7.93 Hz, 1 H) 7.69 (d, J = 8.24 Hz, 1 H) 7.01 (d, J = 8.85 Hz, 2 H) | C |
| 85 | 300 | 8.08 (s, 1 H) 7.70-7.80 (m, 2 H) 7.65 (dd, J = 7.93, 1.22 Hz, 1 H) 7.16 (d, J = 7.93 Hz, 1 H) 7.00 (t, J = 7.93 Hz, 1 H) 3.86 (s, 3 H) | C |
| 86 | 320 | 8.16 (s, 1 H) 8.08 (d, J = 8.85 Hz, 1 H) 7.96 (d, J = 7.93 Hz, 2 H) 7.74-7.89 (m, 2 H) 7.54 (ddd, J = 8.47, 7.10, 1.22 Hz, 1 H) 7.43 (t, J = 7.63 Hz, 1 H) 7.39 (d, J = 9.16 Hz, 1 H) | C |
| 87 | 298 | 11.30 (br. s., 1 H) 8.09-8.18 (m, 2 H) 8.02 (s, 1 H) 7.74 (d, J = 8.24 Hz, 1 H) 7.64-7.71 (m, 1 H) 7.19 (d, J = 8.55 Hz, 2 H) 4.16 (q, J = 7.02 Hz, 2 H) 1.38 (t, J = 6.87 Hz, 3 H) | C |
| 88 | 261 | 11.24 (br. s., 1 H) 8.99 (br. s., 1 H) 8.11 (d, J = 3.05 Hz, 1 H) 8.01 (d, J = 3.05 Hz, 1 H) 7.70 (br. s., 2 H) | C |
| 89 | 300 | 11.35 (br. s., 1 H) 8.09 (s, 1 H) 8.05 (d, J = 8.54 Hz, 1 H) 7.77-7.82 (m, 1 H) 7.74 (d, J = 8.24 Hz, 1 H) 6.70 (d, J = 1.83 Hz, 1 H) 6.66 (dd, J = 8.70, 1.68 Hz, 1 H) 4.02 (s, 3 H) | C |
| 90 | 284 | 11.33 (br. s., 1 H) 7.79 (d, J = 7.63 Hz, 1 H) 7.72 (d, J = 8.24 Hz, 1 H) 7.62 (d, J = 7.93 Hz, 1 H) 6.78-6.87 (m, 2 H) 2.52 (s, 3 H) | C |
| 91 | 288 | 11.28 (br. s., 1 H) 8.09 (br. s., 1 H) 7.90 (d, J = 8.24 Hz, 1 H) 7.68-7.79 (m, 2 H) 7.35-7.44 (m, 1 H) 7.04 (td, J = 8.09, 4.88 Hz, 1 H) | C |
| 92 | 270 | 11.26 (br. s., 1 H) 9.87 (br. s., 1 H) 8.03 (s, 1 H) 7.69-7.75 (m, 1 H) 7.64-7.68 (m, 1 H) 7.57-7.63 (m, 2 H) 7.40 (t, J = 8.09 Hz, 1 H) 6.94-6.99 (m, 1 H) | C |
| 93 | 300 | 11.33 (br. s., 1 H) 8.02 (s, 1 H) 7.74-7.82 (m, 2 H) 7.64-7.73 (m, 2 H) 7.01 (d, J = 8.24 Hz, 1 H) 3.91 (s, 3 H) | C |
| 94 | 270 | 11.29 (br. s., 1 H) 8.02-8.12 (m, 2 H) 7.70-7.79 (m, 2 H) 7.46 (t, J = 7.63 Hz, 1 H) 7.04-7.13 (m, 2 H) | C |
| 95 | 268 | 11.30 (br. s., 1 H) 8.09 (s, 1 H) 7.66-7.81 (m, 3 H) 7.39-7.53 (m, 3 H) 2.58 (s, 3 H) | C |
| 96 | 296 | 11.31 (br. s., 1 H) 8.08 (s, 1 H) 8.02 (s, 1 H) 7.98 (dd, J = 8.55, 1.83 Hz, 1 H) 7.76 (d, J = 8.24 Hz, 1 H) 7.69 (d, J = 8.24 Hz, 1 H) 7.04 (d, J = 8.54 Hz, 1 H) 4.68 (t, J = 8.70 Hz, 2 H) 3.32 (t, J = 8.70 Hz, 2 H) | C |
| 97 | 312 | 11.31 (br. s., 1 H) 8.10-8.17 (m, 2 H) 8.03 (s, 1 H) 7.73-7.78 (m, 1 H) 7.65-7.73 (m, 1 H) 7.13-7.23 (m, 2 H) 4.79 (dt, J = 11.98, 6.07 Hz, 1 H) 1.32 (d, J = 6.10 Hz, 6 H) | C |
| 98 | 260 | 11.21 (br. s., 1 H) 7.96 (s, 1 H) 7.90 (dd, J = 3.66, 0.92 Hz, 1 H) 7.80 (dd, J = 5.04, 1.07 Hz, 1 H) 7.66 (dd, J = 8.55, 1.53 Hz, 1 H) 7.57-7.62 (m, 1 H) 7.27 (dd, J = 5.04, 3.81 Hz, 1 H) | C |
| 99 | 304 | 11.27 (br. s., 1 H) 8.19 (d, J = 2.44 Hz, 1 H) 8.08 (br. s., 1 H) 7.67-7.81 (m, 2 H) 7.45 (dd, J = 8.85, 2.75 Hz, 1 H) 7.10 (d, J = 8.85 Hz, 1 H) | C |
| 100 | 298 | 11.35 (br. s., 1 H) 9.94 (br. s., 1 H) 8.10 (s, 1 H) 7.84 (d, J = 8.85 Hz, 1 H) 7.77 (d, J = 8.24 Hz, 1 H) 6.66 (s, 2 H) 2.09 (s, 6 H) | C |
| 101 | 286 | 11.25 (br. s., 1 H) 8.15 (dd, J = 7.3, 1.5 Hz, 1 H) 7.90-8.10 (m, 2 H) 7.59-7.79 (m, 2 H) 7.39 (t, J = 9.2 Hz, 1 H) 2.36 (s, 3 H) | C |
| 102 | 288 | 11.20 (br. s., 1 H) 7.93 (s, 1 H) 7.65 (dd, J = 8.2, 1.5 Hz, 1 H) 7.62 (s, 1 H) 7.57 (d, J = 8.5 Hz, 1 H) 2.39 (s, 3 H) 2.18 (s, 3 H) | C |
| 103 | 282 | 11.29 (br. s., 1 H) 8.08 (s, 1 H) 7.68-7.85 (m, 2 H) 7.60 (s, 1 H) 7.20-7.38 (m, 2 H) 2.54 (s, 3 H) 2.38 (s, 3 H) | C |
| 104 | 282 | 11.30 (br. s., 1 H) 8.07 (s, 1 H) 7.69-7.79 (m, 2 H) 7.67 (d, J = 7.6 Hz, 1 H) 7.27 (s, 1 H) 7.25 (d, J = 8.2 Hz, 1 H) 2.56 (s, 3 H) 2.38 (s, 3 H) | C |
| 105 | 282 | 11.29 (br. s., 1 H) 8.01 (d, J = 17.4 Hz, 2 H) 7.92 (dd, J = 7.8, 1.7 Hz, 1 H) 7.74 (d, 1 H) 7.68 (d, J = 7.9 Hz, 1 H) 7.39 (d, J = 7.9 Hz, 1 H) 2.35 (s, 3 H) 2.33 (s, 3 H) | C |
| 106 | 286 | 11.24 (br. s., 1 H) 8.02 (s, 1 H) 7.94 (t, J = 8.1 Hz, 2 H) 7.63-7.74 (m, 2 H) 7.52 (t, J = 8.1 Hz, 1 H) 7.37 (1 H) 2.33 (s, 3 H) | C |
| 107 | 282 | 11.31 (br. s., 1 H) 8.09 (s, 1 H) 7.68-7.82 (m, 2 H) 7.53 (d, J = 7.9 Hz, 1 H) 7.42 (d, J = 7.3 Hz, 1 H) 7.32 (t, J = 7.6 Hz, 1 H) 2.39 (s, 3 H) 2.36 (s, 3 H) | C |
| 108 | 334 | 11.23 (br. s., 1 H) 9.05 (s, 1 H) 8.02 (s, 1 H) 7.83 (d, J = 7.6 Hz, 2 H) 7.64-7.77 (m, 2 H) 7.56 (d, J = 8.5 Hz, 1 H) 7.38 (t, J = 7.5 Hz, 1 H) 2.67 (s, 3 H) | C |
| 109 | 282 | 11.28 (br. s., 1 H) 8.12 (d, J = 8.2 Hz, 2 H) 8.04 (s, 1 H) 7.61-7.85 (m, 2 H) 7.47 (d, J = 7.9 Hz, 2 H) 2.71 (q, J = 7.6 Hz, 2 H) 1.24 (t, J = 7.6 Hz, 3 H) | C |

TABLE 2-continued

| EX | MS (ESI)+ m/z [M + H]+ | 1H NMR (600 MHz, DMSO-d6 d ppm (unless otherwise stated) | General proced. |
|---|---|---|---|
| 110 | 282 | 11.26 (br. s., 1 H) 8.07 (s, 1 H) 7.62-7.82 (m, 3 H) 7.34-7.57 (m, 3 H) 2.97 (q, J = 7.6 Hz, 2 H) 1.10 (t, J = 7.5 Hz, 3 H) | C |
| 111 | 324 | 11.28 (br. s., 1 H) 8.11 (d, J = 8.5 Hz, 2 H) 8.03 (s, 1 H) 7.64-7.76 (m, 2 H) 7.45 (d, J = 8.2 Hz, 2 H) 2.67 (t, J = 7.8 Hz, 2 H) 1.63 (ddd, J = 14.8, 7.6, 7.5 Hz, 2 H) 1.26-1.38 (m, 4 H) 0.88 (t, J = 7.0 Hz, 3 H) | C |
| 112 | 307 | 11.22 (br. s., 1 H) 8.04 (br. s., 1 H) 7.55-7.74 (m, 3 H) 7.30 (t, J = 7.6 Hz, 3 H) 7.14 (t, J = 7.5 Hz, 1 H) 4.31 (s, 3 H) | C |
| 113 | 376 | 11.22 (br. s., 1 H) 8.00 (s, 1 H) 7.89 (d, J = 8.2 Hz, 1 H) 7.72-7.76 (m, 1 H) 7.61-7.70 (m, 2 H) 7.57 (t, J = 7.9 Hz, 1 H) 7.08-7.16 (m, 3 H) 7.02 (d, J = 9.2 Hz, 2 H) 3.78 (s, 3 H) | C |
| 114 | 360 | 11.29 (br. s., 1 H) 8.48-8.51 (m, 1 H) 8.21 (d, J = 7.9 Hz, 1 H) 8.07 (s, 1 H) 7.90 (d, J = 8.2 Hz, 1 H) 7.71 (ddd, J = 15.0, 7.4, 7.2 Hz, 3 H) 7.47 (t, J = 7.8 Hz, 1 H) 7.38 (d, J = 7.6 Hz, 1 H) 7.34 (d, J = 2.1 Hz, 1 H) 7.03 (dd, J = 8.2, 2.4 Hz, 1 H) 3.87 (s, 3 H) | C |
| 115 | 382 | 11.33 (br. s., 1 H) 8.02 (s, 1 H) 7.98 (s, 2 H) 7.73 (br. s., 2 H) 1.47 (s, 18 H) | C |
| 116 | 349/351 | 11.24 (br. s., 1 H) 8.12 (dd, J = 9.8, 1.8 Hz, 1 H) 8.04 (s, 1 H) 7.91-8.00 (m, 2 H) 7.62-7.75 (m, 2 H) | C |
| 117 | 306 | 11.24 (br. s., 1 H) 8.17 (dd, J = 10.4, 2.1 Hz, 1 H) 8.05 (dd, J = 9.0, 7.5 Hz, 2 H) 7.83 (t, J = 8.1 Hz, 1 H) 7.60-7.74 (m, 2 H) | C |
| 118 | 272 | 11.24 (br. s., 1 H) 7.94-8.09 (m, 3 H) 7.60-7.74 (m, 3 H) 7.40 (td, J = 8.5, 1.8 Hz, 1 H) | C |
| 119 | 330 | 11.24 (br. s., 1 H) 7.94 (s, 1 H) 7.80 (d, J = 7.6 Hz, 1 H) 7.67-7.74 (m, 2 H) 7.60 (d, J = 7.9 Hz, 3 H) 7.28 (d, J = 1.2 Hz, 3 H) 7.18-7.23 (m, 2 H) | C |
| 120 | 272 | 11.23 (br. s., 1 H) 8.23 (td, J = 7.7, 1.7 Hz, 1 H) 8.07 (s, 1 H) 7.56-7.78 (m, 3 H) 7.48 (dd, J = 11.0, 7.9 Hz, 2 H) | C |
| 121 | 312 | 11.31 (br. s., 1 H) 8.14 (d, J = 8.9 Hz, 2 H) 8.03 (s, 1 H) 7.58-7.84 (m, 2 H) 7.20 (d, J = 8.9 Hz, 2 H) 4.06 (t, J = 6.6 Hz, 2 H) 1.78 (q, J = 6.7 Hz, 2 H) 1.01 (t, J = 7.5 Hz, 3 H) | D |
| 122 | 326 | 11.31 (br. s., 1 H) 8.14 (d, J = 8.9 Hz, 2 H) 8.03 (s, 1 H) 7.66-7.82 (m, 2 H) 7.21 (d, J = 8.9 Hz, 2 H) 3.88 (d, J = 6.7 Hz, 2 H) 2.07 (dt, J = 13.4, 6.6 Hz, 1 H) 1.01 (d, J = 6.7 Hz, 6 H) | D |
| 123 | 372 | 11.30 (br. s., 1 H) 8.14 (d, J = 8.9 Hz, 2 H) 8.03 (s, 1 H) 7.62-7.80 (m, 2 H) 7.22 (d, J = 8.9 Hz, 2 H) 4.22 (d, J = 4.6 Hz, 2 H) 3.79 (d, J = 4.6 Hz, 2 H) 3.61 (dd, J = 5.6, 3.8 Hz, 2 H) 3.47 (dd, J = 5.5, 4.0 Hz, 2 H) 3.26 (s, 3 H) | D |
| 124 | 383 | 8.12 (d, J = 8.9 Hz, 2 H) 7.96 (br. s., 1 H) 7.51-7.69 (m, 2 H) 7.08-7.20 (m, 2 H) 4.19 (t, J = 5.6 Hz, 2 H) 3.59 (t, J = 4.7 Hz, 4 H) 2.73 (t, J = 5.8 Hz, 2 H) | D |
| 125 | 369 | 8.12 (d, J = 8.9 Hz, 2 H) 7.96 (br. s., 1 H) 7.53-7.65 (m, 2 H) 7.12 (d, J = 8.9 Hz, 2 H) 2.80 (t, J = 6.1 Hz, 2 H) 2.56 (q, J = 7.0 Hz, 4 H) 0.99 (t, J = 7.0 Hz, 6 H) | D |
| 126 | 342 | 11.30 (br. s., 1 H) 8.14 (d, J = 8.9 Hz, 2 H) 8.02 (s, 1 H) 7.58-7.81 (m, 2 H) 7.21 (d, J = 8.9 Hz, 2 H) 4.22 (d, J = 4.6 Hz, 2 H) 3.74 (d, J = 4.6 Hz, 2 H) 3.52 (q, J = 7.0 Hz, 2 H) 1.14 (t, J = 7.0 Hz, 3 H) | D |
| 127 | 390 | 11.31 (br. s., 1 H) 8.17 (d, J = 8.9 Hz, 2 H) 8.03 (s, 1 H) 7.62-7.83 (m, 2 H) 7.19-7.39 (m, 4 H) 6.82-7.07 (m, 3 H) 4.46 (dd, J = 5.3, 3.2 Hz, 2 H) 4.36 (dd, J = 5.3, 3.2 Hz, 2 H) | D |
| 128 | 312 | 11.28 (br. s., 1 H) 8.04 (s, 1 H) 7.62-7.85 (m, 4 H) 7.51 (t, J = 8.1 Hz, 1 H) 7.14 (d, J = 7.0 Hz, 1 H) 4.06 (t, J = 6.6 Hz, 2 H) 1.80 (q, J = 6.7 Hz, 2 H) 1.03 (t, J = 7.5 Hz, 3 H) | D |
| 129 | 326 | 11.28 (br. s., 1 H) 8.04 (s, 1 H) 7.61-7.85 (m, 4 H) 7.51 (t, J = 7.9 Hz, 1 H) 7.15 (dd, J = 8.2, 1.8 Hz, 1 H) 3.87 (d, J = 6.7 Hz, 2 H) 2.08 (dt, J = 13.2, 6.7 Hz, 1 H) 1.03 (d, J = 6.7 Hz, 6 H) | D |
| 130 | 372 | 11.28 (br. s., 1 H) 8.04 (s, 1 H) 7.62-7.87 (m, 4 H) 7.52 (t, J = 8.1 Hz, 1 H) 7.17 (dd, J = 8.2, 1.8 Hz, 1 H) 4.22 (d, J = 4.6 Hz, 2 H) 3.81 (d, J = 4.6 Hz, 2 H) 3.62 (dd, J = 5.5, 4.0 Hz, 2 H) 3.42-3.55 (m, 2 H) 3.26 (s, 3 H) | D |
| 131 | 383 | 11.23 (br. s., 1 H) 8.02 (s, 1 H) 7.85-7.88 (m, 1 H) 7.83 (d, J = 7.93 Hz, 1 H) 7.67-7.72 (m, 1 H) 7.63-7.67 (m, 1 H) 7.55 (t, J = 7.93 Hz, 1 H) 7.19 (dd, J = 7.94, 2.44 Hz, 1 H) 4.47-4.52 (m, 2 H) 4.00 (br. s., 2 H) 3.73 (br. s., 2 H) 3.65 (br. s., 2 H) 3.56 (br. s., 2 H) 3.26 (br. s., 2 H) | D |
| 132 | 369 | 11.23 (br. s., 1 H) 9.35 (br. s., 1 H) 8.02 (s, 1 H) 7.86 (br. s., 1 H) 7.83 (d, J = 7.93 Hz, 1 H) 7.67-7.70 (m, 1 H) 7.64-7.67 (m, 1 H) 7.55 (t, J = 7.93 Hz, 1 H) 7.18 (dd, J = 8.24, 2.14 Hz, 1 H) 4.44 (t, J = 4.88 Hz, 2 H) 3.60 (q, J = 4.68 Hz, 2 H) 3.20-3.34 (m, 4 H) 1.27 (t, J = 7.32 Hz, 6 H) | D |
| 133 | 342 | 11.28 (br. s., 1 H) 8.04 (s, 1 H) 7.76-7.81 (m, 2 H) 7.71-7.75 (m, 1 H) 7.66-7.71 (m, 1 H) 7.52 (t, J = 8.24 Hz, 1 H) 7.17 (dd, J = 8.24, 1.83 Hz, 1 H) 4.15-4.26 (m, 2 H) 3.71-3.81 (m, 2 H) 3.54 (q, J = 7.02 Hz, 2 H) 1.15 (t, J = 7.02 Hz, 3 H) | D |

TABLE 2-continued

| EX | MS (ESI)+ m/z [M + H]+ | ¹H NMR (600 MHz, DMSO-d₆ d ppm (unless otherwise stated) | General proced. |
|---|---|---|---|
| 134 | 390 | 11.28 (br. s., 1 H) 8.04 (s, 1 H) 7.82-7.85 (m, 1 H) 7.81 (d, J = 7.93 Hz, 1 H) 7.71-7.76 (m, 1 H) 7.65-7.71 (m, 1 H) 7.54 (t, J = 7.93 Hz, 1 H) 7.29-7.35 (m, 2 H) 7.21 (dd, J = 8.24, 2.14 Hz, 1 H) 6.99-7.05 (m, 2 H) 6.96 (t, J = 7.32 Hz, 1 H) 4.42-4.48 (m, 2 H) 4.34-4.41 (m, 2 H) | D |
| 135 | 397 | 11.28 (br. s., 1 H) 8.04 (s, 1 H) 7.75-7.81 (m, 2 H) 7.71-7.75 (m, 1 H) 7.66-7.71 (m, 1 H) 7.52 (t, J = 7.93 Hz, 1 H) 7.07-7.20 (m, 1 H) 4.97 (s, 2 H) 3.55-3.72 (m, 4 H) 3.39-3.55 (m, 4 H) | D |
| 136 | 314 | 11.28 (br. s., 1 H) 8.04 (s, 1 H) 7.76-7.81 (m, 2 H) 7.71-7.74 (m, 1 H) 7.65-7.71 (m, 1 H) 7.52 (t, J = 8.09 Hz, 1 H) 7.15 (dd, J = 8.09, 1.98 Hz, 1 H) 4.12 (t, J = 5.04 Hz, 2 H) 3.78 (t, J = 5.04 Hz, 2 H) | D |
| 137 | 312 | 11.33 (br. s., 1 H) 8.06-8.20 (m, 2 H) 7.72-7.85 (m, 2 H) 7.61 (t, J = 7.32 Hz, 1 H) 7.35 (d, J = 8.24 Hz, 1 H) 7.20 (t, J = 7.48 Hz, 1 H) 4.25 (t, J = 6.71 Hz, 2 H) 1.76-1.94 (m, J = 7.32, 7.17, 7.17, 7.17 Hz, 2 H) 0.94 (t, J = 7.32 Hz, 3 H) | D |
| 138 | 326 | 11.33 (br. s., 1 H) 8.13 (s, 1 H) 8.09 (dd, J = 7.63, 1.53 Hz, 1 H) 7.74-7.83 (m, 2 H) 7.56-7.65 (m, 1 H) 7.35 (d, J = 8.24 Hz, 1 H) 7.20 (t, J = 7.48 Hz, 1 H) 4.05 (d, J = 6.71 Hz, 2 H) 2.17-2.28 (m, J = 13.43, 6.71, 6.71, 6.71, 6.71 Hz, 1 H) 0.93 (d, J = 6.71 Hz, 6 H) | D |
| 139 | 372 | 11.32 (br. s., 1 H) 8.19 (dd, J = 7.6, 1.5 Hz, 1 H) 8.12 (s, 1 H) 7.72-7.89 (m, 2 H) 7.61 (dd, J = 15.6, 1.5 Hz, 1 H) 7.38 (d, J = 8.2 Hz, 1 H) 7.23 (t, J = 7.3 Hz, 1 H) 4.42 (d, J = 4.9 Hz, 2 H) 3.92 (d, J = 4.9 Hz, 2 H) 3.62 (d, J = 4.9 Hz, 2 H) 3.32-3.45 (m, 2 H) 3.12 (s, 3 H) | D |
| 140 | 383 | 11.27 (br. s., 1 H) 7.99-8.15 (m, 2 H) 7.72 (q, J = 8.2 Hz, 2 H) 7.60 (dd, J = 15.7, 1.7 Hz, 1 H) 7.36 (d, J = 8.2 Hz, 1 H) 7.24 (t, J = 7.5 Hz, 1 H) 4.61 (d, J = 5.2 Hz, 2 H) 3.62-3.88 (m, 6 H) 3.37 (br. s., 4 H) | D |
| 141 | 369 | 11.29 (br. s., 1 H) 8.06 (dd, J = 9.8, 1.8 Hz, 2 H) 7.69-7.81 (m, 2 H) 7.62 (dd, J = 15.7, 1.7 Hz, 1 H) 7.37 (d, J = 8.2 Hz, 1 H) 7.26 (t, J = 7.5 Hz, 1 H) 4.58 (t, J = 4.9 Hz, 2 H) 3.70 (d, J = 4.9 Hz, 2 H) 3.28 (q, J = 7.2 Hz, 4 H) 1.17 (t, J = 7.3 Hz, 6 H) | D |
| 142 | 342 | 11.31 (br. s., 1 H) 8.19 (dd, J = 7.6, 1.5 Hz, 1 H) 8.11 (s, 1 H) 7.67-7.86 (m, 2 H) 7.60 (dd, J = 15.7, 1.4 Hz, 1 H) 7.38 (d, J = 8.2 Hz, 1 H) 7.22 (t, J = 7.5 Hz, 1 H) 4.42 (d, J = 4.9 Hz, 2 H) 3.88 (d, J = 4.6 Hz, 2 H) 3.54 (q, J = 7.0 Hz, 2 H) 1.07 (t, J = 7.0 Hz, 3 H) | D |
| 143 | 390 | 11.32 (br. s., 1 H) 8.15 (d, J = 1.5 Hz, 1 H) 8.09 (s, 1 H) 7.57-7.82 (m, 3 H) 7.46 (d, J = 8.2 Hz, 1 H) 7.22 (dd, J = 8.9, 7.3 Hz, 3 H) 6.81-6.98 (m, 3 H) 4.65 (d, J = 4.9 Hz, 2 H) 4.50 (d, J = 4.9 Hz, 2 H) | D |
| 144 | 397 | 11.32 (br. s., 1 H) 8.35 (dd, J = 7.9, 1.5 Hz, 1 H) 8.10 (s, 1 H) 7.67-7.86 (m, 2 H) 7.61 (t, J = 7.3 Hz, 1 H) 7.36 (d, J = 8.2 Hz, 1 H) 7.26 (t, J = 7.5 Hz, 1 H) 5.29 (s, 2 H) 3.64 (dd, J = 12.8, 4.6 Hz, 8 H) | D |
| 145 | 302 | ¹H NMR (600 MHz, CD₃OD) δ ppm 7.98 (d, J = 1.22 Hz, 1 H) 7.67 (dd, J = 8.55, 1.53 Hz, 1 H) 7.58 (d, J = 8.24 Hz, 1 H) 7.29-7.38 (m, 4 H) 4.30 (s, 2 H) | E |
| 146 | 286 | ¹H NMR (600 MHz, CD₃OD) δ ppm 7.99 (d, J = 0.92 Hz, 1 H) 7.69 (dd, J = 8.54, 1.53 Hz, 1 H) 7.60 (d, J = 8.55 Hz, 1 H) 7.31-7.40 (m, 2 H) 7.05-7.13 (m, 2 H) 4.31 (s, 2 H) | E |
| 147 | 260 | ¹H NMR (600 MHz, CD₃OD) δ ppm 7.99 (d, J = 1.22 Hz, 1 H) 7.68 (dd, J = 8.55, 1.53 Hz, 1 H) 7.60 (d, J = 8.24 Hz, 1 H) 3.00 (tt, J = 11.94, 3.47 Hz, 1 H) 2.07-2.18 (m, 2 H) 1.92 (dt, J = 13.43, 3.36 Hz, 2 H) 1.77-1.85 (m, 1 H) 1.64-1.75 (m, J = 12.67, 12.44, 12.44, 3.36 Hz, 2 H) 1.50 (qt, J = 12.89, 3.24 Hz, 2 H) 1.33-1.43 (m, 1 H) | E |
| 148 | 360 | ¹H NMR (600 MHz, CD₃OD) δ ppm 8.38 (t, J = 1.68 Hz, 1 H) 8.09 (s, 1 H) 8.01-8.06 (m, 1 H) 7.75-7.81 (m, 1 H) 7.67-7.74 (m, 4 H) 7.62 (t, J = 7.78 Hz, 1 H) 6.99-7.11 (m, 2 H) 3.86 (s, 3 H) | F |
| 149 | 364 | ¹H NMR (600 MHz, CD₃OD) δ ppm 8.43 (t, J = 1.53 Hz, 1 H) 8.12-8.17 (m, 1 H) 8.10 (s, 1 H) 7.82-7.88 (m, 1 H) 7.80 (t, J = 1.83 Hz, 1 H) 7.65-7.74 (m, 4 H) 7.50 (t, J = 7.78 Hz, 1 H) 7.41-7.45 (m, 1 H) | F |
| 150 | 360 | ¹H NMR (600 MHz, CD₃OD) δ ppm 8.14-8.21 (m, 2 H) 8.08 (s, 1 H) 7.77-7.84 (m, 2 H) 7.64-7.74 (m, 4 H) 7.00-7.09 (m, 2 H) 3.86 (s, 3 H) | G |
| 151 | 364 | ¹H NMR (600 MHz, CD₃OD) δ ppm 8.18-8.26 (m, 2 H) 8.09 (s, 1 H) 7.82-7.90 (m, 2 H) 7.61-7.77 (m, 4 H) 7.48 (t, J = 7.93 Hz, 1 H) 7.38-7.45 (m, 1 H) | G |
| 152 | 332 | ¹H NMR (600 MHz, CD₃OD) δ ppm 8.31-8.41 (m, 2 H) 8.14-8.21 (m, 2 H) 8.12 (br. s., 1 H) 7.73 (br. s., 2 H) 3.21 (s, 3 H) | H |
| 153 | 320 | ¹H NMR (600 MHz, CD₃OD) δ ppm 8.09 (d, J = 0.92 Hz, 1 H) 7.92-7.97 (m, 2 H) 7.77 (dd, J = 8.39, 1.68 Hz, 1 H) 7.68-7.73 (m, 1 H) 7.49 (t, J = 7.78 Hz, 2 H) 7.44 (d, J = 3.66 Hz, 1 H) 7.40 (t, J = 7.48 Hz, 1 H) 7.10 (d, 1 H) | I |
| 154 | 354 | ¹H NMR (600 MHz, CD₃OD) δ ppm 8.09 (d, 1 H) 8.02 (t, J = 1.68 Hz, 1 H) 7.85 (ddd, J = 8.01, 1.30, 1.07 Hz, 1 H) 7.76 (dd, J = 8.55, | I |

TABLE 2-continued

| EX | MS (ESI)+ m/z [M + H]+ | 1H NMR (600 MHz, DMSO-d6 d ppm (unless otherwise stated) | General proced. |
|---|---|---|---|
| | | 1.53 Hz, 1 H) 7.70 (d, J = 7.93 Hz, 1 H) 7.47 (t, J = 7.93 Hz, 1 H) 7.42 (d, J = 3.66 Hz, 1 H) 7.39 (ddd, J = 7.94, 2.14, 0.92 Hz, 1 H) 7.17 (d, J = 3.66 Hz, 1 H) | |
| 155 | 350 | 1H NMR (600 MHz, CD3OD) δ ppm 8.07 (d, 1 H) 7.84-7.89 (m, 2 H) 7.76 (dd, J = 8.24, 1.53 Hz, 1 H) 7.68 (d, J = 8.55 Hz, 1 H) 7.41 (d, J = 3.66 Hz, 1 H) 7.02-7.07 (m, 2 H) 6.94 (d, J = 3.66 Hz, 1 H) 3.86 (s, 3 H) | I |
| 156 | 338 | 1H NMR (600 MHz, CD3OD) δ ppm 8.19 (td, J = 7.78, 1.83 Hz, 1 H) 8.10 (d, J = 0.92 Hz, 1 H) 7.76-7.80 (m, 1 H) 7.71 (d, J = 8.55 Hz, 1 H) 7.48 (d, J = 3.66 Hz, 1 H) 7.41-7.46 (m, 1 H) 7.36 (td, J = 7.63, 1.22 Hz, 1 H) 7.27 (ddd, J = 11.44, 8.24, 1.07 Hz, 1 H) 7.12 (t, 1 H) | I |
| 157 | 321 | 1H NMR (600 MHz, CD3OD) δ ppm 9.26 (d, J = 1.53 Hz, 1 H) 8.65 (dd, J = 5.04, 1.37 Hz, 1 H) 8.51 (ddd, J = 8.24, 1.83, 1.53 Hz, 1 H) 8.15 (s, 1 H) 7.79-7.85 (m, 1 H) 7.74-7.78 (m, 1 H) 7.72 (dd, J = 8.09, 5.04 Hz, 1 H) 7.52 (d, J = 3.66 Hz, 1 H) 7.40 (d, 1 H) | I |
| 158 | 398 | 1H NMR (600 MHz, CD3OD) δ ppm 8.27-8.31 (m, 2 H) 8.18 (br. s., 1 H) 8.13-8.17 (m, 2 H) 7.84 (d, J = 8.55 Hz, 1 H) 7.78 (d, J = 7.63 Hz, 1 H) 7.51-7.55 (m, 1 H) 7.49 (d, J = 3.66 Hz, 1 H) 3.32 (s, 3 H) | I |
| 159 | 310 | 1H NMR (600 MHz, CD3OD) δ ppm 8.18 (s, 1 H) 8.05-8.12 (m, 2 H) 7.91 (dd, J = 8.55, 1.22 Hz, 1 H) 7.82 (d, J = 8.55 Hz, 1 H) 7.73-7.79 (m, 2 H) 1.41 (s, 9 H) | H |
| 160 | 312 | 1H NMR (600 MHz, CD3OD) δ ppm 8.17 (d, J = 0.61 Hz, 1 H) 7.90 (dd, J = 8.55, 1.53 Hz, 1 H) 7.85 (s, 2 H) 7.80 (dd, J = 8.54, 0.61 Hz, 1 H) 3.84 (s, 3 H) 2.43 (s, 6 H) | H |
| 161 | 380 | 1H NMR (600 MHz, CD3OD) δ ppm 8.17 (s, 1 H) 8.01-8.09 (m, 2 H) 7.89 (dd, J = 8.55, 1.53 Hz, 1 H) 7.80 (d, J = 8.54 Hz, 1 H) 7.50-7.57 (m, 2 H) 2.77 (t, J = 7.63 Hz, 2 H) 1.70 (quin, J = 7.40 Hz, 2 H) 1.22-1.44 (m, 12 H) 0.84-0.94 (m, 3 H) | H |
| 162 | 310 | 1H NMR (600 MHz, CD3OD) δ ppm 8.18 (d, J = 0.92 Hz, 1 H) 8.02-8.10 (m, 2 H) 7.91 (dd, J = 8.54, 1.22 Hz, 1 H) 7.82 (d, J = 8.55 Hz, 1 H) 7.48-7.58 (m, 2 H) 2.78 (t, J = 7.63 Hz, 2 H) 1.63-1.74 (m, 2 H) 1.36-1.46 (m, J = 14.95, 7.48, 7.48, 7.32 Hz, 2 H) 0.98 (t, J = 7.32 Hz, 3 H) | H |
| 163 | 348 | 8.39 (s, 1 H) 8.24 (d, J = 7.32 Hz, 1 H) 8.05 (s, 1 H) 7.62-7.79 (m, 5 H) 7.45-7.56 (m, 1 H) 7.32-7.43 (m, 2 H) | F |
| 164 | 408 | 8.58 (s, 1 H) 8.29 (d, J = 7.63 Hz, 1 H) 8.03-8.15 (m, 5 H) 7.96 (d, J = 7.93 Hz, 1 H) 7.64-7.81 (m, 3 H) 3.29 (s, 3 H) | F |
| 165 | 331 | 9.08 (d, J = 2.14 Hz, 1 H) 8.69 (dd, J = 4.73, 1.37 Hz, 1 H) 8.56 (s, 1 H) 8.31 (d, J = 7.93 Hz, 1 H) 8.28 (d, J = 7.63 Hz, 1 H) 8.05 (s, 1 H) 7.94 (d, J = 7.93 Hz, 1 H) 7.62-7.79 (m, 4 H) | F |
| 166 | 330 | 8.51 (s, 1 H) 8.21 (d, J = 7.93 Hz, 1 H) 8.06 (s, 1 H) 7.88 (d, J = 7.63 Hz, 1 H) 7.81 (d, J = 7.02 Hz, 2 H) 7.67-7.76 (m, 3 H) 7.55 (t, J = 7.78 Hz, 2 H) 7.45 (t, J = 7.32 Hz, 1 H) | F |
| 167 | 348 | 8.31 (d, J = 8.24 Hz, 2 H) 8.07 (s, 1 H) 7.82 (d, J = 7.02 Hz, 2 H) 7.69-7.76 (m, 2 H) 7.66 (td, J = 7.93, 1.53 Hz, 1 H) 7.45-7.53 (m, 1 H) 7.31-7.41 (m, 2 H) | G |
| 168 | 408 | 8.34 (d, J = 8.54 Hz, 2 H) 7.95-8.13 (m, 7 H) 7.63-7.79 (m, 2 H) 3.28 (s, 3 H) | G |
| 169 | 366 | 8.40 (s, 1 H) 8.27 (d, J = 7.63 Hz, 1 H) 8.05 (s, 1 H) 7.75-7.84 (m, 1 H) 7.65-7.75 (m, 3 H) 7.51-7.62 (m, 1 H) 7.41-7.50 (m, 1 H) 7.29-7.38 (m, 1 H) | F |
| 170 | 390 | 8.45 (s, 1 H) 8.15 (d, J = 7.93 Hz, 1 H) 8.07 (s, 1 H) 7.87 (d, J = 7.63 Hz, 1 H) 7.70-7.80 (m, 2 H) 7.67 (t, J = 7.78 Hz, 1 H) 7.30-7.41 (m, 2 H) 7.12 (d, J = 8.85 Hz, 1 H) 3.90 (s, 3 H) 3.83 (s, 3 H) | F |
| 171 | 398 | 8.57 (s, 1 H) 8.27 (d, J = 7.63 Hz, 1 H) 8.01-8.09 (m, 3 H) 7.95 (d, J = 7.63 Hz, 1 H) 7.91 (d, J = 8.24 Hz, 2 H) 7.68-7.79 (m, 3 H) | F |
| 172 | 398 | 8.34 (d, J = 8.55 Hz, 2 H) 7.99-8.07 (m, 5 H) 7.87 (d, J = 8.55 Hz, 2 H) 7.66-7.76 (m, 2 H) | G |
| 173 | 356 | 8.03 (s, 1 H) 8.01 (ddd, J = 9.23, 5.88, 3.20 Hz, 1 H) 7.69-7.73 (m, 1 H) 7.65-7.69 (m, 1 H) 7.47 (td, J = 9.77, 4.27 Hz, 1 H) 7.44 (d, J = 3.66 Hz, 1 H) 7.31 (td, J = 8.24, 3.66 Hz, 1 H) 7.17 (t, J = 3.51 Hz, 1 H) | I |
| 174 | 380 | 11.26 (br. s., 1 H) 8.02 (s, 1 H) 7.69-7.75 (m, 1 H) 7.63-7.69 (m, 1 H) 7.53 (dd, J = 8.39, 1.98 Hz, 1 H) 7.47 (d, J = 1.83 Hz, 1 H) 7.42 (d, J = 3.36 Hz, 1 H) 7.17 (d, J = 3.36 Hz, 1 H) 7.11 (d, J = 8.55 Hz, 1 H) 3.89 (s, 3 H) 3.83 (s, 3 H) | I |
| 175 | 388 | 8.16 (d, J = 8.24 Hz, 2 H) 8.03 (s, 1 H) 7.89 (d, J = 8.54 Hz, 2 H) 7.69-7.73 (m, 1 H) 7.64-7.68 (m, 1 H) 7.47 (d, J = 3.66 Hz, 1 H) 7.41-7.46 (m, 1 H) | I |
| 176 | 354 | 7.98 (s, 1 H) 7.87-7.94 (m, 2 H) 7.74 (d, J = 3.66 Hz, 1 H) 7.64-7.70 (m, 1 H) 7.58-7.65 (m, 1 H) 7.37-7.49 (m, 2 H) 7.34 (dd, J = 14.95, 1.22 Hz, 1 H) | J |

TABLE 2-continued

| EX | MS (ESI)+ m/z [M + H]+ | 1H NMR (600 MHz, DMSO-d6 d ppm (unless otherwise stated) | General proced. |
|---|---|---|---|
| 177 | 370 | N/A | J |
| 178 | 366 | 7.96 (s, 1 H) 7.85 (d, J = 3.66 Hz, 1 H) 7.68-7.71 (m, 2 H) 7.66 (dd, J = 8.24, 1.53 Hz, 1 H) 7.59 (d, J = 8.24 Hz, 1 H) 7.53 (d, J = 3.66 Hz, 1 H) 7.01-7.06 (m, 2 H) 3.81 (s, 3 H) | J |
| 179 | 336 | 7.97 (s, 1 H) 7.89 (d, J = 3.97 Hz, 1 H) 7.76 (d, J = 7.32 Hz, 2 H) 7.64-7.68 (m, 2 H) 7.58-7.63 (m, 1 H) 7.48 (t, J = 7.63 Hz, 2 H) 7.39 (t, J = 7.32 Hz, 1 H) | J |
| 180 | 248 | 11.25 (br. s., 1 H), 8.11 (td, J = 11.1, 1.7 Hz, 2 H), 8.05 (s, 1 H), 7.78 (t, J = 8.1 Hz, 1 H), 7.62-7.73 (m, 4 H), 7.53 (t, J = 7.6 Hz, 2 H), 7.46 (t, J = 7.3 Hz, 1 H) | K |
| 181 | 366 | 11.25 (br. s., 1 H), 8.15 (dd, J = 7.9, 1.5 Hz, 1 H), 8.12 (dd, J = 11.1, 1.7 Hz, 1 H), 8.06 (s, 1 H), 7.70 (d, J = 4.9 Hz, 3 H), 7.51-7.59 (m, 2 H), 7.35-7.42 (m, 2 H) | K |
| 182 | 382 | 11.25 (br. s., 1 H), 9.72 (br. s., 1 H), 7.97-8.11 (m, 2 H), 7.66-7.75 (m, 2 H), 7.62 (t, J = 7.8 Hz, 2 H), 7.10-7.15 (m, 2 H), 6.96 (dd, J = 8.9, 4.9 Hz, 2 H) | K |
| 183 | 366 | 11.25 (br. s., 1 H), 8.08-8.18 (m, 2 H), 8.05 (s, 1 H), 7.78 (t, J = 8.1 Hz, 1 H), 7.64-7.73 (m, 4 H), 7.37 (t, J = 8.9 Hz, 2 H) | K |
| 184 | 457 | 1.15 (d, J = 6.10 Hz, 6 H) 2.69-2.81 (m, 2 H) 3.35 (d, J = 11.60 Hz, 2 H) 3.82 (dt, J = 6.10, 4.73 Hz, 2 H) 4.42 (br. s., 2 H) 7.55 (d, J = 7.32 Hz, 1 H) 7.63 (t, J = 7.78 Hz, 1 H) 7.66-7.73 (m, 2 H) 7.90-7.97 (m, 4 H) 8.05 (s, 1 H) 8.34 (d, J = 8.24 Hz, 2 H) 10.17 (br. s., 1 H) 11.25 (br. s., 1 H) | L |
| 185 | 429 | 3.17 (br. s., 2 H) 3.30-3.40 (m, 2 H) 3.58-3.73 (m, 2 H) 3.96-4.04 (m, 2 H) 4.46 (br. s., 2 H) 7.55 (d, J = 7.63 Hz, 1 H) 7.63 (t, J = 7.63 Hz, 1 H) 7.66-7.73 (m, 2 H) 7.89-7.98 (m, 4 H) 8.05 (s, 1 H) 8.34 (d, J = 8.24 Hz, 2 H) 10.03 (br. s., 1 H) 11.26 (br. s., 1 H) | L |
| 186 | 427 | 1.38 (d, 1 H) 1.57-1.75 (m, 3 H) 1.85 (d, J = 14.65 Hz, 2 H) 2.88-2.99 (m, 2 H) 3.28-3.44 (m, 2 H) 4.38 (d, J = 4.88 Hz, 2 H) 7.54 (d, J = 7.63 Hz, 1 H) 7.62 (t, J = 7.63 Hz, 1 H) 7.66-7.73 (m, 2 H) 7.87-7.98 (m, 4 H) 8.05 (s, 1 H) 8.34 (d, J = 8.54 Hz, 2 H) 9.39 (br. s., 1 H) 11.25 (br. s., 1 H) | L |
| 187 | 415 | 1.26 (t, J = 7.32 Hz, 6 H) 3.08-3.22 (m, J = 11.18, 11.18, 7.10, 6.87 Hz, 4 H) 4.41 (d, J = 5.49 Hz, 2 H) 7.57 (d, J = 7.63 Hz, 1 H) 7.62 (t, J = 7.63 Hz, 1 H) 7.66-7.72 (m, 2 H) 7.91 (d, J = 7.93 Hz, 1 H) 7.96 (d, J = 8.24 Hz, 2 H) 7.99 (s, 1 H) 8.05 (s, 1 H) 8.34 (d, J = 8.24 Hz, 2 H) 9.41 (br. s., 1 H) 10.10 (d, J = 1.22 Hz, 1 H) 11.25 (br. s., 1 H) | L |
| 188 | 471 | 0.95 (d, J = 6.41 Hz, 6 H) 1.00 (d, J = 6.71 Hz, 6 H) 2.14 (dt, J = 13.20, 6.68 Hz, 2 H) 2.91-3.03 (m, 4 H) 4.48 (d, J = 4.27 Hz, 2 H) 7.57-7.73 (m, 4 H) 7.90-7.98 (m, 3 H) 8.04 (d, J = 6.71 Hz, 2 H) 8.34 (d, J = 8.24 Hz, 2 H) 8.76 (br. s., 1 H) 11.25 (br. s., 1 H) | L |
| 189 | 246 | 1H NMR (600 MHz, CD3OD) δ ppm 8.16 (br. s., 1 H) 7.64-7.91 (m, 2 H) | B |
| 190 | 429 | 11.24 (br. s., 1 H), 9.73 (br. s., 1 H), 8.32 (d, J = 8.2 Hz, 2 H), 8.04 (s, 4 H), 7.43-7.80 (m, 3 H), 4.35 (d, J = 5.2 Hz, 2 H), 2.78 (d, J = 4.6 Hz, 4 H) | Separate procedure |
| 191 | 431 | 11.23 (br. s., 1 H), 8.77 (br. s., 2 H), 8.31 (d, J = 8.2 Hz, 2 H), 8.04 (s, 1 H), 7.95 (d, J = 8.5 Hz, 2 H), 7.90 (d, J = 7.9 Hz, 2 H), 7.64-7.72 (m, 2 H), 7.62 (d, J = 8.2 Hz, 2 H), 4.24 (t, J = 5.8 Hz, 2 H), 3.41 (t, J = 6.0 Hz, 2 H), 3.25 (s, 3 H), 2.96-3.06 (m, 2 H), 1.84-1.94 (m, 2 H) | Separate procedure |
| 192 | 358 | NA | Separate procedure |
| 193 | 373 | 11.33 (br. s., 1 H), 11.26 (br. s., 1 H), 8.30 (d, J = 8.5 Hz, 2 H), 8.21 (s, 1 H), 8.05 (s, 1 H), 7.97 (d, J = 8.5 Hz, 2 H), 7.85 (d, J = 8.5 Hz, 2 H), 7.64-7.77 (m, 4 H) | Separate procedure |
| 194 | 359 | 11.24 (br. s., 1 H), 8.31 (d, J = 8.5 Hz, 2 H), 8.20 (br. s., 2 H), 8.04 (s, 1 H), 7.95 (d, J = 8.5 Hz, 2 H), 7.88 (d, J = 8.2 Hz, 2 H), 7.64-7.72 (m, 2 H), 7.59 (d, J = 8.2 Hz, 2 H), 4.12 (q, J = 5.8 Hz, 2 H) | Separate procedure |
| 195 | 401 | 1H NMR (600 MHz, CD3OD) δ ppm 3.06 (s, 3 H) 3.14 (s, 3 H) 7.59 (d, J = 8.24 Hz, 2 H) 7.81-7.90 (m, 3 H) 7.91 (dd, J = 8.55, 1.22 Hz, 1 H) 8.02 (d, J = 8.55 Hz, 2 H) 8.20 (s, 1 H) 8.25 (d, J = 8.54 Hz, 2 H) | Separate procedure |
| 196 | 360 | 1H NMR (600 MHz, CD3OD) δ ppm 4.68 (s, 2 H) 7.51 (d, J = 7.93 Hz, 2 H) 7.74 (d, J = 7.93 Hz, 2 H) 7.81 (d, J = 8.55 Hz, 1 H) 7.89 (d, J = 8.24 Hz, 1 H) 7.97 (d, J = 8.24 Hz, 2 H) 8.12-8.28 (m, 3 H) | Separate procedure |
| 197 | 413 | 1.81-1.94 (m, 2 H) 2.02-2.10 (m, 2 H) 3.08-3.20 (m, 2 H) 3.41 (br. s., 2 H) 4.43 (d, J = 5.80 Hz, 2 H) 7.61-7.74 (m, 3 H) 7.91 (d, J = 8.24 Hz, 1 H) 7.96 (d, J = 8.55 Hz, 2 H) 8.04 (s, 1 H) 8.31 (d, J = 8.54 Hz, 2 H) 9.81 (br. s., 1 H) 11.24 (br. s., 1 H) | Separate procedure |
| 198 | 387 | 2.78 (d, J = 4.27 Hz, 6 H) 4.35 (d, J = 5.19 Hz, 2 H) 7.63 (d, J = 8.24 Hz, 2 H) 7.66-7.73 (m, 2 H) 7.93 (d, J = 8.24 Hz, 2 H) 7.97 (d, J = 8.54 Hz, 2 H) 8.05 (s, 1 H) 8.32 (d, J = 8.54 Hz, 2 H) 9.73 (br. s., 1 H) 11.25 (br. s., 1 H | Separate procedure |

TABLE 2-continued

| EX | MS (ESI)+ m/z [M + H]+ | ¹H NMR (600 MHz, DMSO-d₆ d ppm (unless otherwise stated) | General proced. |
|---|---|---|---|
| 199 | 471 | 0.97 (d, J = 6.71 Hz, 6 H) 1.01 (d, J = 6.71 Hz, 6 H) 2.15 (dt, J = 13.20, 6.68 Hz, 2 H) 2.93 (dd, J = 11.75, 1.98 Hz, 4 H) 4.45 (d, J = 4.27 Hz, 2 H) 7.62-7.75 (m, 4 H) 7.95 (d, J = 8.24 Hz, 2 H) 7.99 (d, J = 8.24 Hz, 2 H) 8.05 (s, 1 H) 8.32 (d, J = 8.24 Hz, 2 H) 8.75 (br. s., 1 H) 11.25 (br. s., 1 H) | Separate procedure |
| 200 | 427 | 1.33-1.44 (m, 2 H) 1.67 (d, J = 3.66 Hz, 2 H) 1.84 (d, J = 14.04 Hz, 2 H) 2.87-2.99 (m, 2 H) 3.37 (d, J = 11.90 Hz, 2 H) 4.35 (d, J = 5.19 Hz, 2 H) 7.64 (d, J = 8.24 Hz, 2 H) 7.66-7.72 (m, 2 H) 7.92 (d, J = 8.24 Hz, 2 H) 7.97 (d, J = 8.55 Hz, 2 H) 8.05 (s, 1 H) 8.32 (d, J = 8.54 Hz, 2 H) 9.37 (br. s., 1 H) 11.25 (br. s., 1 H) | Separate procedure |
| 201 | 457 | ¹H NMR (600 MHz, CD₃OD) δ ppm 1.23 (d, J = 6.41 Hz, 6 H) 2.76-2.84 (m, 2 H) 3.37-3.43 (m, 2 H) 3.82-3.91 (m, 2 H) 4.41 (s, 2 H) 7.66 (d, J = 7.93 Hz, 2 H) 7.75-7.79 (m, 1 H) 7.80-7.84 (m, 1 H) 7.88 (d, J = 8.24 Hz, 2 H) 7.95 (d, J = 8.85 Hz, 2 H) 8.14 (s, 1 H) 8.24 (d, J = 8.55 Hz, 2 H) | Separate procedure |
| 202 | 360 | ¹H NMR (600 MHz, CD₃OD) δ ppm 4.71 (s, 2 H) 7.39-7.69 (m, 3 H) 7.75-7.87 (m, 2 H) 7.93 (dd, J = 7.48, 6.26 Hz, 1 H) 8.00 (d, J = 8.54 Hz, 2 H) 8.19-8.27 (m, 3 H) | Separate procedure |
| 203 | 373 | ¹H NMR (600 MHz, CD₃OD) δ ppm 7.63 (t, J = 7.93 Hz, 1 H) 7.81 (d, J = 7.93 Hz, 1 H) 7.88 (dd, J = 8.55, 1.22 Hz, 1 H) 7.94 (ddd, J = 5.57, 4.04, 1.68 Hz, 2 H) 8.02 (d, J = 8.54 Hz, 2 H) 8.18 (s, 3 H) 8.23-8.29 (m, 3 H) | Separate procedure |
| 204 | 423 | 3.05 (s, 3 H) 7.34 (d, J = 8.55 Hz, 2 H) 7.72 (d, J = 8.24 Hz, 1 H) 7.80 (d, J = 8.55 Hz, 2 H) 7.92 (d, J = 8.24 Hz, 3 H) 8.21 (s, 1 H) 8.28 (d, J = 8.55 Hz, 2 H) 9.94 (s, 1 H) | Separate procedure |
| 205 | 353 | ¹H NMR (600 MHz, CD₃OD) δ ppm 8.27 (d, J = 8.24 Hz, 2 H) 8.19 (s, 1 H) 7.81-7.90 (m, 4 H) 4.51 (s, 2 H) 3.69-4.15 (m, 4 H) 3.25-3.51 (m, 4 H) | M |
| 206 | 351 | ¹H NMR (600 MHz, CD₃OD) δ ppm 8.08 (d, J = 8.54 Hz, 2 H) 8.05 (s, 1 H) 7.62-7.70 (m, 2 H) 7.54 (d, J = 8.55 Hz, 2 H) 3.60 (s, 2 H) 2.48 (br. s., 4 H) 1.62 (quin, J = 5.65 Hz, 4 H) 1.48 (br. s., 2 H) | M |
| 207 | 366 | ¹H NMR (600 MHz, CD₃OD) δ ppm 8.08 (d, J = 8.24 Hz, 2 H) 8.05 (br. s., 1 H) 7.62-7.72 (m, 2 H) 7.54 (d, J = 8.24 Hz, 2 H) 4.58 (br. s., 5 H) 3.62 (s, 2 H) 2.53 (br. s., 6 H) 2.29 (s, 3 H) | M |
| 208 | 341 | ¹H NMR (600 MHz, CD₃OD) δ ppm 8.08-8.11 (m, 2 H) 8.03-8.07 (m, 1 H) 7.63-7.70 (m, 2 H) 7.53-7.58 (m, 2 H) 3.87-3.90 (m, 2 H) 3.54 (ddd, J = 5.34, 2.59, 2.44 Hz, 2 H) 3.35 (s, 3 H) 2.78-2.83 (m, 2 H) | M |
| 209 | 353 | ¹H NMR (600 MHz, CD₃OD) δ ppm 8.11 (s, 1 H) 8.06 (br. s., 1 H) 8.03 (ddd, J = 5.26, 3.59, 1.83 Hz, 1 H) 7.63-7.71 (m, 2 H) 7.53-7.55 (m, 2 H) 3.71 (t, J = 4.73 Hz, 4 H) 3.64 (s, 2 H) 2.52 (br. s., 4 H) | N |
| 210 | 351 | ¹H NMR (600 MHz, CD₃OD) δ ppm 8.05-8.08 (m, 2 H) 8.03 (ddd, J = 5.34, 3.51, 1.83 Hz, 1 H) 7.68 (dd, 1 H) 7.66 (d, 1 H) 7.52-7.54 (m, 2 H) 3.63 (s, 2 H) 2.50 (br. s., 4 H) 1.57-1.65 (m, 4 H) 1.47 (br. s., 2 H) | N |
| 211 | 366 | ¹H NMR (600 MHz, CD₃OD) δ ppm 8.08 (s, 1 H) 8.06 (s, 2 H) 7.68 (m, 1 H) 7.65 (m, 1 H) 7.51-7.55 (m, 2 H) 3.65 (s, 2 H) 2.54 (br. s., 8 H) 2.28 (s, 3 H) | N |
| 212 | 341 | ¹H NMR (600 MHz, CD₃OD) δ ppm 8.08 (s, 1 H) 8.06 (s, 1 H) 8.03 (dt, J = 5.42, 2.63 Hz, 1 H) 7.68-7.70 (m, 1 H) 7.65-7.67 (m, 1 H) 7.53-7.56 (m, 2 H) 3.91 (s, 2 H) 3.54 (t, J = 5.34 Hz, 2 H) 3.35 (s, 3 H) 2.82 (t, J = 5.34 Hz, 2 H) | N |
| 213 | 311 | ¹H NMR (600 MHz, CD₃OD) δ ppm 8.20 (d, J = 8.55 Hz, 1 H) 8.17 (s, 1 H) 7.95 (d, J = 8.54 Hz, 1 H) 7.88 (dd, J = 8.55, 1.22 Hz, 1 H) 7.81 (d, J = 8.55 Hz, 1 H) 7.76 (q, J = 4.78 Hz, 1 H) 7.39 (q, J = 4.68 Hz, 1 H) 4.85 (s, 6 H) 3.02 (s, 2 H) | N |
| 214 | 314 | 10.95 (br. s., 1 H), 8.10 (d, J = 8.2 Hz, 2 H), 7.71 (d, J = 6.1 Hz, 1 H), 7.36-7.53 (m, 3 H), 2.90-3.05 (m, 1 H), 1.25 (d, J = 7.0 Hz, 6 H) | O |
| 215 | 308 | 10.97 (br. s., 1 H), 8.01 (dd, J = 7.9, 6.4 Hz, 1 H), 7.79 (d, J = 6.1 Hz, 1 H), 7.64 (d, J = 8.5 Hz, 1 H), 7.52 (d, J = 10.4 Hz, 1 H), 7.37-7.47 (m, 1 H). | O |
| 216 | 320 | 10.95 (br. s., 1 H), 7.95 (dd, J = 8.4, 2.0 Hz, 1 H), 7.76 (ddd, J = 8.5, 4.3, 2.1 Hz, 2 H), 7.34-7.57 (m, 2 H), 3.97 (s, 3 H) | O |
| 217 | 348 | 10.97 (br. s., 1 H), 8.27 (d, J = 8.5 Hz, 2 H), 7.91 (d, J = 8.5 Hz, 2 H), 7.68-7.85 (m, 3 H), 7.52 (t, J = 7.8 Hz, 4 H) | O |
| 218 | 306 | 10.97 (br. s., 1 H), 8.22 (s, 1 H), 8.14 (td, J = 4.4, 1.8 Hz, 1 H), 7.74 (d, J = 5.8 Hz, 1 H), 7.57-7.69 (m, 2 H), 7.51 (d, J = 10.4 Hz, 1 H) | O |
| 219 | 350/352 | 10.95 (br. s., 1 H), 8.11 (d, J = 8.5 Hz, 2 H), 7.80 (d, J = 8.5 Hz, 2 H), 7.72 (d, J = 6.1 Hz, 1 H), 7.49 (d, 1 H) | O |
| 220 | 366 | 10.97 (br. s., 1 H), 8.28 (d, J = 8.5 Hz, 2 H), 7.71-7.87 (m, 3 H), 7.65 (td, J = 8.0, 1.7 Hz, 1 H), 7.43-7.55 (m, 2 H), 7.31-7.40 (m, 2 H) | O |

TABLE 2-continued

| EX | MS (ESI)+ m/z [M + H]+ | 1H NMR (600 MHz, DMSO-d6 d ppm (unless otherwise stated) | General proced. |
|---|---|---|---|
| 221 | 298 | 11.31 (br. s., 1 H) 8.10 (s, 1 H) 7.73-7.90 (m, 4 H) 7.20 (d, J = 8.54 Hz, 2 H) 3.94 (s, 3 H) 3.88 (s, 3 H) | P |
| 222 | 304 | 11.25 (br. s., 1 H) 8.15 (s, 1 H) 7.81 (dd, J = 8.55, 1.53 Hz, 1 H) 7.68-7.75 (m, 2 H) 7.53-7.61 (m, 1 H) 7.40-7.50 (m, 1 H) 3.78 (d, J = 1.53 Hz, 3 H) | P |
| 223 | 310 | 11.31 (br. s., 1 H) 8.12 (s, 1 H) 7.72-7.88 (m, 4 H) 7.52 (d, J = 8.24 Hz, 2 H) 3.95 (s, 3 H) 3.03 (dt, J = 13.81, 6.98 Hz, 1 H) 1.28 (d, J = 7.02 Hz, 6 H) | P |
| 224 | 316 | 11.26 (br. s., 1 H) 8.12 (s, 1 H) 7.78-7.84 (m, 1 H) 7.73-7.78 (m, 1 H) 7.60-7.66 (m, 1 H) 7.42-7.50 (m, 2 H) 3.95 (s, 3 H) 3.93 (s, 3 H) | P |
| 225 | 344 | 11.26 (br. s., 1 H) 8.13 (s, 1 H) 7.95-8.02 (m, 2 H) 7.88-7.94 (m, 2 H) 7.77-7.82 (m, 3 H) 7.71-7.77 (m, 1 H) 7.50-7.56 (m, 2 H) 7.41-7.47 (m, 1 H) 3.98 (s, 3 H) | P |
| 226 | 302 | 11.26 (br. s., 1 H) 8.13 (d, J = 0.92 Hz, 1 H) 7.94 (t, J = 1.83 Hz, 1 H) 7.86 (dt, J = 7.55, 1.41 Hz, 1 H) 7.78-7.82 (m, 1 H) 7.73-7.77 (m, 1 H) 7.67-7.70 (m, 1 H) 7.64 (t, J = 7.78 Hz, 1 H) 3.93 (s, 3 H) | P |
| 227 | 282 | 8.14 (s, 1 H) 7.68-7.91 (m, 2 H) 7.37-7.60 (m, 4 H) 3.69 (s, 3 H) 2.23 (s, 3 H) | P |
| 228 | 326 | 8.10 (s, 1 H) 7.79-7.90 (m, 2 H) 7.60 (s, 2 H) 3.95 (s, 3 H) 3.76 (s, 3 H) 2.35 (s, 6 H) | P |
| 229 | 334 | 8.20 (s, 1 H) 8.12 (d, J = 9.16 Hz, 1 H) 7.97 (d, J = 8.24 Hz, 1 H) 7.92 (br. s., 2 H) 7.33-7.52 (m, 4 H) 3.72 (br. s., 3 H) | P |
| 230 | 318 | 8.13 (s, 1 H) 7.83-7.94 (m, 1 H) 7.77-7.84 (m, 1 H) 7.61 (d, J = 2.75 Hz, 1 H) 7.53 (dd, J = 8.85, 2.75 Hz, 1 H) 7.11 (d, J = 8.85 Hz, 1 H) 3.81 (s, 3 H) | P |
| 231 | 346 | 8.98 (s, 1 H) 8.09-8.22 (m, 4 H) 7.76-7.86 (m, 1 H) 7.67-7.77 (m, 1 H) 3.95 (s, 3 H) 3.33 (s, 3 H) | P |
| 232 | 390 | 11.27 (br. s., 1 H) 8.83 (s, 2 H) 8.29 (s, 1 H) 8.08 (s, 1 H) 7.73 (s, 2 H) | Separate procedure |
| 233 | 274 | 11.36 (br. s., 1 H) 8.05 (s, 1 H) 7.82 (dd, J = 8.5, 1.2 Hz, 1 H) 7.74 (d, J = 8.5 Hz, 1 H) 2.93 (d, J = 7.3 Hz, 2 H) 1.89 (dd, J = 7.0, 3.7 Hz, 1 H) 1.51-1.75 (m, 5 H) 0.86-1.36 (m, 5 H) | Q |
| 234 | 286 | 1H NMR (600 MHz, CD3OD) δ ppm 8.11 (s, 1 H) 7.88 (dd, J = 8.5, 1.5 Hz, 1 H) 7.75 (d, J = 8.5 Hz, 1 H) 7.39-7.57 (m, 2 H) 7.14-7.34 (m, 2 H) 4.57 (s, 2 H) | Q |
| 235 | 336 | 11.27 (br. s., 1 H) 8.00 (s, 1 H) 7.80 (s, 1 H) 7.54-7.75 (m, 5 H) 4.48 (s, 2 H) | Q |
| 236 | 376 | 11.30 (br. s., 1 H) 8.02 (s, 1 H) 7.14-7.85 (m, 10 H) 4.69 (d, J = 7.0 Hz, 1 H) 1.81 (d, J = 7.3 Hz, 3 H) | Q |
| 237 | 362 | 11.31 (br. s., 1 H) 8.01 (s, 1 H) 7.81 (d, J = 8.9 Hz, 5 H) 7.46 (dd, J = 8.5, 1.5 Hz, 1 H) 7.31 (d, J = 2.7 Hz, 1 H) 7.17 (dd, J = 9.2, 2.4 Hz, 1 H) 4.75 (d, J = 7.0 Hz, 1 H) 3.86 (s, 3 H) 1.85 (d, J = 7.3 Hz, 3 H) | Q |
| 238 | 332/334 | 1H NMR (600 MHz, CD3OD) δ ppm 8.33 (t, J = 1.68 Hz, 1 H) 8.00-8.16 (m, 2 H) 7.60-7.76 (m, 3 H) 7.50 (t, J = 7.93 Hz, 1 H) | A |

Biological Tests
Method for Measurement of Enzymatic Activity of HDACs
Materials & Methods All Examples were tested in HDAC1, 2, 3, 6 and 8 in vitro enzymatic assays. The assay principle is well known (Hauser et al. 2009, Bradner et al. 2010) and all necessary reagents like enzymes, substrates, developer and reference compounds are commercially available (see e.g. BPS Biosciences http://www.bpsbioscience.com/). A series of dilutions of the compounds were prepared with a top concentration of 200 µM (2 µM for HDAC6). The enzymatic reactions were conducted in a mixture containing assay buffer, bovine serum albumin, HDAC substrate, and a test compound. After enzymatic reaction, developer was added and after an additional incubation time, fluorescence intensity was measured at an excitation wavelength of 360 nm and an emission wavelength of 460 nm. A selection of the Examples were tested in a full HDAC panel containing HDAC1, 2, 3, 4, 5, 6, 7, 8, 9, 10 and 11 in vitro enzymatic assays. The tests were performed as above except that a series of dilutions of the compounds were prepared with a top concentration of 10 µM for all HDACs.

Results

IC50 values for HDAC6 inhibition of some compounds of the invention are shown in Table 3.

TABLE 3

IC$_{50}$ values for inhibition of HDAC6 for 40 Examples of the invention.

| Example | IC50 (nM) |
|---|---|
| 3 | 45 |
| 6 | 15 |
| 11 | 110 |
| 15 | 69 |
| 18 | 77 |
| 21 | 12 |
| 50 | 14 |
| 66 | 14 |
| 80 | 19 |
| 85 | 13 |
| 96 | 5.2 |
| 97 | 12 |
| 98 | 7.0 |
| 99 | 2.0 |

TABLE 3-continued

IC$_{50}$ values for inhibition of HDAC6 for 40 Examples of the invention.

| Example | IC50 (nM) |
|---|---|
| 109 | 46 |
| 112 | 15 |
| 113 | 6.6 |
| 119 | 14 |
| 125 | 14 |
| 134 | 18 |
| 159 | 19 |
| 162 | 31 |
| 167 | 19 |
| 174 | 4.7 |
| 176 | 2.9 |
| 177 | 5.1 |
| 179 | 3.1 |
| 180 | 19 |
| 186 | 4.1 |
| 190 | 21 |
| 191 | 18 |
| 193 | 11 |
| 195 | 24 |
| 197 | 3.6 |
| 201 | 13 |
| 204 | 7.2 |
| 207 | 7.0 |
| 223 | 28 |
| 225 | 3.6 |
| 228 | 3.5 |

Examples included herein show selectivity for HDAC6 over other isoenzymes in the HDAC family, as is exemplified in Table 4 and Table 5.

TABLE 4

Selectivity profiling against selected HDAC isoforms for 14 Examples of the invention.

| Example | IC50 (nM) HDAC1 | IC50 (nM) HDAC2 | IC50 (nM) HDAC3 | IC50 (nM) HDAC6 | IC50 (nM) HDAC8 |
|---|---|---|---|---|---|
| 6 | 51000 | 160000 | 2100 | 15 | 470 |
| 21 | 1500 | 9300 | 780 | 12 | 62 |
| 50 | 3300 | 32000 | 3400 | 14 | 420 |
| 96 | 5000 | 58000 | 1300 | 5.2 | 220 |
| 97 | 5700 | 33000 | 2400 | 12 | 260 |
| 98 | 4400 | 24000 | 1900 | 7.0 | 290 |
| 109 | 6500 | 165000 | 2200 | 46 | 1200 |
| 119 | 4000 | 29000 | 2800 | 14 | 710 |
| 162 | 7700 | 94000 | 11000 | 31 | 190 |
| 190 | 4000 | 13000 | 910 | 21 | 80 |
| 207 | 700 | 7800 | 250 | 7.0 | 1800 |
| 223 | 1600 | 60000 | 4500 | 28 | 84 |
| 225 | 326 | >200000 | >200000 | 3.6 | 74 |
| 228 | 2000 | 20000 | 216 | 3.5 | 100 |

TABLE 5

Full selectivity profiling against HDAC isoforms for two Examples of the invention.

| HDAC# | IC$_{50}$ (µM)/ Example 15 | IC$_{50}$ (µM)/ Example 18 |
|---|---|---|
| HDAC 1 | >10 | >10 |
| HDAC2 | >10 | >10 |
| HDAC3 | 8.2 | 3.0 |
| HDAC4 | >10 | >10 |
| HDAC5 | >10 | >10 |
| HDAC6 | 0.069 | 0.077 |
| HDAC7 | 3.0 | 9.2 |
| HDAC8 | >10 | >10 |
| HDAC9 | 6.9 | >10 |
| HDAC10 | >10 | 8.6 |
| HDAC11 | >10 | >10 |

Method for Measurement of Cell Viability

The CellTiter-Blue® Cell Viability Assay (Promega) provides a homogeneous, fluorometric method for estimating the number of viable cells present in multi-well plates. The assay uses the indicator dye resazurin to measure the metabolic capacity of cells. Viable cells retain the ability to reduce resazurin into resorufin, which is highly fluorescent. Nonviable cells rapidly lose metabolic capacity and do not reduce the indicator dye, and thus do not generate a fluorescent signal.

Materials & Methods

Stock solutions (10 mM in DMSO) of compounds were serially diluted 1:2 in 11 concentrations. 50 nL/well (10 mM compound stock in DMSO) was acoustically dispensed in 384-well assay plates with an acoustic dispenser (EDC Biosystems ATS-100AV). Final starting concentration in the assay was 20 µM (0.2% DMSO) for test compounds. The following cell-lines (and origin) have been used: hepG2 (liver carcinoma), PaCa2 (pancreatic), U2-OS (osteosarcoma), RPMI 8226 (multiple myelom), KMS512 PE (multiple myelom), LP-1 (multiple myelom), OPM-2 (multiple myelom), U266 (multiple myelom), L363 (plasmacell), AMO-1 (plasmacytom), PBMC (peripheral blood mononuclear cells from healthy donors). Cells were seeded in assay plates (384-well black/clear, Greiner #781091) pre-dispensed with compounds, 25 µL/well, and cultured for 72 hours. After 72 hours, Celltiter Blue reagent (Promega #G8081) was diluted 1:10 with PBS and then added to wells (5 µL/well). The plates were incubated for 2 hours following addition of reagent. The plates were read in an EnVision fluorescence reader (PerkinElmer) with Ex544 nm/Em590 nm. Results were calculated as % cell viability compared to background (cells treated with 0.2% DMSO).

Results

Cell viability IC50 values of some compounds of the invention for a selection of tumor cell lines and healthy PBMCs are shown in Table 6.

TABLE 6

IC$_{50}$ values for 17 Examples of the invention based on cell viability in different cells after 72 hours of treatment with compounds of the invention

| Example | IC50 (µM) U266 | IC50 (µM) AMO-1 | IC50 (µM) PaCa2 | IC50 (µM) healthy PBMC |
|---|---|---|---|---|
| 3 | 2.9 | 6.3 | 6.0 | >20 |
| 6 | 0.54 | 1.7 | 0.41 | >20 |
| 8 | 2.0 | 2.3 | 1.7 | >20 |
| 10 | 2.1 | 2.2 | 1.2 | >20 |
| 21 | 7.8 | 7.0 | 4.3 | >20 |
| 34 | 3.9 | 10 | 12 | >20 |
| 50 | 0.58 | 2.0 | 0.29 | >20 |
| 151 | 0.49 | 1.9 | 1.0 | >20 |
| 159 | 1.2 | 6.3 | 2.1 | >20 |
| 161 | 0.64 | 5.5 | 0.61 | >20 |
| 162 | 0.74 | 3.7 | 0.82 | >20 |
| 167 | 0.16 | 0.14 | ND | >20 |
| 177 | 0.62 | 3.5 | 1.1 | >20 |

TABLE 6-continued

IC$_{50}$ values for 17 Examples of the invention based on cell viability in different cells after 72 hours of treatment with compounds of the invention

| Example | IC50 (µM) U266 | IC50 (µM) AMO-1 | IC50 (µM) PaCa2 | IC50 (µM) healthy PBMC |
|---|---|---|---|---|
| 180 | 0.56 | 0.42 | ND | >20 |
| 190 | 3.9 | 8.1 | 2.3 | >20 |
| 223 | 8.2 | 18 | 5.4 | >20 |
| 225 | 0.34 | >20 | 1.0 | >20 |

REFERENCES

Aldana-Masangkay G I, Sakamoto K M. The role of HDAC6 in cancer. J Biomed Biotechnol 2011, doi: 10.1155/2011/875824

Balasubramanian S, Ramos J, Luo W, Sirisawad M, Verner E, Buggy J J. A novel histone deacetylase 8 (HDAC8)-specific inhibitor PCI-34051 induces apoptosis in T-cell lymphomas. Leukemia. 2008; 22:1026-1034.

Balasubramanian, S.; Verner, E. V.; Buggy, J. J. Isoform-specific histone deacetylase inhibitors: the next step? Cancer Lett. 2009, 280, 211

Bazzaro M, Lin Z, Santillan A et al., "Ubiquitin proteasome system stress underlies synergistic killing of ovarian cancer cells by bortezomib and a novel HDAC6 inhibitor," Clinical Cancer Research, 2008, vol. 14, no. 22, pp. 7340-7347.

Best, J. D.; Carey, N. Epigenetic therapies for non-oncology indications. Drug Discovery Today 2010, 15, 1008-1014.

Bradner J E, West N, Grachan M L, Greenberg E F, Haggarty S J, Warnow T et al. Chemical phylogenetics of histone deacetylases. Nat Chem Biol 2010, 6, 238-243.

Brana I, Tabemo J. Cardiotoxicity, Annals of Oncology 2010, 21, Supplement 7: vii173-vii179.

Chen, Y.; He, R.; D'Annibale, M. A.; Langley, B.; Kozikowski, A. P. Studies of benzamide- and thiol-based histone deacetylase inhibitorsin models of oxidative-stress-induced neuronal death: identification of some HDAC3-selective inhibitors. Chem Med Chem 2009, 4, 842-852.

Choudhary C, Kumar C, Gnad F, Nielsen M L, Rehman M, Walther T C et al. Lysine acetylation targets protein complexes and co-regulates major cellular functions. Science 2009, 325, 834-840.

Cook C, Gendron T F, Scheffel K, Carlomagno Y, Dunmore J, DeTure M, Petrucelli L. Loss of HDAC6, a novel CHIP substrate, alleviates abnormal tau accumulation. Hum Mol Genet 2012, 21, 2936-2945.

Cook C, Petrucelli L. 2013. Tau triage decisions mediated by the chaperone network. J Alzheimers Dis 33 Suppl 1:S145-S151.

de Zoeten, E. F.; Wang, L.; Butler, K.; Beier, U. H.; Akimova, T.; Sai, H.; Bradner, J. E.; Mazitschek, R.; Kozikowski, A. P.; Matthias, P.; Hancock, W. W. Histone deacetylase 6 and heat shock protein 90 control the functions of Foxp3(+) T-regulatory cells. Mol. Cell. Biol. 2011, 31, 2066-2078

D'Ydewalle C, Krishnan J, Chiheb D M, Van Damme P, Irobi J, Kozikowski A P, Vanden Berghe P, Timmerman V, Robberecht W, Van Den Bosch L: HDAC6 inhibitors reverse axonal loss in a mouse model of mutant HSPB1-induced Charcot-Marie-Tooth disease. Nat Med 2011, 17:968-974.

Espallergues J, Teegarden S L, Veerakumar A, Boulden J, Challis C, Jochems J, Chan M, Petersen T, Deneris E, Matthias P, Hahn C G, Lucki I, Beck S G, Berton O. HDAC6 regulates glucocorticoid receptor signaling in serotonin pathways with critical impact on stress resilience. J Neurosci 2012, 32, 4400-4416.

Fukada M, Hanai A, Nakayama A, Suzuki T, Miyata N, Rodriguiz R M, Wetsel W C, Yao T P, Kawaguchi Y. Loss of deacetylation activity of HDAC6 affects emotional behavior in mice. PLoS ONE 2012, 7, e30924.

George, P., Bali, P., Annavarapu, S., Scuto, A., Fiskus, W., Guo, F., Sigua, C., Sondarva, G., Moscinski, L., Atadja, P. et al. Combination of the histone deacetylase inhibitor LBH589 and the hsp90 inhibitor 17-AAG is highly active against human CML-BC cells and AML cells with activating mutation of FLT-3. Blood, 2005, 105, 1768-1776.

Govindarajan N, Rao P, Burkhardt S, Sananbenesi F, Schliiter O M, Bradke F, Lu J, Fischer A: Reducing HDAC6 ameliorates cognitive deficits in a mouse model for Alzheimer's disease. EMBO Mol Med 2013, 5:52-63.

Greer J. M.; McCombe, P. A. The role of epigenetic mechanisms and processes in autoimmune disorders. Biologics 2012, 6, 307-327.

Gregoretti, I. V., Lee, Y. M. & Goodson, H. V. Molecular evolution of the histone deacetylase family: functional implications of phylogenetic analysis. J. Mol. Biol. 2004, 338, 17-31.

Hauser A T, Jung M, Jung M. Assays for histone deacetylases. Curr Top Med Chem 2009, 9, 227-234.

Hideshima, T.; Bradner, J. E.; Wong J. et al., Small-molecule inhibition of proteasome and aggresome function induces synergistic antitumor activity in multiple myeloma, Proc. Natl. Acad. Sci. U.S.A., 2005, 102, 8567-8572.

Jochems J, Boulden J, Lee B G, Blendy J A, Jarpe M, Mazitschek R, Van Duzer J H, Jones S and Berton O. Antidepressant-Like Properties of Novel HDAC6-Selective Inhibitors with Improved Brain Bioavailability. Neuropsychopharmacology 2014, 39, 389-400.

Kalin J H, Bergman J A. Development and therapeutic implications of selective histone deacetylase 6 inhibitors. J Med Chem 2013, 56, 6297-6313.

Karberg, S. Switching on epigenetic therapy. Cell 2009, 139, 1029-1031.

Kawaguchi Y. Loss of deacetylation activity of Hdac6 affects emotional behavior in mice. PloSone 2012, 7, e30924.

Kim, C.; Choi, H.; Jung, E. S.; Lee, W.; Oh, S.; Jeon, N. L.; Mook-Jung, I. HDAC6 inhibitor blocks amyloid beta-induced impairment of mitochondrial transport in hippocampal neurons. PLoS One 2012, 7, e42983.

Kim, D.; Frank, C. L.; Dobbin, M. M.; Tsunemoto, R. K.; Tu, W.; Peng, P. L.; Guan, J. S.; Lee, B. H.; Moy, L. Y.; Giusti, P.; Broodie, N.; Mazitschek, R.; Delalle, I.; Haggarty, S. J.; Neve, R. L.; Lu, Y.; Tsai, L. H. Deregulation of HDAC1 by p25/Cdk5 in neurotoxicity. Neuron 2008, 60, 803-817.

Kouzarides, T. Chromatin modifications and their function. Cell 2007, 128, 693-705.

Lee J. K.; Zheng B. Role of myelin-associated inhibitors in axonal repair after spinal cord injury. Exp Neurol 2012, 235:33-42.

Lee, Y. S.; Lim, K. H.; Guo, X.; Kawaguchi, Y.; Gao, Y.; Barrientos, T.; Ordentlich, P.; Wang, X. F.; Counter, C. M.; Yao, T. P. The cytoplasmic deacetylase HDAC6 is required for efficient oncogenic tumorigenesis. Cancer Res. 2008, 68, 7561-7569.

The invention claimed is:
1. A compound of formula (Ia)

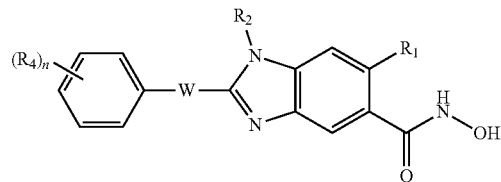

or a pharmaceutically acceptable salt thereof; wherein
$R_1$ is H;
$R_2$ is H;
n is an integer of from 1 to 3;
each $R_4$ is independently selected from halogen, C1-C10 alkyl, $R_5O$, $R_6C(O)$, $R_7R_8NX_1$, $R_9C(O)N(R_{10})$, $R_{11}S(O)_2$, $NO_2$, COOH, CN, and phenyl, said phenyl optionally being substituted with one or more $R_{12}$; and when n is at least 2, two $R_4$ attached to adjacent atoms of ring A may form together a biradical selected from —$Y_1CH_2Y_2$— and —$Y_1(CH_2)_2Y_2$—; wherein $Y_1$ and $Y_2$ are independently selected from O and $CH_2$;
$R_5$ is selected from H, C1-C6 alkyl, $R_{13}O(CH_2)_2$, $R_{14}R_{15}NX_2CH_2$, and phenyl, said phenyl optionally being substituted with one or more $R_{16}$;
$R_6$ is selected from H, C1-C6 alkyl, and phenyl, said phenyl optionally being substituted with one or more $R_{17}$;
$R_7$ and $R_8$ are independently selected from H and C1-C6 alkyl optionally substituted by $R_{18}O$; or
$R_7$ and $R_8$ form, together with the nitrogen to which they are both attached, a 5- or 6-membered heterocyclyl selected from piperidinyl, piperazinyl and morpholinyl said heterocyclyl optionally being substituted by one or more C1-C3 alkyl;
$R_9$, $R_{10}$ and $R_{11}$ are independently selected from H and C1-C6 alkyl;
each $R_{12}$ is independently selected from halogen, C1-C6 alkyl, $R_{19}OX_3$, $R_{20}S(O)_2$, $R_{21}R_{22}NX_4$, $R_{23}C(O)$, $R_{24}C(NOH)$, and $R_{25}S(O)_2N(R_{26})$;
$R_{13}$ is selected from H, phenyl, and C1-C6 alkyl, said alkyl optionally being substituted by $R_{27}O$;
$R_{14}$ and $R_{15}$ are independently selected from H and C1-C6 alkyl optionally substituted by $R_{28}O$;
or $R_{14}$ and $R_{15}$ form, together with the nitrogen to which they are both attached, a 5- or 6-membered heterocyclyl selected from pyrrolidinyl, piperidinyl, piperazinyl and morpholinyl, said heterocyclyl optionally being substituted by one or more C1-C3 alkyl;
each $R_{16}$ is independently selected from halogen, C1-C6 alkyl, and $R_{29}O$;
$R_{17}$ is selected from halogen, C1-C6 alkyl, and $R_{30}O$;
$R_{18}$, $R_{19}$ and $R_{20}$ are independently selected from H and C1-C6 alkyl;
$R_{21}$ and $R_{22}$ are independently selected from H and C1-C6 alkyl optionally substituted by $R_{31}O$;
or $R_{21}$ and $R_{22}$ form, together with the nitrogen to which they are both attached, a 5- or 6-membered heterocyclyl selected from pyrrolidinyl, piperidinyl, piperazinyl and morpholinyl, said heterocyclyl optionally being substituted by one or more C1-C3 alkyl;
$R_{23}$, $R_{24}$, $R_{25}$, $R_{26}$, $R_{27}$, $R_{28}$, $R_{29}$, $R_{30}$ and $R_{31}$ are independently selected from H and C1-C6 alkyl;

$X_1$, $X_2$, and $X_4$ are independently selected from a direct bond, $CH_2$ and $C(O)$;

$X_3$ is a direct bond or $CH_2$;

W is a direct bond, and any alkyl is optionally substituted with one or more F.

2. The compound of claim 1, wherein each $R_4$ is independently selected from halogen, C1-C10 alkyl, $R_5O$, $R_7R_8NX_1$, CN, and phenyl, and when n is at least 2, two $R_4$ attached to adjacent atoms of ring A may form together a biradical selected from —$Y_1CH_2Y_2$— and —$Y_1(CH_2)_2Y_2$—; wherein $Y_1$ and $Y_2$ are independently selected from O and $CH_2$.

3. The compound of claim 2, wherein each $R_4$ is independently selected from halogen, C1-C10 alkyl, $R_5O$, and phenyl, said phenyl optionally being substituted with one or more $R_{12}$.

4. The compound claim 1, wherein one $R_4$ is phenyl, said phenyl optionally being substituted with one or more $R_{12}$.

5. The compound of claim 1, of formula (Iac)

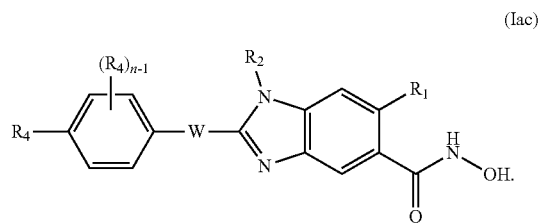

(Iac)

6. A compound according to claim 1, selected from 2-(3-chlorophenyl)-N-hydroxy-1H-benzimidazole-6-carboxamide,
N-hydroxy-2-(2-methoxyphenyl)-1H-benzimidazole-6-carboxamide,
2-(4-bromophenyl)-N-hydroxy-1H-benzimidazole-6-carboxamide,
N-hydroxy-2-(4-methylphenyl)-1H-benzimidazole-6-carboxamide,
N-hydroxy-2-[4-(trifluoromethyl)phenyl]-1H-benzimidazole-6-carboxamide,
2-biphenyl-4-yl-N-hydroxy-1H-benzimidazole-6-carboxamide,
N-hydroxy-2-(4-phenoxyphenyl)-1H-benzimidazole-6-carboxamide,
2-(2,3-dihydro-1,4-benzodioxin-6-yl)-N-hydroxy-1H-benzimidazole-6-carboxamide,
2-[4-(difluoromethoxy)phenyl]-N-hydroxy-1H-benzimidazole-6-carboxamide,
2-(4-fluoro-3-methoxyphenyl)-N-hydroxy-1H-benzimidazole-6-carboxamide,
N-hydroxy-2-(4-hydroxy-3-methoxyphenyl)-1H-benzimidazole-6-carboxamide,
N-hydroxy-2-(4-hydroxy-2,6-dimethylphenyl)-1H-benzimidazole-6-carboxamide,
2-(4-fluorophenyl)-N-hydroxy-1H-benzimidazole-6-carboxamide,
2-(2-chlorophenyl)-N-hydroxy-1H-benzimidazole-6-carboxamide,
N-hydroxy-2-[2-(trifluoromethyl)phenyl]-1H-benzimidazole-6-carboxamide,
N-hydroxy-2-(4-methoxyphenyl)-1H-benzimidazole-6-carboxamide,
2-[4-(acetylamino)phenyl]-N-hydroxy-1H-benzimidazole-6-carboxamide,
2-(3-bromophenyl)-N-hydroxy-1H-benzimidazole-6-carboxamide,
N-hydroxy-2-(4-methoxy-3-methylphenyl)-1H-benzimidazole-6-carboxamide,
2-(4-chlorophenyl)-N-hydroxy-1H-benzimidazole-6-carboxamide,
N-hydroxy-2-(3-methoxy-2-nitrophenyl)-1H-benzimidazole-6-carboxamide,
2-(3,4-difluorophenyl)-N-hydroxy-1H-benzimidazole-6-carboxamide,
2-(3-fluoro-2-methylphenyl)-N-hydroxy-1H-benzimidazole-6-carboxamide,
N-hydroxy-2-(3-phenoxyphenyl)-1H-benzimidazole-6-carboxamide,
2-[3-fluoro-5-(trifluoromethyl)phenyl]-N-hydroxy-1H-benzimidazole-6-carboxamide,
N-hydroxy-2-(4-nitrophenyl)-1H-benzimidazole-6-carboxamide,
2-(5-chloro-2-nitrophenyl)-N-hydroxy-1H-benzimidazole-6-carboxamide,
2-(4-chloro-3-nitrophenyl)-N-hydroxy-1H-benzimidazole-6-carboxamide,
2-[4-(diethylamino)phenyl]-N-hydroxy-1H-benzimidazole-6-carboxamide,
2-[2-chloro-3-(trifluoromethyl)phenyl]-N-hydroxy-1H-benzimidazole-6-carboxamide,
2-(2,3-difluorophenyl)-N-hydroxy-1H-benzimidazole-6-carboxamide,
2-[2-fluoro-4-(trifluoromethyl)phenyl]-N-hydroxy-1H-benzimidazole-6-carboxamide,
2-(2,4-dichlorophenyl)-N-hydroxy-1H-benzimidazole-6-carboxamide,
N-hydroxy-2-[3-(trifluoromethyl)phenyl]-1H-benzimidazole-6-carboxamide,
N-hydroxy-2-(3-methoxyphenyl)-1H-benzimidazole-6-carboxamide,
2-(3,4-dichlorophenyl)-N-hydroxy-1H-benzimidazole-6-carboxamide,
N-hydroxy-2-(3-methylphenyl)-1H-benzimidazole-6-carboxamide,
2-(2,4-dimethoxyphenyl)-N-hydroxy-1H-benzimidazole-6-carboxamide,
N-hydroxy-2-(3-nitrophenyl)-1H-benzimidazole-6-carboxamide,
2-(3-cyanophenyl)-N-hydroxy-1H-benzimidazole-6-carboxamide,
2-(2,5-dimethoxyphenyl)-N-hydroxy-1H-benzimidazole-6-carboxamide,
2-(3,4-dimethoxyphenyl)-N-hydroxy-1H-benzimidazole-6-carboxamide,
2-(2-fluoro-5-nitrophenyl)-N-hydroxy-1H-benzimidazole-6-carboxamide,
N-hydroxy-2-[4-(1-methylethyl)phenyl]-1H-benzimidazole-6-carboxamide,
2-(2-chloro-5-nitrophenyl)-N-hydroxy-1H-benzimidazole-6-carboxamide,
2-(3,5-dimethoxyphenyl)-N-hydroxy-1H-benzimidazole-6-carboxamide,
2-(1,3-benzodioxol-5-yl)-N-hydroxy-1H-benzimidazole-6-carboxamide,
2-(5-tert-butyl-2-hydroxyphenyl)-N-hydroxy-1H-benzimidazole-6-carboxamide,
2-[3-(4-tert-butylphenoxy)phenyl]-N-hydroxy-1H-benzimidazole-6-carboxamide,
N-hydroxy-2-(2-methylbiphenyl-3-yl)-1H-benzimidazole-6-carboxamide, N-hydroxy-2-(4-hydroxyphenyl)-1H-benzimidazole-6-carboxamide,
N-hydroxy-2-(2-hydroxy-3-methoxyphenyl)-1H-benzimidazole-6-carboxamide,
2-(4-ethoxyphenyl)-N-hydroxy-1H-benzimidazole-6-carboxamide,
N-hydroxy-2-(4-hydroxy-2-methoxyphenyl)-1H-benzimidazole-6-carboxamide,
N-hydroxy-2-(4-hydroxy-2-methylphenyl)-1H-benzimidazole-6-carboxamide,
2-(3-fluoro-2-hydroxyphenyl)-N-hydroxy-1H-benzimidazole-6-carboxamide,
N-hydroxy-2-(3-hydroxyphenyl)-1H-benzimidazole-6-carboxamide,
N-hydroxy-2-(4-hydroxy-3-methoxyphenyl)-1H-benzimidazole-6-carboxamide,
N-hydroxy-2-(2-hydroxyphenyl)-1H-benzimidazole-6-carboxamide,
N-hydroxy-2-(2-methylphenyl)-1H-benzimidazole-6-carboxamide,
2-(2,3-dihydro-1-benzofuran-5-yl)-N-hydroxy-1H-benzimidazole-6-carboxamide,
N-hydroxy-2-[4-(1-methylethoxy)phenyl]-1H-benzimidazole-6-carboxamide,
2-(5-chloro-2-hydroxyphenyl)-N-hydroxy-1H-benzimidazole-6-carboxamide,
N-hydroxy-2-(4-hydroxy-2,6-dimethylphenyl)-1H-benzimidazole-6-carboxamide,
2-(4-fluoro-3-methylphenyl)-N-hydroxy-1H-benzimidazole-6-carboxamide,
2-(2,5-dimethylphenyl)-N-hydroxy-1H-benzimidazole-6-carboxamide,
2-(2,4-dimethylphenyl)-N-hydroxy-1H-benzimidazole-6-carboxamide,
2-(3,4-dimethylphenyl)-N-hydroxy-1H-benzimidazole-6-carboxamide,
2-(3-fluoro-4-methylphenyl)-N-hydroxy-1H-benzimidazole-6-carboxamide,
2-(2,3-dimethylphenyl)-N-hydroxy-1H-benzimidazole-6-carboxamide,
2-(4-ethylphenyl)-N-hydroxy-1H-benzimidazole-6-carboxamide,
2-(2-ethylphenyl)-N-hydroxy-1H-benzimidazole-6-carboxamide,
N-hydroxy-2-(4-pentylphenyl)-1H-benzimidazole-6-carboxamide,
N-hydroxy-2-[3-(4-methoxyphenoxy)phenyl]-1H-benzimidazole-6-carboxamide,
N-hydroxy-2-(3'-methoxybiphenyl-4-yl)-1H-benzimidazole-6-carboxamide,
2-(3,5-di-tert-butyl-4-hydroxyphenyl)-N-hydroxy-1H-benzimidazole-6-carboxamide,
2-(4-bromo-3-fluorophenyl)-N-hydroxy-1H-benzimidazole-6-carboxamide,
2-(4-chloro-3-fluorophenyl)-N-hydroxy-1H-benzimidazole-6-carboxamide,
2-(3-fluorophenyl)-N-hydroxy-1H-benzimidazole-6-carboxamide,
2-biphenyl-2-yl-N-hydroxy-1H-benzimidazole-6-carboxamide,
2-(2-fluorophenyl)-N-hydroxy-1H-benzimidazole-6-carboxamide,
N-hydroxy-2-(4-propoxyphenyl)-1H-benzimidazole-6-carboxamide,
N-hydroxy-2-[4-(2-methylpropoxy)phenyl]-1H-benzimidazole-6-carboxamide,
N-hydroxy-2-{4-[2-(2-methoxyethoxy)ethoxy]phenyl}-1H-benzimidazole-6-carboxamide,
N-hydroxy-2-[4-(2-morpholin-4-ylethoxy)phenyl]-1H-benzimidazole-6-carboxamide,
2-{4-[2-(diethylamino)ethoxy]phenyl}-N-hydroxy-1H-benzimidazole-6-carboxamide,
2-[4-(2-ethoxyethoxy)phenyl]-N-hydroxy-1H-benzimidazole-6-carboxamide,
N-hydroxy-2-[4-(2-phenoxyethoxy)phenyl]-1H-benzimidazole-6-carboxamide,
N-hydroxy-2-(3-propoxyphenyl)-1H-benzimidazole-6-carboxamide,
N-hydroxy-2-[3-(2-methylpropoxy)phenyl]-1H-benzimidazole-6-carboxamide,
N-hydroxy-2-{3-[2-(2-methoxyethoxy)ethoxy]phenyl}-1H-benzimidazole-6-carboxamide,
N-hydroxy-2-[3-(2-morpholin-4-ylethoxy)phenyl]-1H-benzimidazole-6-carboxamide,
2-{3-[2-(diethylamino)ethoxy]phenyl}-N-hydroxy-1H-benzimidazole-6-carboxamide,
2-[3-(2-ethoxyethoxy)phenyl]-N-hydroxy-1H-benzimidazole-6-carboxamide,
N-hydroxy-2-[3-(2-phenoxyethoxy)phenyl]-1H-benzimidazole-6-carboxamide,
N-hydroxy-2-[3-(2-morpholin-4-yl-2-oxoethoxy)phenyl]-1H-benzimidazole-6-carboxamide,
N-hydroxy-2-[3-(2-hydroxyethoxy)phenyl]-1H-benzimidazole-6-carboxamide,
N-hydroxy-2-(2-propoxyphenyl)-1H-benzimidazole-6-carboxamide,
N-hydroxy-2-[2-(2-methylpropoxy)phenyl]-1H-benzimidazole-6-carboxamide,
N-hydroxy-2-{2-[2-(2-methoxyethoxy)ethoxy]phenyl}1-1H-benzimidazole-6-carboxamide,
N-hydroxy-2-[2-(2-morpholin-4-ylethoxy)phenyl]-1H-benzimidazole-6-carboxamide,
2-{2-[2-(diethylamino)ethoxy]phenyl}-N-hydroxy-1H-benzimidazole-6-carboxamide,
2-[2-(2-ethoxyethoxy)phenyl]-N-hydroxy-1H-benzimidazole-6-carboxamide,
N-hydroxy-2-[2-(2-phenoxyethoxy)phenyl]-1H-benzimidazole-6-carboxamide,
N-hydroxy-2-[2-(2-morpholin-4-yl-2-oxoethoxy)phenyl]-1H-benzimidazole-6-carboxamide,
N-hydroxy-2-(4'-methoxybiphenyl-3-yl)-1H-benzimidazole-6-carboxamide,
2-(3'-chlorobiphenyl-3-yl)-N-hydroxy-1H-benzimidazole-6-carboxamide,
N-hydroxy-2-(4'-methoxybiphenyl-4-yl)-1H-benzimidazole-6-carboxamide,
2-(3'-chlorobiphenyl-4-yl)-N-hydroxy-1H-benzimidazole-6-carboxamide,
N-hydroxy-2-[4-(methylsulfonyl)phenyl]-1H-benzimidazole-6-carboxamide,
2-(4-tert-butylphenyl)-N-hydroxy-1H-benzimidazole-6-carboxamide,
N-hydroxy-2-(4-methoxy-3,5-dimethylphenyl)-1H-benzimidazole-6-carboxamide,
2-(4-nonylphenyl)-N-hydroxy-1H-benzimidazole-6-carboxamide,
2-(4-butylphenyl)-N-hydroxy-1H-benzimidazole-6-carboxamide,
2-(2'-fluorobiphenyl-3-yl)-N-hydroxy-1H-benzimidazole-6-carboxamide,
N-hydroxy-2-[4'-(methylsulfonyl)biphenyl-3-yl]-1H-benzimidazole-6-carboxamide, 2-biphenyl-3-yl-N-hydroxy-1H-benzimidazole-6-carboxamide,
2-(2'-fluorobiphenyl-4-yl)-N-hydroxy-1H-benzimidazole-6-carboxamide,
N-hydroxy-2-[4'-(methylsulfonyl)biphenyl-4-yl]-1H-benzimidazole-6-carboxamide,
2-(2',5'-difluorobiphenyl-3-yl)-N-hydroxy-1H-benzimidazole-6-carboxamide,
2-(3',4'-dimethoxybiphenyl-3-yl)-N-hydroxy-1H-benzimidazole-6-carboxamide,
N-hydroxy-2-[4'-(trifluoromethyl)biphenyl-3-yl]-1H-benzimidazole-6-carboxamide,
N-hydroxy-2-[4'-(trifluoromethyl)biphenyl-4-yl]-1H-benzimidazole-6-carboxamide,
2-(2-fluorobiphenyl-4-yl)-N-hydroxy-1H-benzimidazole-6-carboxamide,
2-(2,2'-difluorobiphenyl-4-yl)-N-hydroxy-1H-benzimidazole-6-carboxamide,
2-(2,5'-difluoro-2'-hydroxybiphenyl-4-yl)-N-hydroxy-1H-benzimidazole-6-carboxamide,
2-(2,4'-difluorobiphenyl-4-yl)-N-hydroxy-1H-benzimidazole-6-carboxamide,
2-(3'-{[(cis)-2,6-dimethylmorpholin-4-yl]methyl}biphenyl-4-yl)-N-hydroxy-1H-benzimidazole-6-carboxamide,
N-hydroxy-2-[3'-(morpholin-4-ylmethyl)biphenyl-4-yl]-1H-benzimidazole-6-carboxamide,
N-hydroxy-2-[3'-(piperidin-1-ylmethyl)biphenyl-4-yl]-1H-benzimidazole-6-carboxamide,
2-{3'-[(diethylamino)methyl]biphenyl-4-yl}-N-hydroxy-1H-benzimidazole-6-carboxamide,
2-(3'-{[bis(2-methylpropyl)amino]methyl}biphenyl-4-yl)-N-hydroxy-1H-benzimidazole-6-carboxamide,
N-hydroxy-2-[4'-(morpholin-4-ylmethyl)biphenyl-4-yl]-1H-benzimidazole-6-carboxamide,
N-hydroxy-2-(4'-{[(3-methoxypropyl)amino]methyl}biphenyl-4-yl)-1H-benzimidazole-6-carboxamide,
2-(4'-formylbiphenyl-4-yl)-N-hydroxy-1H-benzimidazole-6-carboxamide,
N-hydroxy-2-{4'-[(E)-(hydroxyimino)methyl]biphenyl-4-yl}-1H-benzimidazole-6-carboxamide,
2-[4'-(aminomethyl)biphenyl-4-yl]-N-hydroxy-1H-benzimidazole-6-carboxamide,
2-[3'-(dimethylcarbamoyl)biphenyl-4-yl]-N-hydroxy-1H-benzimidazole-6-carboxamide,
N-hydroxy-2-[4'-(hydroxymethyl)biphenyl-4-yl]-1H-benzimidazole-6-carboxamide,
N-hydroxy-2-[4'-(pyrrolidin-1-ylmethyl)biphenyl-4-yl]-1H-benzimidazole-6-carboxamide,
2-{4'-[(dimethylamino)methyl]biphenyl-4-yl}-N-hydroxy-1H-benzimidazole-6-carboxamide,
2-(4'-{[bis(2-methylpropyl)amino]methyl}biphenyl-4-yl)-N-hydroxy-1H-benzimidazole-6-carboxamide,
N-hydroxy-2-[4'-(piperidin-1-ylmethyl)biphenyl-4-yl]-1H-benzimidazole-6-carboxamide,
2-(4'-{cis)-2,6-dimethylmorpholin-4-yl]methyl}biphenyl-4-yl)-N-hydroxy-1H-benzimidazole-6-carboxamide,
N-hydroxy-2-[3'-(hydroxymethyl)biphenyl-4-yl]-1H-benzimidazole-6-carboxamide,
2-(3'-carbamoylbiphenyl-4-yl)-N-hydroxy-1H-benzimidazole-6-carboxamide,
N-hydroxy-2-{4'-[(methylsulfonyl)amino]biphenyl-4-yl}-1H-benzimidazole-6-carboxamide,
N-hydroxy-2-[4-(morpholin-4-ylmethyl)phenyl]-1H-benzimidazole-6-carboxamide,
N-hydroxy-2-[4-(piperidin-1-ylmethyl)phenyl]-1H-benzimidazole-6-carboxamide,
N-hydroxy-2-{4-[(4-methylpiperazin-1-yl)methyl]phenyl}-1H-benzimidazole-6-carboxamide,
N-hydroxy-2-(4-{[(2-methoxyethyl)amino]methyl}phenyl)-1H-benzimidazole-6-carboxamide,
N-hydroxy-2-[3-(morpholin-4-ylmethyl)phenyl]-1H-benzimidazole-6-carboxamide,
N-hydroxy-2-[3-(piperidin-1-ylmethyl)phenyl]-1H-benzimidazole-6-carboxamide,
N-hydroxy-2-{3-[(4-methylpiperazin-1-yl)methyl]phenyl}-1H-benzimidazole-6-carboxamide,
N-hydroxy-2-(3-{[(2-methoxyethyl)amino]methyl}phenyl)-1H-benzimidazole-6-carboxamide,
2-{3-[(dimethylamino)methyl]phenyl}-N-hydroxy-1H-benzimidazole-6-carboxamide,
2-[3,5-bis(trifluoromethyl)phenyl]-N-hydroxy-1H-benzimidazole-6-carboxamide, and
2-(3-bromophenyl)-N-hydroxy-1H-benzimidazole-6-carboxamide,
or a pharmaceutically acceptable salt thereof.

7. A pharmaceutical composition comprising a compound according to claim 1, or a pharmaceutically acceptable salt thereof, and optionally a pharmaceutically acceptable excipient.

8. The compound of claim 1, wherein each $R_4$ is independently selected from halogen, C1-C10 alkyl, and $R_5O$.

9. The compound of claim 8, wherein $R_5$ is selected from H and C1-C6 alkyl.

10. The compound of claim 1, wherein each $R_4$ is independently selected from halogen and C1-C6 alkyl.

11. The compound of claim 5, wherein each $R_4$ is independently selected from halogen, C1-C10 alkyl, and $R_5O$.

12. The compound of claim 11, wherein $R_5$ is selected from H and C1-C6 alkyl.

13. The compound of claim 5, wherein each $R_4$ is independently selected from halogen and C1-C6 alkyl.

14. The compound of claim 1, of formula (Ia-3)

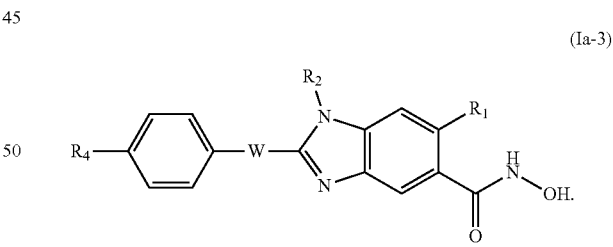

(Ia-3)

15. The compound of claim 14, wherein each $R_4$ is independently selected from halogen, C1-C10 alkyl, and $R_5O$.

16. The compound of claim 14, wherein $R_5$ is selected from H and C1-C6 alkyl.

17. The compound of claim 14, wherein each $R_4$ is independently selected from halogen and C1-C6 alkyl.

* * * * *